US008951572B2

(12) United States Patent
Reisner et al.

(10) Patent No.: US 8,951,572 B2
(45) Date of Patent: Feb. 10, 2015

(54) THERAPEUTIC TRANSPLANTATION USING DEVELOPING, HUMAN OR PORCINE, RENAL OR HEPATIC, GRAFTS

(75) Inventors: Yair Reisner, Old Jaffa (IL); Benjamin Dekel, Tel-Aviv (IL); Smadar Eventov-Friedman, Kibbutz Nachshon-Doar-Na Shimshon (IL); Helena Katchman, Givataim (IL); Elias Shezen, Rehovot (IL); Anna Aronovich, Rehovot (IL); Dalit Tchorsh, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 12/777,292

(22) Filed: May 11, 2010

(65) Prior Publication Data
US 2010/0221270 A1 Sep. 2, 2010

Related U.S. Application Data

(60) Division of application No. 11/037,025, filed on Jan. 19, 2005, now Pat. No. 7,780,993, which is a continuation-in-part of application No. 10/759,033, filed on Jan. 20, 2004, now abandoned, which is a continuation-in-part of application No. 10/379,725, filed on Mar. 6, 2003, now abandoned, which is a continuation-in-part of application No. PCT/IL02/00722, filed on Sep. 1, 2002, which is a continuation-in-part of application No. 10/118,933, filed on Apr. 10, 2002, now abandoned.

(60) Provisional application No. 60/317,452, filed on Sep. 7, 2001.

(51) Int. Cl.
*A61K 35/54* (2006.01)
*A61K 35/407* (2006.01)
*A61K 39/395* (2006.01)
*A61K 35/22* (2006.01)
*A61K 45/06* (2006.01)

(52) U.S. Cl.
CPC ............ *A61K 39/39541* (2013.01); *A61K 35/22* (2013.01); *A61K 35/407* (2013.01); *A61K 35/54* (2013.01); *A61K 45/06* (2013.01)
USPC ........ 424/582; 424/184.1; 424/553; 424/93.1

(58) Field of Classification Search
CPC ..... A61K 35/407; A61K 35/22; A61K 35/54; A61K 2300/00
USPC .............. 424/184.1, 93.1, 553, 582
See application file for complete search history.

(56) References Cited

U.S. PATENT DOCUMENTS

| | | |
|---|---|---|
| 5,175,004 A | 12/1992 | Matsumura |
| 5,580,558 A | 12/1996 | Kitamura |
| 5,635,365 A | 6/1997 | Ansari et al. |
| 5,811,089 A | 9/1998 | Smikodub et al. |
| 5,876,708 A | 3/1999 | Sachs |
| 5,942,435 A | 8/1999 | Wheeler |
| 5,976,524 A | 11/1999 | Hammerman |
| 6,024,957 A | 2/2000 | Lazarovits et al. |
| 6,060,049 A | 5/2000 | Beschorner |
| 6,140,116 A | 10/2000 | Dinsmore |
| 6,183,734 B1 | 2/2001 | Chen et al. |
| 6,194,147 B1 | 2/2001 | Baxter-Lowe et al. |
| 6,274,629 B1* | 8/2001 | Cottens et al. ............... 514/646 |
| 6,610,288 B1 | 8/2003 | Edge et al. |
| 6,660,905 B1* | 12/2003 | Kay et al. .................... 800/8 |
| 2001/0049827 A1 | 12/2001 | Hunter et al. |
| 2003/0032184 A1 | 2/2003 | Lagasse et al. |
| 2003/0096016 A1 | 5/2003 | Reisner et al. |
| 2004/0082064 A1 | 4/2004 | Reisner et al. |
| 2004/0136972 A1 | 7/2004 | Reisner et al. |
| 2004/0191228 A1 | 9/2004 | Reisner et al. |
| 2005/0226854 A1 | 10/2005 | Reisner et al. |
| 2006/0040386 A1* | 2/2006 | Holgersson ............... 435/370 |
| 2009/0324607 A1 | 12/2009 | Reisner et al. |

FOREIGN PATENT DOCUMENTS

| | | |
|---|---|---|
| EP | 0853942 | 7/1998 |
| WO | WO 96/37602 | 11/1996 |
| WO | WO 00/39294 | 7/2000 |
| WO | WO 00/41713 | 7/2000 |
| WO | WO 02/00722 | 1/2002 |
| WO | WO 02/39294 | 5/2002 |
| WO | WO 03/022123 | 3/2003 |
| WO | WO 2004/016276 | 2/2004 |
| WO | WO 2004/078022 | 9/2004 |
| WO | WO 2006/077592 | 7/2006 |

OTHER PUBLICATIONS

Touraine et al. The Place of Fetal Liver Transplantation in the Treatment of Inborn Errors of Metabolism. J. Inher. Metab. Dis. 14 (1991) 619-626.*
Crombleholme et al. Transplantation of fetal cells. Am J Obstet Gynecol 1991;164:218-30.*
Hagihara et al. Effects of iso and xeno fetal liver fragments transplantation on acute and chronic liver failure in rats.Cell Transplant. Jul.-Aug. 1994;3(4):283-90.*
Movahedi et al. Laparoscopic approach for human islet transplantation into a defined liver segment in type4 diabetic patients. Transpl. Int. (2003) 16:186-190.*
European Search Report and the European Search Opinion Dated Nov. 9, 2010 From the European Patent Office Re. Application No. 10154555.6.

(Continued)

Primary Examiner — Taeyoon Kim

(57) ABSTRACT

A method of treating a renal, hepatic or enzyme-deficiency disorder in a subject in need thereof is disclosed. The method is effected by transplanting into the subject tissue derived from a human or porcine, kidney or liver, the kidney or liver being at a selected gestational stage.

13 Claims, 25 Drawing Sheets
(21 of 25 Drawing Sheet(s) Filed in Color)

(56) References Cited

OTHER PUBLICATIONS

Batanov et al. "Effect of Fetal Tissue Transplantation on Reparative Processes in Experimental Liver Cirrhosis", Bulletin of Experimental Biology and Medicine, XP002605657, 130(8): 798-801, Aug. 2000.
Eventov-Friedman et al. "Embryonic Pig Pancreatic Tissue Transplantation for the Treatment of Diabetes", PLoS Medicine, XP002544044, 3(7): 1165-1177, Jul. 1, 2006.
Hecht et al. "Embryonic Pig Pancreatic Tissue for the Treatment of Diabetes in a Nonhuman Primate Model", Proc. Natl. Acad. Sci. USA, PNAS, XP009122169, 106(21): 8659-8664, May 26, 2009.
Lenschow et al. "Long-Term Survival of Xenogeneic Pancreatic Islet Grafts Induced by CTLA4Ig", Science, XP002021689, 257(5071): 789-792, Aug. 7, 1992. Fig. 1.
Sandhu et al. "Stem Cell Properties and Repopulation of the Rat Liver by Fetal Liver Epithelial Progenitor Cells", American Journal of Pathology, XP002605655, 159(4): 1323-1334, Oct. 2001. Figs.1-7.
Sierra et al. "Liver Gene Expression and Increase in Albumin Synthesis by Fetal Hepatocytes Transplanted Into Analbuminemics Rats", Life Sciences, XP002605656, 67(20): 2417-2432, Oct. 6, 2000. Figs.1-4.
Steurer et al. "Ex Vivo Coating of Islet Cell Allografts With Murine CTLA4/Fc Promotes Graft Tolerance", Journal of Immunology, XP002031135, 155(3): 1165-1174, Aug. 1, 1995. Fig.8.
Thomas "The Infusion of Human Fetal Liver Cells", Stem Cells, XP002605658, 11(Suppl.1): 66-71, 1993. & Conference Celebrating the 40th Anniversary of the Institute of Hematology and Blood Transfusion, Prague, Czech Republic, Oct. 23-24, 1992.
Response Dated Feb. 15, 2011 to Office Action of Sep. 15, 2010 From the Israel Patent Office Re. Application No. 170622.
Communication Pursuant to Article 96(2) EPC Dated Feb. 16, 2007 From the European Patent Office Re.: Application No. 02758769.0.
International Preliminary Report on Patentability Dated Aug. 2, 2007 From the International Bureau of WIPO Re.: Application No. PCT/IL2006/000085.
International Preliminary Report on Patentability Dated Nov. 15, 2007 From International Bureau of WIPO Re.: Application No. PCT/IL2004/000217.
Official Action Dated Aug. 8, 2007 From the US Patent and Trademark Office Re.: U.S. Appl. No. 11/037,025.
Official Action Dated Feb. 8, 2007 From the US Patent and Trademark Office Re.: U.S. Appl. No. 10/759,033.
Official Action Dated Apr. 10, 2008 From the US Patent and Trademark Office Re.: U.S. Appl. No. 11/037,025.
Official Action Dated Nov. 25, 2008 From the US Patent and Trademark Office Re.: U.S. Appl. No. 11/037,025.
Supplementary Partial European Search Report Dated Feb. 28, 2006 From the European Patent Office Re.: Application No. 02758769.0.
Communication Pursuant to Article 94(3) EPC Dated Nov. 24, 2009 From the European Patent Office Re.: Application No. 02758769.0.
Communication Pursuant to Article 94(3) EPC Dated Nov. 26, 2008 From the European Patent Office Re.: Application No. 06701102.3.
Communication Pursuant to Article 94(3) EPC Dated Aug. 31, 2009 From the European Patent Office Re.: Applicaiton No. 04717207.7.
Communication Relating to the Results of the Partial International Search Dated May 30, 2006 From the International Searching Authority Re.: Application No. PCT/IL2006/000085.
Decision of the Enlarged Board of Appeal Dated Nov. 25, 2009 From the European Patent Office Re.: Application No. 96903521.1.
Examiner's Report Dated Mar. 12, 2007 From the Australian Government, IP Australia Re.: Application No. 2002324324.
Examiner's Report Dated Aug. 13, 2008 From the Australian Government, IP Australia Re.: Application No. 2004217938.
International Preliminary Examination Report Dated Aug. 17, 2007 From the International Preliminary Examining Authority Re.: Application No. PCT/IL02/00722.
International Search Report and the Written Opinion Dated Oct. 16, 2007 From the International Searching Authority Re.: Application No. PCT/IL04/00217.
Notice of Allowance Dated Feb. 23, 2010 From the US Patent and Trademark Office Re.: U.S. Appl. No. 11/037,025.
Office Action Dated Feb. 11, 2009 From the Israeli Patent Office Re.: Application No. 160723 and its Translation Into English.
Office Action Dated May 14, 2007 From the Israeli Patent Office Re.: Application No. 160723.
Office Action Dated Feb. 17, 2010 From the Israel Patent Office Re.: Application No. 184740 and its Translation Into English.
Official Action Dated Apr. 9, 2007 From the US Patent and Trademark Office Re.: U.S. Appl. No. 11/037,025.
Official Action Dated Jul. 10, 2009 From the US Patent and Trademark Office Re.: U.S. Appl. No. 11/037,025.
Official Action Dated Feb. 13, 2006 From the US Patent and Trademark Office Re.: U.S. Appl. No. 10/379,725.
Requisition by the Examiner Dated Jul. 31, 2009 From the Canadian Intellectual Property Office Re.: Application No. 2,459,560.
Supplementary European Search Report Dated Jun. 2, 2009 From the European Patent Office Re.: Application No. 04717207.7.
Supplementary European Search Report Dated May 23, 2006 From the European Patent Office Re.: Application No. 02758769.0.
Translation of Notice of Reason for Rejection Dated May 19, 2009 From the Japanese Patent Office Re.: Application No. 2003-526257.
Written Opinion Dated Mar. 1, 2006 From the International Preliminary Examining Authority Re.: Application No. PCT/IL02/00722.
Abrahamson et al. "Glomerular Development in Intraocular and Intrarenal Grafts of Fetal Kidneys", Laboratory Investigation, 64(5): 629-639, 1991.
Ashkar et al. "Eta-1 (Osteopontin): An Early Component of Type-1 (Cell-Mediated) Immunity", Science, 287: 860-863, 2000.
Assmus et al. "Transplantation of Progenitor Cells and Regeneration Enhancement in Acute Myocardial Infarction (TOPCARE-AMI)", Circulation, 106: 3009-3017, 2002.
Auchincloss et al. "Xenogeneic Transplantation", Annual Reviews in Immunology, 16: 433-470, 1998.
Barakat et al. "The Capacity of Fetal and Neonatal Renal Tissues to Regenerate and Differentiate in a Heterotopic Allogeneic Subcutaneous Tissue Site in the Rat", Journal of Anatomy, 110(3): 393-407, 1971.
Barry "Renal Transplantation", Current Opinion in Urology, 10(4): 121-127, 1999.
Benhamou "Immunomodulation With CTLA4-Ig in IsletTransplantation", Transplantation, 73(1): S40-S42, 2002.
Benichou et al. "Contributions of Direct and Indirect T Cell Alloreactivity During Allograft Rejection in Mice", The Journal of Immunology, 162: 352-358, 1999.
Biancone et al. "Study of Lymphocyte Costimulatory Molecules in Renal Transplantation", Transplantation Proceedings, 30: 2384-2386, 1998.
Boussiotis et al. "Differential Association of Protein Tyrosine Kinases With the T Cell Receptor is Linked to the Induction of Anergy and its Prevention by B7 Family-Mediated Costimulation", Journal of Experimental Medicine, 184: 365-376, 1996.
Brandhagen "Liver Transplantation for Hereditary Hemochromatosis", Liver Transplantation, 7(8): 663-672, 2001.
Braunwald "Shattuck Lecture—Cardiovascular Medicine at the Turn of the Millennium: Triumphs, Concerns, and Opportunities", The New England Journal of Medicine, 337(19): 1360-1370, 1997.
Briscoe et al. "The Allogeneic Response to Cultured Human Skin Equivalent in the Hu-PBL-SCID Mouse Model of Skin Rejection", Transplantation, 67(12): 1590-1599, 1999.
Britten et al. "Infarct Remodeling After Intracoronary Progenitor Cell Treatment in Patients With Acute Myocardial Infarction (TOPCARE-AMI). Mechanistic Insights From Serial Contrast-Enhanced Magnetic Resonance Imaging", Circulation, 108: 2212-2218, 2003.
Cascalho et al. "The Immunological Barrier to Xenotransplantation", Immunity, 14: 437-446, 2001.
Castaing et al. "Blood Glucose Normalization Upon Transplantation of Human Embryonic Pancreas Into Beta-Cell-Deficient SCID Mice", Diabetologia, 44: 2066-2076, 2001.
Cecka "Kidney Transplantation From Living Unrelated Donors", Annual Review of Medicine, 51:393-406, 2000.

(56) References Cited

OTHER PUBLICATIONS

Crippin "Motion—Patients With Primary Sclerosing Cholangitis Should Undergo Early Liver Transplantation: Arguments Against the Motion", Canadian Journal of Gastroenterology, 16: 700-702, 2002.
Curtis "End-Stage Renal Disease Patients: Referral for Transplantation", Journal of the American Society of Nephrology, 9: 5137-5140, 1998.
Dantal et al. "Effect of Long-Term Immunosuppression in Kidney-Graft Recipients on Cancer Incidence: Randomised Comparison of Two Cyclosporin Regimens", Lancet, 351: 623-628, 1998.
Dekel et al. "Acute Cellular Rejection of Human Renal Tissue by Adoptive Transfer of Allogeneic Human Peripheral Blood Mononuclear Cells Into Chimeric Rats: Sequential Gene Expression of Cytokines, Chemokines and Cytolytic Effector Molecules, and Their Regulation by CTLA-4-Ig", International Immunology, 11(10): 1673-1683, 1999.
Dekel et al. "Engraftment of Human Early Kidney Precursors", Transplant Immunology, XP002378905, 12(3-4): 241-247, Apr. 1, 2004. p. 242, col. 2, § 1, Fig.2, Abstract.
Dekel et al. "Engraftment of Human Early Kidney Precursors", XP002378905, Transplant Immunology, 12(3-4): 241-247, 2004. Abstract.
Dekel et al. "Engraftment of Human Kidney Tissue in Rat Radiation Chimera: I. A New Model of Human Kidney Allograft Rejection", Transplantation, 64(11): 15411550, 1997.
Dekel et al. "Engraftment of Human Kidney Tissue in Rat Radiation Chimera: II. Human Fetal Kidneys Display Reduced Immunogenicity to Adoptively Transferred Human Peripheral Blood Mononuclear Cells and Exhibit Rapid Growth and Development", Transplantation, 64(11): 1550-1558, 1997.
Dekel et al. "In Vivo Modulation of the Allogeneic Immune Response by Human Fetal Kidneys: The Role of Cytokines, Chemokines, and Cytolytic Effector Molecules", Transplantation, XP009061859, 69(7): 1470-1478, Apr. 15, 2000. p. 1472, r-h Col.
Eisen et al. "Cluster Analysis and Display of Genome-Wide Expression Pattern", Proc. Natl. Acad. Sci. USA, 95: 14863-14868, 1998.
Eriksson "Heart Failure: A Growing Public Health Problem", Journal of Internal Medicine, 237: 135-141, 1995.
Eventov-Friedman et al. "Embryonic Pig Liver, Pancreas, and Lung as a Source for Transplantation: Optimal Organogenesis Without Teratoma Depends on Distinct Time Windows", Proc. Natl. Acad. Sci. USA, XP002527680, 102(8): 2928-2933, Feb. 22, 2005.
Findlay et al. "Human Embryo: A Biological Definition", Human Reproduction, XP009125896, 22(4): 905-911, 2007.
Fischer et al. "Stem Cell Transplantation for Immunodeficiency", Springer Seminars in Immunopathology, 19: 479-492, 1998.
Freed Will Embryonic Stem Cells Be a Useful Source of Dopamine Neurons for Transplant Into Patients With Parkinson's Disease? Proc. Natl. Acad. Sci. USA (PNAS), 99(4): 1755-1757, 2002.
French et al. "Progress in Renal Transplantation", The Canadian Journal of Urology, 7(3): 1030-1037, 2000.
Friedrich "Bone Marrow Transplantation in Immunodeficiency Diseases", The Finnish Mediacl Society DUODECIM, Annals in Medicine, 28: 115-119, 1996.
Frilling et al. "Current Status of Liver Transplantation for Treatment of Hepatocellular Carcinoma", Digestive Diseases, 19: 333-337, 2001.
Gritsch et al. "The Importance of Nonimmune Factors in Reconstitution by Discordant Xenogeneic Hematopoietic Cells", Transplantation, 57(6): 906-917, 1994.
Groth et al. "Splenic Transplantation in Gaucher Disease", Birth Defects: Original Article Series, IX(2): 102-105, 1973.
Groth et al. "Xenoislet Transplantation: Experimental and Clinical Aspects", Journal of Molecular Medicine, 77: 153-154, 1999.
Hammerman "Transplantation of Embryonic Kidneys", Clinical Science, 103: 599-612, 2002.
Hammerman "Transplantation of Renal Precursor Cells: A New Therapeutic Approach", Pediatr. Nephrol., 14: 513-517, 2000.
Hammerman "Xenotransplantation of Renal Primordia", Current Opinion in Nephrology and Hypertension, 11: 11-16, 2002.
Hanto "Classification of Epstein-Barr Virus-Associated Post-transplant Lymphoproliferative Diseases: Implications for Understanding Their Pathogenesis and Developing Rational Treatment Strategies", Annu. Rev. Med., 46: 381-394, 1995.
Higgins et al. "Prevention of Hyperacute Rejection by Removal of Antibodies to HLA Immediately Before Renal Transplantation", The Lancet, 348: 1208-1211, 1996.
Horwitz "Primary Immune Deficiencies: Presentation, Diagnosis, and Management. Stem-Cell Transplantation for Inherited Immunodeficiency Disorders", Pediatric Clinics of North America, 47(6): 1371-1387, 2000.
Howard "What is Primary Biliary Cirrhosis?", http://www.cumc.columbia.edu/dept/gi/PBC.html, p. 1-2.
Ishizaka et al. "Development of Hepatocytes From ES Cells After Transfection With the HNF-3β Gene", The FASEB Journal, 16: 1444-1446, 2002.
Itskovitz-Eldor et al. "Differentiation of Human Embryonic Stem Cells Into Embryonic Bodies Comprising the Three Embryonic Germ Layers", Molecular Medicine, 6(2): 88-95, 2000.
Jones et al. "Hepatic Differentiation of Murine Embryonic Stem Cells", Experimental Cell Research, 272: 15-22, 2002.
Kaminski et al. "Global Analysis of Gene Expression in Pulmonary Fibrosis Reveals Distinct Programs Regulating Lung Inflammation and Fibrosis", Proc. Natl. Acad. Sci. USA, 97(4): 1778-1783, 2000.
Kaminski et al. "Practical Approaches to Analyzing Results of Microarray Experiments", Am. J. Respir. Cell Mol. Biol., 27: 125-132, 2002.
Kanai et al. "Delayed Hyperacute Xenograft Rejection in Porcine to Canine Fetal Liver Transplantation", Transplant Immunology, 7: 95-99, 1999.
Kane et al. "Neonatal Bone Marrow Transplantation for Severe Combined Immunodeficiency", Archives of Disease in Childhood—Fetal and Neonatal Edition, 85: 110-113, 2001.
Katchman et al. "Embryonic Porcine Liver as a Source for Transplantation: Advantage of Intact Liver Implants Over Isolated Hepatoblasts in Overcoming Homeostatic Inhibition by the Quiescent Host Liver", Stem Cells, 26: 1347-1355, 2008.
Keeffe "Liver Transplantation at the Millenium—Past, Present, and Future", Hepatology: A Century of Progress, p. 242-255, 2000.
Keeffe "Liver Transplantation: Current Status and Novel Approaches to Liver Replacement", Gastroenterology, 120: 749-762, 2001.
Kirkpatrick et al. "Transplantation Immunology", JAMA, 268(20): 2952-2958, 1992.
Koerner et al. "Cardiac Transplantation: The Final Therapeutic Option for the Treatment of Heart Failure", Current Opinion in Cardiology, 15: 178-182, 2000.
Kokudo et al. "Allogeneic Heopatocyte and Fetal Liver Transplantation and Xenogeneic Hepatocyte Transplantation for Nagase's Analbuminemic Rats", Cell Transplantation, 5(5S-1): S21-S22, 1996.
Kreisel et al. "Non-Hematopoietic Allograft Cells Directly Activate CD8+ T Cells and Trigger Acute Rejection: An Alternative Mechanism of Allorecognition", Nature Medicine, 8(3): 233-239, 2002.
Lee et al. "Efficient Generation of Midbrain and Hindbrain Neurons From Mouse Embryonic Stem Cells", Nature Biotechnology, 18: 675-679, 2000.
Levite et al. "Beneficial Effects of Bone Marrow Transplantation on the Serological Manifestations and Kidney Pathology of Experimental Systemic Lupus Erythematosus", Cellular Immunology, 162: 138-145, 1995.
Li et al. "Blocking Both Signal 1 and Signal 2 of T-Cell Activation Prevents Apoptosis of Alloreactive T Cells and Induction of Peripheral Allograft Tolerance", Nature Medicine, 5(11): 1298-1302, 1999.
Linsley et al. "CTLA-4 is a Second Receptor for the B Cell Activation Antigen B7", Journal of Experimental Medicine, 174: 561-569, 1991.
Liu et al. "Transplantation of Spleen Celles in Patients With Hemophilia A. A Report of 20 Cases", Transplant International, 7(3): 201-206, 1994.
Lubin et al. "Engraftment of Human Peripheral Blood Lymphocytes in Normal Strains of Mice", Blood, 83(8): 2368-2381, 1994.

(56) References Cited

OTHER PUBLICATIONS

Lumelsky et al. "Differentiation of Embryonic Stem Cells to Insulin-Secreting Structures Similar to Pancreatic Islets", Science, 292: 1389-1394, 2001.
Marcus et al. Human/Mouse Radiation Chimera are Capable of Mounting a Human Primary Humoral Response, Blood, 86(1): 398-406, 1995.
Medawar "Some Immunological and Endocrinological Problems Raised by the Evolution of Viviparitiy in Vertebrates", Symposium of the Society of Experimental Biology, 7: 320-323, 1953.
Michler et al. "Treatment of Cardiac Tumors by Orthotopic Cardiac Transplantation", Seminars in Oncology, 24(5): 534-539, 1997.
Midthun et al. "Medical Management and Complications in the Lung Transplant Recipient", Mayo Clin. Proc., 72: 175-184, 1997.
Molmenti et al. "Hepatocellular Cancer in Liver Transplantation", Journal of Hepatobiliary and Pancreatic Surgery, 8: 427-434, 2001.
Moore et al. "Stem Cell Transplantation for Autoimmune Diseases", Springer Seminars in Immunopathology, 23: 193-213, 2001.
Morrison et al. "Clinical Characteristics of Post-Transplant Lymphoproliferative Disorders", The American Journal of Medicine, 97: 14-24, 1994.
Naveh-Many et al. "Estrogen Receptors and Biologic Response in Rat Parathyroid Tissue and C Cells", Journal of Clinical Investigation, 90: 2434-2438, 1992.
Nelson et al. "Chemokines, Chemokine Receptors, and Allograft Rejection", Immunity, 14: 377-386, 2001.
Odorico et al. "Multilineage Differentiation From Human Embryonic Stem Cell Lines", Stem Cells, XP002256790, 19(3): 193-204, 2001.
Oliver et al. "Metanephric Mesenchyme Contains Embryonic Renal Stem Cells", American Journal of Physiology—Renal Physiology, 283: 799-809, 2002.
O'Regan et al. "Osteopontin (Eta-1) in Cell-Mediated Immunity: Teaching an Old Dog New Tricks", Immunology Today, 21(10): 475-478, 2000.
Otonkoski et al. "Differentiation and Maturation of Porcine Fetal Islet Cells In Vitro and After Transplantation", Transplantation, 68(11): 1674-1683, 1999.
Otto "Lung Stem Cells", International Journal of Experimental Pathology, 78: 291-310, 1997.
Parkman "Bone Marrow Transplantation for Immunodeficiency and Metabolic Diseases", Leukemia, 7: 1100-1102, 1993.
Perin et al. "Transendocardial, Autologous Bone Marrow Cell Transplantation for Severe, Chronic Ischemic Heart Failure", Circulation, 107: 2294-2304, 2003.
Podevin et al. "Transplantation Hépatique pour Maladie Alcoolique du Fois", Journal du Chirurgie, 138(3): 147-152, 2001.
Porter "The Graft-Versus-Tumor Potential of Allogeneic Cell Therapy: An Update on Donor Leukocyte Infusions and Nonmyeloablative Allogeneic Stem Cell Transplantation", Journal of Hematotherapy & Stem Cell Research, 10: 465-480, 2001.
Pouzet et al. "Transplantation de Myoblastes Squelettiques Autologues Dans l'Insuffisance Cardiaque Ischémique", Journal de la Société de Biologie, 195(1): 47-49, 2001.
Pratt et al. "Local Synthesis of Complement Component C3 Regulates Acute Renal Transplant Rejection", Nature Medicine, 8(6): 582-587, 2002.
Ramanathan et al. "Renal Transplantation", Seminars in Nephrology, 21(2): 213-219, 2001.
Reisner et al. "The Trimera Mouse: Generating Human Monoclonal Antibodies and an Animal Model for Human Diseases", Trends in Biotechnology, 16: 242-246, 1998.
Reubinoff et al. "Embryonic Stem Cell Lines From Human Blastocysts: Somatic Differentiation In Vitro", Nature Biotechnology, 18: 399-404, 2000.
Robert et al. "Evidence That Embryonic Kidney Cells Expressing Flk-1 are Intrinsic, Vasculogenic Angioblasts", The American Journal of Physiology, 271 (Renal Fluid Electrolyte Physiology 40): F744-F753, 1996.
Rogers et al. "Transplantation of Developing Metanephroi Into Adult Rats", Kidney International, 54: 27-37, 1998.
Rogers et al. "Transplantation of Metanephroi Across the Major Histocompatibility Complex in Rats", The American Journal of Physiology—Regulatory, Integrative and Comparative Physiology, 280: 132-136, 2001.
Rogers et al. "Transplantation of Metanephroi After Preservation In Vitro", The American Journal of Physiology—Regulatory, Integrative and Comparative Physiology, 281: 661-665, 2001.
Rogers et al. "Transplantation of Pig Metanephroi", ASAIO Journal, 49: 48-52, 2003.
Rogers et al. "Transplantation of Rat Metanephroi Into Mice", Am. J. Physiol. Regul. Integr. Comp. Physiol., 280: R1865-R1869, 2001.
Samuel "Hepatitis B Virus and Liver Transplantation", Acta Gastro-Enterologica Belgica, LXIII: 197-199, 2000.
Sayegh et al. "The Role of T-Cell Costimulatory Activation Pathways in Transplant Rejection", The New England Journal of Medicine, 338(25): 1813-1821, 1998.
Schuldiner et al. "Effects of Eight Growth Factors on the Differentiation of Cells Derived From Human Embryonic Stem Cells", Proc. Natl. Acad. Sci. USA, 97(21): 11307-11312, 2000.
Schumacher et al. "Transplantation of Embryonic Porcine Mesencephalic Tissue in Patients With PD", Neurology, 54(5): 1042-1050, 2000.
Schwartz "Models of T Cell Anergy: Is There a Common Molecular Mechanism", The Journal of Experimental Medicine, 184: 1-8, 1996.
Seaman "Adult Living Donor Liver Transplantation: Current Status", Journal of Clinical Gastroenterology, 33(2): 97-106, 2001.
Segall et al. "Generation of Primary Antigen-Specific Human Cytotoxic T Lymphocytes in Human/Mouse Radiation Chimera", Blood, 88(2): 721-730, 1996.
Senderowicz et al. "Complete Sustained Response of a Refractory, Post-Transplantation, Large B-Cell Lymphoma to an Anti-CD22 Immunotoxin", Ann. Intern. Med., 126(11): 882-885, 1997.
Sharma et al. "Molecular Executors of Cell Death-Differential Intrarenal Expression of Fas Ligand, Fas, Granzyme B, and Perforin During Acute and/or Chronic Rejection of Human Renal Allografts", Transplantation, 62(12): 1860-1866, 1996.
Soria et al. "Insulin-Secreting Cells Derived From Embryonic Stem Cells Normalize Glycemia in Streptozotocin-Induced Diabetic Mice", Diabetes, 49: 1-6, 2000.
Speziali et al. "Cardiac Transplantation for End-Stage Congenital Heart Defects: The Mayo Clinic Experience", Mayo Clinic Proceedings, 73(10): 923-928, 1998.
Stamm et al. "Autologous Bone-Marrow Stem-Cell Transplantation for Myocardial Regeneration", The Lancet, Research Letters, 361: 45-46, 2003.
Strauer et al. "Intrakoronare, Humane Autologe Stammzelltransplantation zur Myokardregeneration nach Herzinfarkt", Deutsche Medizinische Wochenschrift, 126: 932-938, 2001.
Strauer et al. "Repair of Infarcted Myocardium by Autologous Intracoronary Mononuclear Bone Marrow Cell Transplantation in Humans", Circulation: 106: 1913-1918, 2002.
Subramanian "Cell Transplantation for the Treatment of Parkinson's Disease", Seminars in Neurology, 21(1): 103-115, 2001.
Suthanthiran et al. "Renal Transplantation", The New England Journal of Medicine, 331(6): 365-376, 1996.
Takebe et al. "Xenogeneic (Pig to Rat) Fetal Liver Fragment Transplantation Using Macrocapsules for Immunoisolation", Cell Transplantation, 5(5S-1): S31-S33, 1996.
Tedder et al. "The Selectins: Vascular Adhesion Molecules", The FASEB Journal, 9: 866-873, 1995.
Thomson et al. "Embryonic Stem Cell Lines Derived From Human Balstocysts", Science, 282: 1145-1147, 1998.
Toungouz et al. "Hematopoietic Stem Cells: Therapeutic Applications in Autoimmune Diseases and in Solid Organ Transplantation", Advances in Nephrology, 31(Chap.18): 257-272, 2001.
Usadel et al. "Transplantation of human Fetal Pancreas. Experience in Thymusaplastic Mice and Rats and in a Diabetic Patient", Diabetes, 29(Suppl.1): 74-79, 1980.
Van Thiel et al. "Liver Transplantation for Fulminant Hepatic Failure", Journal of Gastroenterology, 36: 1-4, 2001.

(56) References Cited

OTHER PUBLICATIONS

Vermeulen et al. "Quantification of Angiogenesis in Solid Human Tumours: An International Consensus on the Methodology and Criteria of Evaluation", European Journal of Cancer, 32A(14): 2474-2484, 1996.
Vincenti et al. "Inerleukin-2-Receptor Blockade With Daclizumab to Prevent Acute Rejection in Renal Transplantation", The New England Journal of Medicine, 338(3): 161-166, 1998.
Woolf "The Kidney: 1. Embryology", Pediatric Nephrology, 4th Ed., Section I(Chap.1): 1-19, 1999.
Worman "What is Primary Biliary Cirrhosis (PBC)?", Columbia University Medical Center, Gastroenterology, 2 P., 2004. http://www.cumc.columbia.edu/dept/giPBC.html, 2004.
Xie et al. "Expression, Roles, Receptors, and Regulation of Osteopontin in the Kidney", Kidney International, 60: 1645-1657, 2001.
Zuo et al. "Gene Expression Analysis Reveals Matrilysin as a Key Regulator of Pulmonary Fibrosis in Mice and Humans", Proc. Natl. Acad. Sci. USA, 99(9): 6292-6297, 2002.
Response Dated Jun. 17, 2010 to Office Action of Feb. 17, 2010 From the Israel Patent Office Re.: Application No. 184740.
Office Action Dated Mar. 22, 2010 From the Israeli Patent Office Re.: Application No. 160723, its Replacement Pages Presenting Claims and its Translation Into English.
Office Action Dated Jun. 6, 2010 From the Israeli Patent Office Re.: Application No. 160723 and its Translation Into English.
Partial European Search Report Dated Jul. 1, 2010 From the European Patent Office Re. Application No. 10154555.6.
Yoon et al. "Differentiation and Expansion of Beta Cell Mass in Porcine Neonatal Pancreatic Cell Clusters Transplanted Into Nude Mice", Cell Transplantation, XP008005474, 8(6): 673-689, Nov. 1, 1999. Fig.10.
Official Action Dated Aug. 4, 2010 From the US Patent and Trademark Office Re. U.S. Appl. No. 11/795,480.
Office Action Dated Sep. 15, 2010 From the Israel Patent Office Re. Application No. 170622 and its Translation Into English.
Response Dated Oct. 4, 2010 to Office Action of Jun. 6, 2010 From the Israeli Patent Office Re.: Application No. 160723.
Bjorklund et al. "Embryonic Stem Cells Develop Into Functional Dopaminergic Neurons After Transplantation in a Parkinson Rat Model", Proc. Natl. Acad. Sci. USA (PNAS), 99(4): 2344-2349, 2002.
Bocher et al. "Induction of Strong Hepatitis B Virus (HBV) Specific T Helper Cell and Cytotoxic T Lymphocyte Responses by Therapeutic Vaccination in the Trimera Mouse Model of Chronic HBV Infection", European Journal of Immunology, 31: 2071-2079, 2001.
Hammerman "Transplantation of Embryonic Organs—Kidney and Pancreas", American Journal of Transplantation, 4(Suppl.6): 14-24, 2004.
Hyink et al. "Endogenous Origin of Glomerular Endothelial and Mesangial Cells in Grafts of Embryonic Kidneys", Am. J. Physiol., 270(Renal Fluid Electrolyte Physiol.39): F886-F899, 1996.
Otonkoski et al. "Differentiation and Maturation of Porcine Fetal Islet Cells In Vitro and After Transplantation", Transplantation, XP009007988, 68(11): 1674-1683, Dec. 15, 1999. p. 1676, Fig.2.
Yoon et al. "Differentiation and Expansion of Beta Cell Mass in Porcine Neonatal Pancreatic Cell Clusters Transplanted Into Nude Mice", Cell Transplantation, XP008005474, 8(6): 673-689, Nov. 1, 1999. Abstract. Fig.10.
Communication Pursuant to Article 94(3) EPC Dated Nov. 18, 2011 From the European Patent Office Re. Application No. 10154555.6.
European Search report and the European Search Opinion Dated Dec. 1, 2011 From the European Patent Office Re. Application No. 11179593.6.
Aronovich et al. "Correction of Hemophilia as a Proof of Concept for Treatment of Monogenic Diseases by Fetal Spleen Transplantation", Proc. Natl. Acad. Sci. USA, PNAS, XP055011328, 103(50): 19075-19080, Dec. 12, 2006.

Lee et al. "Specific Tolerance Across a Discordant Xenogeneic Transplantation Barrier", Proc. Natl. Acad. Sci. USA, XP002663071, 91(23): 10864-10867, Nov. 1994.
Nikolic et al. "Normal Development in Porcine Thymus Grafts and Specific Tolerance of Human T Cells to Porcine Donor MIIC", The Journal of Immunology, XP002663072, 162(6): 3402-3407, Mar. 15, 1999.
Shibata et al. "SCID-Bg Mice as Xenograft Recipients", Laboratory Animals, XP009091838, 31(2): 163-168, Jan. 1, 1997. Figs.4, 5.
Turner et al. "In Utero Transplantation of Human Fetal Haemotopoietic Cells in NOD/SCID Mice", British Journal of Haematology, XP002941795, 103: 326-334, Jan. 1, 1998.
Westermann et al. "Immunoarchitecture of Regenerated Splenic Transplants: Influence of Donor and Host Age on the Regeneration of Splenic Compartments", Cell and Tissue Research, XP009153789, 254(2): 403-413, Nov. 1988. Fig.6.
Communication Pursuant to Article 94(3) EPC Dated Jun. 29, 2011 From the European Patent Office Re. Application No. 10154555.6.
Office Action Dated Oct. 6, 2011 From the Israel Patent Office Re.: Application No. 184740 and its Translation Into English.
Rresponse Dated Oct. 27, 2011 to Communication Pursuant to Article 94(3) EPC of Jun. 29, 2011 From the European Patent Office Re. Application No. 10154555.6.
Communication Pursuant to Article 94(3) EPC Dated Jul. 25, 2012 From the European Patent Office Re. Application No. 11179593.6.
Office Action Dated Apr. 3, 2012 From the Israel Patent Office Re. Application No. 170622 and its Translation Into English.
Communication Pursuant to Rules 70(2) and 70a(2) EPC and Reference to Rule 39(1) EPC Dated Jan. 9, 2012 From the European Patent Office Re. Application No. 11179593.6.
Dabeva et al. "Hepatic Stem Cells and Liver Repopulation", Seminars in Liver Disease, 23(4): 349-362, 2003.
Desgrandchamps et al. "The Prosthetic Ureter", Journal of Endourology, 14(1): 63-77, Feb. 2000.
Gupta et al. "Permanent Engraftment and Function of Hepatocytes Delivered to the Liver: Implications for Gene Therapy and Liver Repopulation", Hepatology, 14(1): 144-149, 1991.
Habibullah et al. "Human Fetal Hepatocyte Transplantation in Patients With Fulminant Hepatic Failure", Transplantation, 58(8): 951-952, Oct. 27, 1994.
Kanazawa et al. "Prospects for Zenotransplantation of the Liver", Seminars in Liver Disease, 20(4): 511-522, 2000.
Lupp et al. "Evaluation of 2-Year-Old Intrasplenic Fetal Liver Tissue Transplants in Rats", Cell Transplantation, 12: 423-438, 2003.
Malhi et al. "Early Cell Transplantation in LEC Rats Modeling Wilson's Disease Eliminates Hepatic Copper With Reversal of Liver Disease", Gastroenterology, 122: 438-447, 2002.
Nagata et al. "Basic-Liver, Pancreas, and Biliary Tract. Treatment of Cirrhosis and Liver Failure in Rats by Hepatocyte Xenotransplantation", Gastroenterology, 124: 422-431, 2003.
Communication Pursuant to Rules 70(2) and 70a (2) EPC and Reference to Rule 39(1) EPC Dated Dec. 6, 2010 From the European Patent Office Re. Application No. 10154555.6.
Communication Under Rule 71(3) EPC Dated Sep. 26, 2012 From the European Patent Office Re. Application No. 10154555.6.
Examination Report Dated Jun. 19, 2008 From the Instituto Mexicano de la Propriedad Industrial Re.: Application No. PA/a/2004/002160.
Björklund et al. "Embryonic Stem Cells Develop Into Functional Dopaminergic Neurons After Transplantation in a Parkinson Rat Model", Proc. Natl. Acad. Sci. USA (PNAS), 99(4): 2344-2349, 2002.
Böcher et al. "Induction of Strong Hepatitis B Virus (HBV) Specific T Helper Cell and Cytotoxic T Lymphocyte Responses by Therapeutic Vaccination in the Trimera Mouse Model of Chronic HBV Infection", European Journal of Immunology, 31: 2071-2079, 2001.
Castaing et al. "Blood Glucose Normalization Upon Transplantation of Human Embryonic Pancreas Into Beta-Cell-Deficient SCID Mice", Diabetologia, XP002235309, 44(11): 2066-2076, Nov. 1, 2001.

(56) References Cited

OTHER PUBLICATIONS

Dekel et al. "Engraftment and Differentiation of Human Metanephroi Into Functional Mature Nephrons After Transplantation Into Mice is Accompanied by a Profile of Gene Expression Similar to Normal Human Kidney Development", Journal of the American Society of Nephrology, XP002367823, 13(4): 977-990, Apr. 1, 2002. Fig.1.
Dekel et al. "Human and Porcine Early Kidney Precursors as a New Source for Transplantion", Nature Medicine, XP002378906, 9(1): 53-60, Jan. 1, 2003. Table 1.
Gaweco et al. "CD40 Expression on Graft Infiltrates and Parenchymal CD154 (CD40L) Induction in Human Chronic Renal Allograft Rejection", Kidney International, 55: 1543-1552, 1999.
Hammerman "Transplantation of Embryonic Organs—Kidney and Pancreas", American Journal of Transplantation, 4(Suppl.6): 14-24, 2004.
Hori et al. "Growth Inhibitors Promote Differentiation of Insulin-Producing Tissue From Embryonic Stem Cells", Proc. Natl. Acad. Sci. USA, PNAS, XP002392968, 99(25): 61105-61110, Dec. 10, 2002.
Hyink et al. "Endogenous Origin of Glomerular Endothelial and Mesangial Cells in Grafts of Embryonic Kidneys", Am. J. Physiol., 270(Renal Fluid Electrolyte Physiol.39): F886-F899, 1996.
Ishizaka et al. "Development of Hepatocytes From ES Cells After Transfection With the HNF-3? Gene", The FASEB Journal, 16: 1444-1446, 2002.
Nikolic et al. "Normal Development in Porcine Thymus Grafts and Specific Tolerance of Human T Cells to Porcine Donor MHC", The Journal of Immunology, XP002663072, 162(6): 3402-3407, Mar. 15, 1999.
Podevin et al. "Transplantation H?patique pour Maladie Alcoolique du Fois", Journal du Chirurgie, 138(3): 147-152, 2001.
Pouzel et al. "Transplantation de Myoblastes Squelettiques Aulologues Dans l'Insuffisance Cardiaque Isch?mique", Journal de la Soci?t? de Biologie, 195(1): 47-49, 2001.
Rogers et al. "Transplantation of Rat Metanephroi Into Mice", American Journal of Physiology: Regulatory, Integrative and Comparative Physiology, XP002259735, 280: R1865-R1869, Jun. 1, 2001.
Shibata et al. "SCID-Bg Mice as Xenograft Recipients", Laboratory Animals, XP009091838, 31(2): 163-168 Jan. 1, 1997. Figs.4,5.
Usadel et al. "Transplantation of human Fetal Pancreas. Experience in Thymusaplastic Mice and Rats and in a Diabetic Patient", Diabetes, 29(Suppl.1): 74-79, 1980.
Communication Pursuant to Article 94(3) EPC Dated Mar. 6, 2012 From the European Patent Office Re. Application No. 10154555.6.
Office Action Dated Oct. 24, 2013 From the Israel Patent Office Re. Application No. 170622 and its Translation Into English.
Communication Pursuant to Article 94(3) EPC Dated Jun. 10, 2014 From the European Patent Office Re. Application No. 11179593.6.

\* cited by examiner

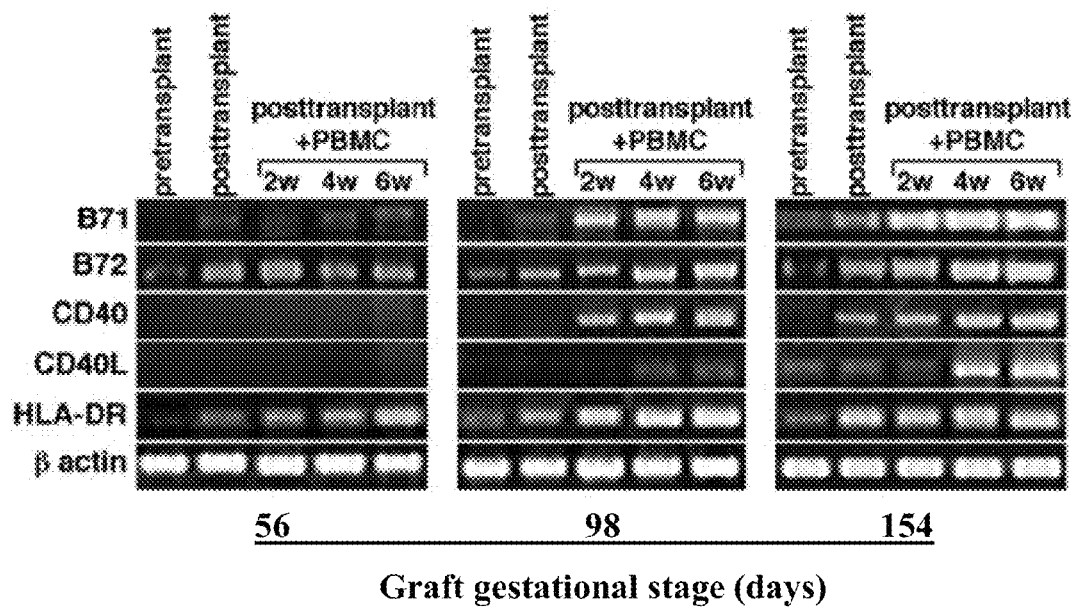

Fig. 13a  Fig. 13b
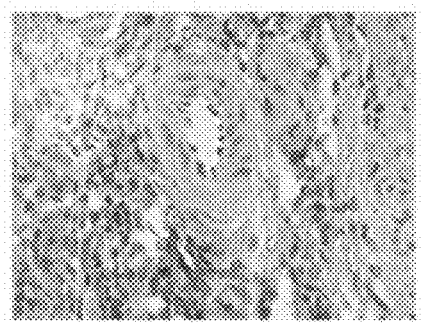 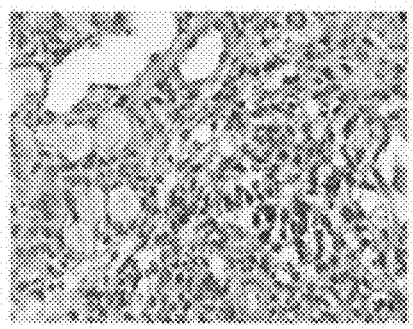
Fig. 13c
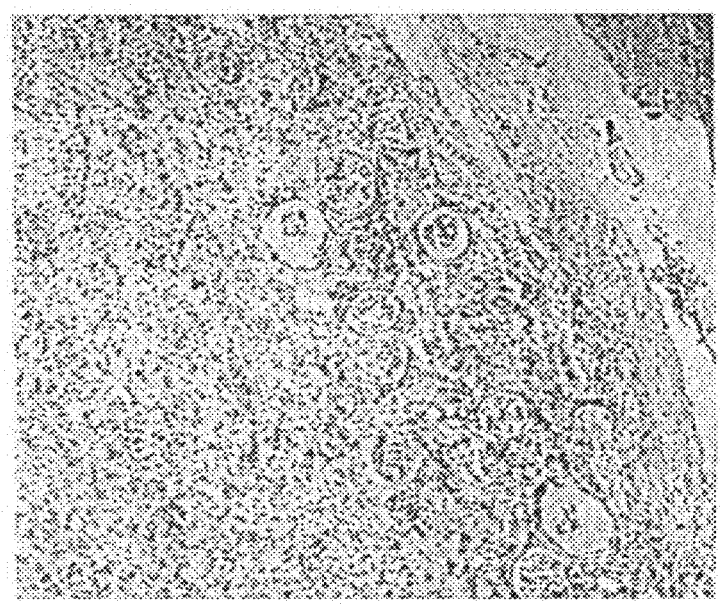
Fig. 14a  Fig. 14b
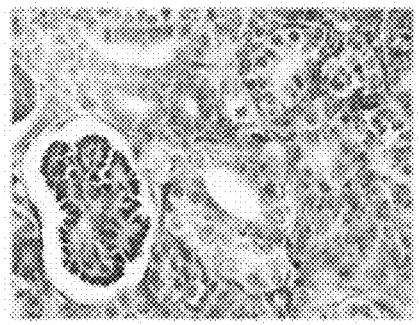 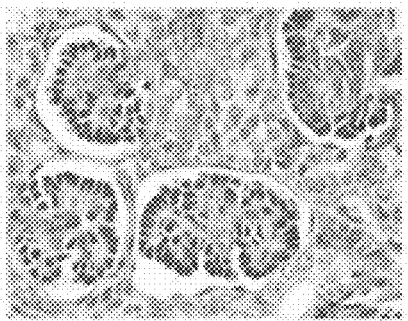

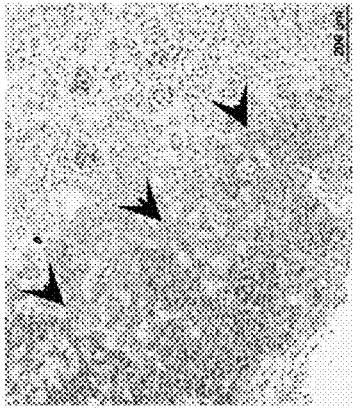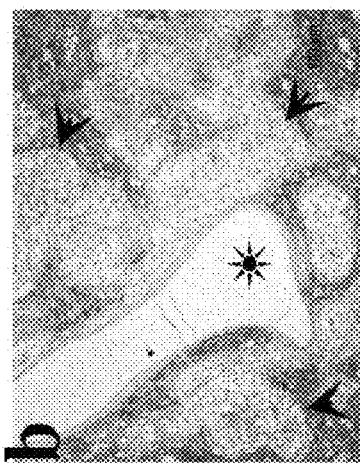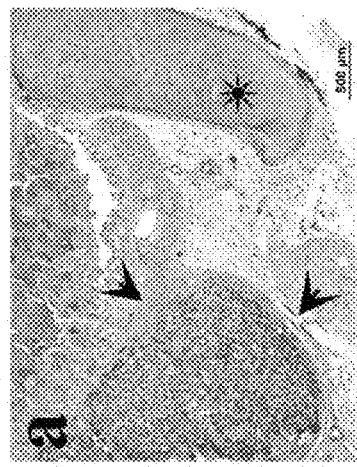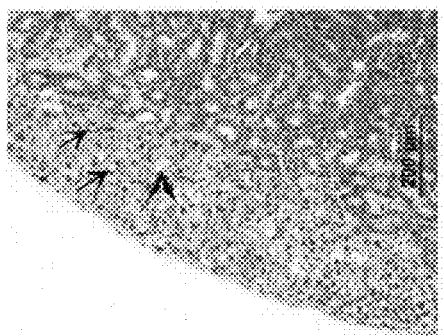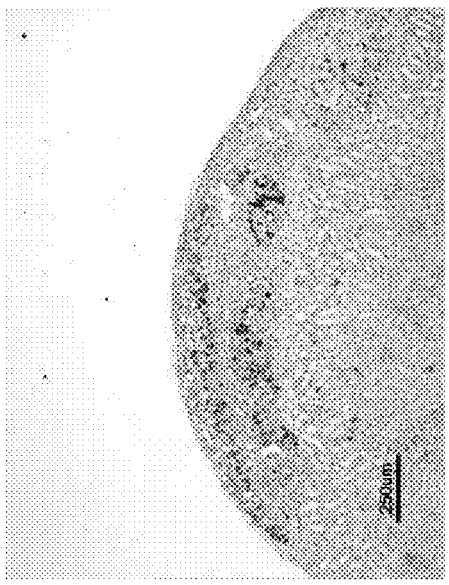

Fig. 24a
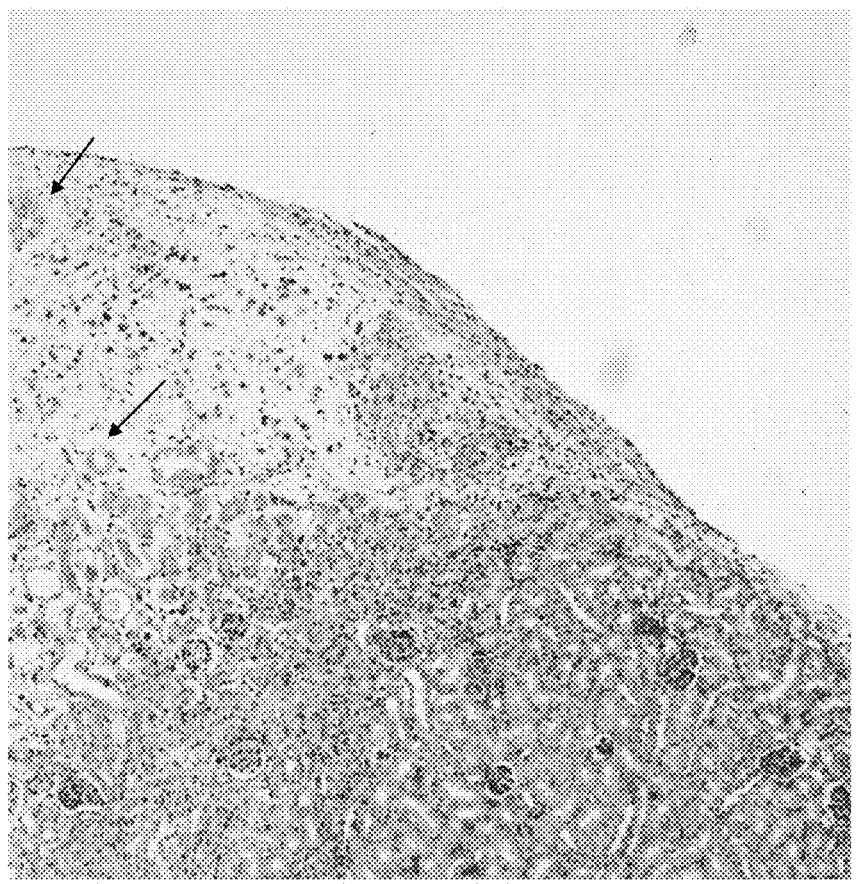
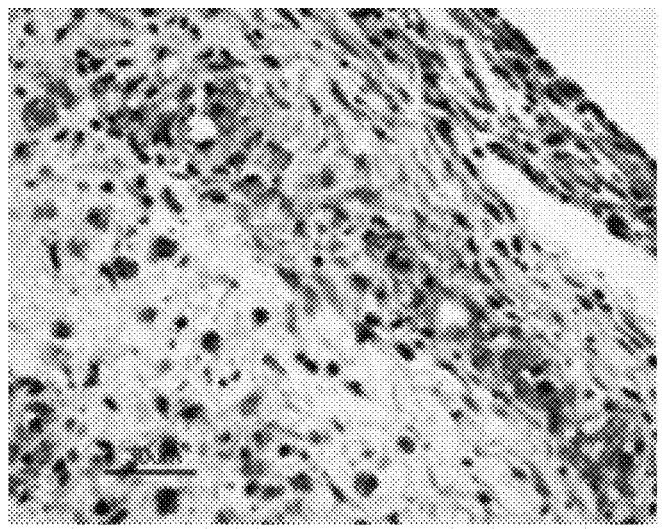
Fig. 24b

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: Single strand DNA primer

<400> SEQUENCE: 1
gaccaaggaa gtgaagtggc                                                 20

<210> SEQ ID NO 2
<211> LENGTH: 24
<212> TYPE: DNA
<213> ORGANISM: Artificial sequence
<220> FEATURE:
<223> OTHER INFORMATION: Single strand DNA primer

<400> SEQUENCE: 2
aggagaggtg aggctctgga aaac                                            24

<210> SEQ ID NO 3
<211> LENGTH: 23
<212> TYPE: DNA
<213> ORGANISM: Artificial sequence
```

```
<220> FEATURE:
<223> OTHER INFORMATION: Single strand DNA primer

<400> SEQUENCE: 3
cactatggga ctgagtaaca ttc                                          23

<210> SEQ ID NO 4
<211> LENGTH: 23
<212> TYPE: DNA
<213> ORGANISM: Artificial sequence
<220> FEATURE:
<223> OTHER INFORMATION: Single strand DNA primer

<400> SEQUENCE: 4
gcactgacag ttcagaattc atc                                          23

<210> SEQ ID NO 5
<211> LENGTH: 22
<212> TYPE: DNA
<213> ORGANISM: Artificial sequence
<220> FEATURE:
<223> OTHER INFORMATION: Single strand DNA primer

<400> SEQUENCE: 5
ctctgcagtg cgtcctctgg gg                                           22

<210> SEQ ID NO 6
<211> LENGTH: 24
<212> TYPE: DNA
<213> ORGANISM: Artificial sequence
<220> FEATURE:
<223> OTHER INFORMATION: Single strand DNA primer

<400> SEQUENCE: 6
gatggtatca gaaacccctg tagc                                         24

<210> SEQ ID NO 7
<211> LENGTH: 24
<212> TYPE: DNA
<213> ORGANISM: Artificial sequence
<220> FEATURE:
<223> OTHER INFORMATION: Single strand DNA primer

<400> SEQUENCE: 7
tatcacccag atgattgggt cagc                                         24

<210> SEQ ID NO 8
<211> LENGTH: 24
<212> TYPE: DNA
<213> ORGANISM: Artificial sequence
<220> FEATURE:
<223> OTHER INFORMATION: Single strand DNA primer

<400> SEQUENCE: 8
ccagggttac caagttgttg ctca                                         24

<210> SEQ ID NO 9
<211> LENGTH: 22
<212> TYPE: DNA
<213> ORGANISM: Artificial sequence
<220> FEATURE:
<223> OTHER INFORMATION: Single strand DNA primer

<400> SEQUENCE: 9
atgaaggtct ccgcggcagc cc                                           22
```

```
<210> SEQ ID NO 10
<211> LENGTH: 22
<212> TYPE: DNA
<213> ORGANISM: Artificial sequence
<220> FEATURE:
<223> OTHER INFORMATION: Single strand DNA primer

<400> SEQUENCE: 10
ctagctcatc tccaaagagt tg                                              22

<210> SEQ ID NO 11
<211> LENGTH: 22
<212> TYPE: DNA
<213> ORGANISM: Artificial sequence
<220> FEATURE:
<223> OTHER INFORMATION: Single strand DNA primer

<400> SEQUENCE: 11
accatcaagc tctgcgtgac tg                                              22

<210> SEQ ID NO 12
<211> LENGTH: 23
<212> TYPE: DNA
<213> ORGANISM: Artificial sequence
<220> FEATURE:
<223> OTHER INFORMATION: Single strand DNA primer

<400> SEQUENCE: 12
gcaggtcagt tcagttccag gtc                                             23
```

THERAPEUTIC TRANSPLANTATION USING DEVELOPING, HUMAN OR PORCINE, RENAL OR HEPATIC, GRAFTS

RELATED APPLICATIONS

This application is a divisional of U.S. patent application Ser. No. 11/037,025 filed Jan. 19, 2005, which is a continuation-in-part of U.S. patent application Ser. No. 10/759,033 filed Jan. 20, 2004, now abandoned, which is a continuation-in-part of U.S. patent application Ser. No. 10/379,725 filed Mar. 6, 2003, now abandoned, which is a continuation-in-part of PCT Patent Application No. PCT/IL02/00722 filed Sep. 1, 2002, which is a continuation-in-part of U.S. patent application Ser. No. 10/118,933 filed Apr. 10, 2002, now abandoned, which claims the benefit of priority from U.S. Provisional Patent Application No. 60/317,452 filed Sep. 7, 2001.

The contents of the above applications are incorporated herein by reference in their entirety.

FIELD AND BACKGROUND OF THE INVENTION

The present invention relates to methods of treating disorders by transplantation of grafts derived from developing, non-syngeneic, renal or hepatic, organs/tissues. More particularly, the present invention relates to methods of treating in humans renal disorders via transplantation of porcine 27- to 28-day gestational stage renal grafts, or of allogeneic human 42- to 56-day gestational stage renal grafts. The present invention further particularly relates to methods of treating in humans disorders amenable to treatment via hepatic transplantation using transplantation of porcine 28-day gestational stage hepatic grafts, or of allogeneic human 7-week gestational stage hepatic grafts.

Transplantation of fully differentiated allogeneic kidneys is a widely practiced, life-saving, medical procedure of choice for treatment of numerous highly debilitating and/or lethal renal disorders of major clinical impact. These include major diseases such as renal complications resulting from diabetes or hypertension, cystic kidney disease, obstructive nephropathy and glomerulonephritis. More than 10,000 kidney transplants are performed each year in the United States on patients with end-stage renal disease, at an annual cost estimated to be in excess of $15 billion.

Transplantation of fully differentiated allogeneic hepatic grafts is a widely practiced, life-saving, medical procedure of choice for treatment of numerous highly debilitating and/or lethal hepatic disorders, or enzyme-deficiency disorders of major clinical impact. Disorders amenable to therapy via hepatic transplantation include such major diseases as cirrhosis, viral hepatitis, and hepatocellular carcinoma. In numerous instances of such disorders, restoration of normal liver function is vital for the survival of affected individuals. The liver is the second most commonly transplanted major organ after the kidney. According to the latest U.S. Centers for Disease Control and Prevention sources, cirrhosis remains the 12th leading cause of death for adults in the United States, with 26,225 deaths reported in 1999 and a death rate of nearly 10 cases per 100,000 persons. This accounts for 1.1 percent of total deaths. Furthermore, this number may grossly underestimate the real impact of end-stage liver disease because it does not include acute liver failure or other etiologies that may lead to the need for liver transplantation. Currently, more than 17,000 people in the United States are waiting for liver transplants. According to the United Network for Organ Sharing (UNOS), about 5,300 liver transplantations were performed in the United States in 2002. Hepatocellular carcinoma is the fifth most common malignant disorder and causes nearly 1 million deaths a year worldwide. Other diseases amenable to treatment via hepatic transplantation include various types of deficiencies in enzymes which can be produced by hepatic tissues, such as clotting factor deficiencies resulting in hemophilia.

Allograft transplantation is a therapeutic modality which is associated with critical disadvantages. Standard therapeutic transplantation of renal or hepatic allografts requires obtainment of donor derived grafts which are immunologically, as well as morphologically, matched with the graft recipient. However, the criteria for such matching, particularly the immunological matching, are highly stringent and difficult to fulfill. As such, allografts which are suitably matched to prospective recipients are, in numerous cases, simply unavailable. Thus, large numbers of patients who would otherwise benefit from therapeutic allograft transplantation succumb to diseases associated with organ failure, while awaiting matched transplant donors. In the case of kidney transplantation, approximately eight to nine patients die every day while waiting for a transplant due to the shortage of donors. While each year in the United States, there are an estimated 25,000 potential donors who die, of this number, only about 5,000 have made arrangements to donate their organs. In 1996, of the 10,017 kidneys recovered for transplant, 12 percent failed to meet the donor criteria for transplantation. For example, the average waiting period for obtaining a suitable cadaveric kidney may be more than two years, and only 15 to 20 percent of patients waiting for a transplant receive them. However, even following optimally successful allograft transplantation, permanent and daily administration of toxic doses of immunosuppressive drugs such as cyclosporin A is mandatory to prevent graft rejection. Administration of drugs such as cyclosporin A is highly undesirable since such drugs are associated with severe side-effects, including carcinogenicity, nephrotoxicity, and lead to increased susceptibility to opportunistic infections. Such immunosuppressive regimens are furthermore often unsuccessful in preventing allograft rejection in the medium term, and in any case generally cannot indefinitely prevent graft rejection in the long term. Current allograft transplantation methods are generally performed by harvesting allografts from living human donors, thus requiring subjecting healthy human donors to organ loss via potentially fatal major surgery. While cadaveric graft donors are widely employed, their use presents ethical dilemmas for donor family members as well as for recipients, and is associated with lower success rates than use of living donors. As a last resort back-up alternative to renal transplantation, permanent hemodialysis can be used to sustain life in the case of kidney failure, however this procedure is highly debilitating, cumbersome, expensive, of limited effectiveness, and is associated with a significant risk of opportunistic infections.

The use of xenografts, in particular porcine xenografts has been proposed as a means to overcome the shortage of available human organs for transplantation. Porcine grafts are widely considered to be the ideal animal alternative to human grafts for therapeutic transplantation in humans due to their morphological compatibility with the human anatomy, and due to their essentially unlimited supply which would overcome the restricted availability impediment inherent to prior art human grafts (Auchincloss, H. and Sachs, D. H., 1998. Annu. Rev. Immunol. 16, 433-470). The use of such animal grafts would present the advantage of circumventing the medical/ethical burdens of harvesting grafts from human donors. However, to date no methods of xenograft transplantation have been devised which are capable of overcoming the rapid and vigorous immune rejection of xenografts by the host immune system following transplantation.

Thus, novel and optimal methods of therapeutic renal or hepatic allograft/xenograft transplantation which overcome the limitations of the prior art are urgently required.

It has been known for over four decades that grafts derived from developing organs/tissues are less immunogenic following transplantation into non-syngeneic hosts than grafts derived from corresponding fully differentiated organs/tissues (Medawar, P. B., 1953. Symp. Soc. Exp. Biol. 7, 320-323). Subsequent studies, such as those using a human to rat xenogeneic renal transplantation model (Dekel B. et al., 1997. Transplantation 64, 1550; Dekel B. et al., 2000. Transplantation 69, 1470), or an allogeneic rat renal transplantation model (Hammerman M R., 2000. Pediatr Nephrol. 14, 513) have confirmed these observations. Various mechanisms have been suggested to explain the reduced immunogenicity of developing tissue grafts. It has been suggested that such developing tissue-derived grafts induce attenuated host anti-graft immune responses compared to adult stage tissue-derived grafts due to the former being predominantly vascularized by host-derived vasculature, as opposed to the predominantly graft-derived graft vascularization observed in the latter (Hyink D. P. et al., 1996. Am J. Physiol. 270, F886). It has further been suggested that the low levels of major histocompatibility (MHC) and adhesion molecule expression, and of antigen presenting cells in gestational stage tissue grafts decreases the capacity of such grafts to activate host immune responses.

Thus, a potentially optimal strategy for performing therapeutic organ transplantation in humans would be to use grafts derived from developing allogeneic human, or from developing xenogeneic porcine organs/tissues. As well as having potentially optimally low immunogenicity, such grafts would potentially provide the further advantage of inherently possessing optimal growth and differentiation potentials relative to those derived from fully differentiated organs/tissues. As such, such developing organ/tissue grafts may have optimal capacity, following transplantation into a recipient, for generating graft-derived organs/tissues which are morphologically and functionally integrated with the recipient.

In the developing human kidney, fresh stem cells are induced into the nephrogenic pathway to form nephrons until 34 weeks (238 days) of gestation. Such nephrogenic differentiation pathway involves invasion of a specialized region of intermediate mesoderm by an epithelial source (ureteric bud), which grows and branches to form a collecting duct system, and induces disorganized metarenal mesenchymal stem cells to group and differentiate into nephrons [Woolf, A. S. in: Pediatric Nephrology, 4th ed. Barratt, T. M., Avner, A. and Harmon, W. (eds.), Williams & Wilkins, Baltimore, Md. pp. 1-19 (1999)].

Various approaches for using grafts derived from non-fully differentiated sources have been suggested or attempted in the prior art.

One general embryonic stem (ES) cell approach involves culturing human ES cells, which are pluripotent, so as to produce cell types/tissues of a desired embryonic germ layer, and to employ such cells/tissues as therapeutic grafts (Thomson J A. et al., 1998. Science. 282:1145-7; Reubinoff B E. et al., 2000. Nat. Biotechnol. 18:399-404). This approach, however, has failed to provide renal or hepatic grafts suitable for therapeutic transplantation. Furthermore, it was found that transplantation of cultured ES cell grafts into immunocompromised mouse hosts generate teratomas (Reubinoff B E. et al., 2000. Nat. Biotechnol. 18:399-404), a highly undesirable potentially harmful consequence in the therapeutic transplantation context.

One ES cell/hepatic approach involves genetically modifying mouse ES cell lines to express hepatocyte nuclear factor (HNF)-3beta (Ishizaka S. et al., 2002. FASEB J 16, 1444-1446) so as to generate cultured ES cell-derived hepatocytes for transplantation.

Another ES cell/hepatic approach involves selecting for transplantation hepatocytes from cultured ES cells genetically modified with a gene trap vector insertion into an ankyrin repeat-containing gene providing a beta-galactosidase marker of early differentiation of hepatocytes in-vitro (Jones E A. et al., 2002. Exp Cell Res. 272, 15-22).

The prior art ES cell/hepatic approaches, however, not attempted transplantation of such cultured ES cell-derived hepatocyte grafts in a host, and have therefore failed to demonstrate that following transplantation into a non-syngeneic host, such grafts will be well tolerated by the host, will not generate teratomas/undesired lineages, and/or will provide hepatic functionality.

Various prior art approaches have been proposed for using grafts derived from developing kidneys for performing non-syngeneic renal transplantation.

One renal/allogeneic approach involves transplantation of rat 15-day gestational stage renal grafts under the renal capsule or into the omentum of rat hosts (Rogers, S. A. et al., 1998. Kidney Int. 54, 27-37; Rogers, S. A. et al., 2001. Am. J. Physiol. Regul. Integr. Comp. Physiol. 280, R132-136; Rogers, S. A. and Hammerman, M. R., 2001. Am. J. Physiol. Regul. Integr. Comp. Physiol. 281, R661-665; U.S. Pat. No. 5,976,524 to Hammerman).

Another renal/allogeneic approach involves transplantation of rat 15- or 17-day gestational stage renal grafts into the anterior eye chamber or under the kidney capsule of allogeneic adult rat hosts. While such transplanted grafts became vascularized and displayed renal differentiation after 9-10 posttransplantation, by 16 days posttransplantation they exhibited obvious signs of graft rejection, including generation of hypercellular glomeruli and lymphocytic infiltration in peritubular spaces (Abrahamson et al., 1991. Lab. Invest 64:629-639).

A further renal/allogeneic approach involves transplantation of mouse 12-day gestational stage renal grafts previously subjected to multi-day organ culture into the anterior eye chamber or renal cortex of allogeneic newborn or adult recipients (Robert et al., 1996. Am. J. Physiol. 271:F744-F753). In this approach, by 7 days posttransplantation, grafts implanted in both newborn and adult hosts had a vascular component which was significantly of host origin, a factor which strongly correlates with eventual graft rejection.

An additional renal/allogeneic approach involves transplantation of sections of rat 1-day old neonatal or 15- to 17-day gestational stage renal grafts into related or unrelated allogeneic recipients. However, following transplantation, lymphocytic infiltration of grafts and replacement of the grafts by fibrosis occurred in both related and unrelated adult hosts, and was more rapid in the unrelated hosts (Barakat and Harrison, 1971. J. Anat. 110:393-407).

One renal/xenogeneic approach involves transplantation of rat 15-day gestational stage renal grafts into the omentum of mouse hosts subjected to CTLA4-Ig costimulation blockade for prevention of graft rejection (Rogers, S. A. and Hammerman, M. R., 2001. Am. J. Physiol. Regul. Integr. Comp. Physiol. 280, R1865-1869).

Another renal/xenogeneic approach involves transplantation of human 98- to 154-day gestational stage renal grafts into chimeric rats bearing human PBMCs (Dekel B. et al., 1997. Transplantation 64, 1550), or transplantation of human 70-day gestational stage renal grafts into immune deficient mice (Dekel B. et al., 2000. Transplantation 69, 1470).

A further renal/xenogeneic approach suggests transplantation of "approximately" 20- to 30-day gestational stage porcine renal grafts (U.S. Pat. No. 5,976,524 to Hammerman). This approach, however, is highly speculative by virtue of never having been experimentally tested, and therefore fails to demonstrate that, following transplantation into a non-syngeneic host, grafts at such gestational stages will be well tolerated by the host, will generate developed, functional renal organs/tissues, and will not generate teratomas/undesired non-renal lineages.

Various prior art approaches have been proposed for using grafts derived from developing liver for performing non-syngeneic hepatic transplantation.

One hepatic/xenogeneic approach involves transplantation of embryonic porcine hepatocytes into the spleen of immune deficient rats (Kokudo N. et al., 1996. Cell Transplantation 5:S21-2). In these experiments, hepatic function in graft recipients was analyzed at four weeks posttransplantation.

Another hepatic/xenogeneic approach involves transplantation of porcine fetal liver fragments enclosed in microporous immunoisolation capsules into the omentum of rat recipients having acute hepatic failure (Takebe K. et al., 1996. Cell Transplant 5:S31-3). Such transplantation, however, was found to be associated with an unacceptably high death rate in graft recipients.

A further hepatic/xenogeneic approach involves transplantation of fetal or neonatal porcine liver fragments enclosed in microporous immunoisolation capsules into dog recipients having hepatic failure (Kanai N. et al., 1999. Cell Transplantation 8:413-7). In these studies the grafts were examined histologically 14 days posttransplantation.

An additional hepatic/xenogeneic approach involves transplantation of porcine very late-stage fetal liver tissue into dogs (Kanai N. et al., 1999. Transplant Immunology 7:95-9). In these experiments, hyperacute graft rejection was only delayed, as compared to that occurring following transplantation of adult-stage grafts, but not prevented.

One hepatic/allogeneic approach involves transplantation of rat fetal liver into the spleen of rats subjected to FK506 immunosuppression (Kokudo N. et al., 1996. Cell Transplantation 5:S21-2). These studies suggested that immunosuppressive recipient treatment was required for achieving engraftment until four weeks posttransplantation.

All such prior art approaches involving use of grafts derived from developing kidney or liver have significant disadvantages, including: undemonstrated or suboptimal short- and/or long-term immune tolerance by graft hosts, and/or requirement for graft host immunosuppressive treatment; undemonstrated or suboptimal short- or long-term structural and functional graft differentiation into functional renal or hepatic organs; predominantly graft-derived, as opposed to host-derived, graft vascularization following transplantation, the former strongly correlating with risk of eventual graft rejection; inadequate availability of transplantable grafts; failure to demonstrate that the grafts employed are at a sufficiently advanced developmental stage to avoid teratoma/undesired tissue lineage differentiation following transplantation, and hence failure to demonstrate safety for therapeutic applications. Xenogeneic approaches involving non-porcine organ grafts fail to provide grafts which can be transplanted in humans. Approaches involving encapsulated hepatic grafts fail to provide hepatic grafts capable of providing any of the numerous critical hepatic functions requiring free contact between the liver and circulating cells/particles.

Thus, all prior art approaches have failed to provide an adequate solution for using transplantation of developing non-syngeneic renal or hepatic grafts to treat human disorders amenable to treatment via transplantation of such grafts.

There is thus a widely recognized need for, and it would be highly advantageous to have, a method of treating human disorders via transplantation of non-syngeneic developing renal or hepatic grafts devoid of the above limitation.

SUMMARY OF THE INVENTION

According to one aspect of the present invention there is provided a method of treating a renal disorder in a subject in need thereof, the method comprising transplanting renal tissue into the subject, the renal tissue being derived from a human kidney being at a stage of development selected from a range of 48 to 57 days of gestation, thereby treating the renal disorder in the subject.

According to further features in preferred embodiments of the invention described below, the human kidney is at a stage of development selected from a range of 49 to 56 days of gestation.

According to still further features in the described preferred embodiments, the human kidney is non-syngeneic with the subject.

According to still further features in the described preferred embodiments, the human kidney is allogeneic with the subject.

According to another aspect of the present invention there is provided a method of treating a renal disorder in a subject in need thereof, the method comprising transplanting renal tissue into the subject, the renal tissue being derived from a porcine kidney being at a stage of development selected from a range of 26 to 29 days of gestation, thereby treating the renal disorder in the subject.

According to further features in preferred embodiments of the invention described below, the porcine kidney is at a stage of development selected from a range of 27 to 28 days of gestation.

According to still further features in the described preferred embodiments, the porcine kidney is non-syngeneic with the subject.

According to still further features in the described preferred embodiments, the porcine kidney is xenogeneic with the subject.

According to still further features in the described preferred embodiments, transplanting the renal tissue into the subject is effected by transplanting the renal tissue into an anatomical location of the subject selected from the group consisting of the renal capsule, the kidney, the omentum, the intra-abdominal space, and an intestinal loop.

According to still further features in the described preferred embodiments, the renal tissue is a whole metanephros.

According to still further features in the described preferred embodiments, the renal tissue is a partial metanephros.

According to yet another aspect of the present invention there is provided a method of treating a hepatic or enzyme-deficiency disorder in a subject in need thereof, the method comprising transplanting hepatic tissue into the subject, the hepatic tissue being derived from a porcine liver being at a stage of development selected from 25 to 56 days of gestation.

According to further features in preferred embodiments of the invention described below, the porcine liver is at a stage of development selected from a range of 26 to 56 days of gestation.

According to further features in preferred embodiments of the invention described below, the porcine liver is at a stage of development selected from a range of 27 to 56 days of gestation.

According to further features in preferred embodiments of the invention described below, the porcine liver is at a stage of development selected from a range of 28 to 56 days of gestation.

According to further features in preferred embodiments of the invention described below, the porcine liver is at a stage of development selected from a range of 28 to 42 days of gestation.

According to further features in preferred embodiments of the invention described below, the porcine liver is at a stage of development selected from a range of 27 to 29 days of gestation.

According to further features in preferred embodiments of the invention described below, the porcine liver is at a stage of development of 28 days of gestation.

According to still further features in the described preferred embodiments, the porcine liver is non-syngeneic with the subject.

According to still further features in the described preferred embodiments, the porcine liver is xenogeneic with the subject.

According to still another aspect of the present invention there is provided a method of treating a hepatic or enzyme-deficiency disorder in a subject in need thereof, the method comprising transplanting hepatic tissue into the subject, the hepatic tissue being derived from a human liver being at a stage of development selected from a range of 6 to 14 weeks of gestation, thereby treating the hepatic or enzyme-deficiency disorder in the subject.

According to further features in preferred embodiments of the invention described below, the human liver is at a stage of development selected from a range of 6 to 12 weeks of gestation.

According to still further features in the described preferred embodiments, the human liver is at a stage of development selected from a range of 6 to 10 weeks of gestation.

According to still further features in the described preferred embodiments, the human liver is at a stage of development selected from a range of 6 to 9 weeks of gestation.

According to still further features in the described preferred embodiments, the human liver is at a stage of development selected from a range of 6 to 8 weeks of gestation.

According to still further features in the described preferred embodiments, the human liver is at a stage of development of 7 weeks of gestation.

According to still further features in the described preferred embodiments, the human liver is non-syngeneic with the subject.

According to still further features in the described preferred embodiments, the human liver is allogeneic with the subject.

According to still further features in the described preferred embodiments, transplanting the hepatic tissue into the subject is effected by transplanting the hepatic tissue into an anatomical location of the subject selected from the group consisting of the portal vein, the liver, the renal capsule, the sub-cutis, the omentum, the spleen, and the intra-abdominal space.

According to still further features in the described preferred embodiments, the subject is a mammal.

According to still further features in the described preferred embodiments, the subject is a human.

According to still further features in the described preferred embodiments, the treatment method further comprises treating the subject with an immunosuppressive regimen prior to, concomitantly with or following the transplanting the renal tissue into the subject, thereby promoting engraftment of the tissue in the subject.

According to still further features in the described preferred embodiments, treating the subject with an immunosuppressive regimen is effected by administering at least one immunosuppressant drug to the subject.

According to still further features in the described preferred embodiments, the at least one immunosuppressant drug is capable of blocking binding of a lymphocyte coreceptor with a ligand of the lymphocyte coreceptor.

According to still further features in the described preferred embodiments, the at least one immunosuppressant drug is capable of blocking binding of a lymphocyte coreceptor with a ligand of the lymphocyte coreceptor, and administering the at least one immunosuppressant drug to the subject is effected during a time period selected from a range of 1 to 60 days.

According to still further features in the described preferred embodiments, the lymphocyte coreceptor is selected from the group consisting of B7-1, CD40, and CD40L.

According to still further features in the described preferred embodiments, the ligand of the lymphocyte coreceptor is selected from the group consisting of B7-1, CD40, and CD40L.

According to still further features in the described preferred embodiments, the at least one immunosuppressant drug comprises CTLA4-Ig.

According to still further features in the described preferred embodiments, the at least one immunosuppressant drug comprises CTLA4-Ig and anti-CD40L antibody.

According to still further features in the described preferred embodiments, the at least one immunosuppressant drug comprises CTLA4-Ig, anti-CD40L antibody and rapamycin.

The present invention successfully addresses the shortcomings of the presently known configurations by providing a method of transplanting into a non-syngeneic human recipient grafts derived from porcine or human developing kidney or liver so as to generate in the recipient, without risk of teratoma formation, graft-derived renal or hepatic organs/tissues, respectively, which display optimal structural and functional differentiation, and which are well tolerated by the graft recipient without, or with minimal immunosuppression of the graft recipient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
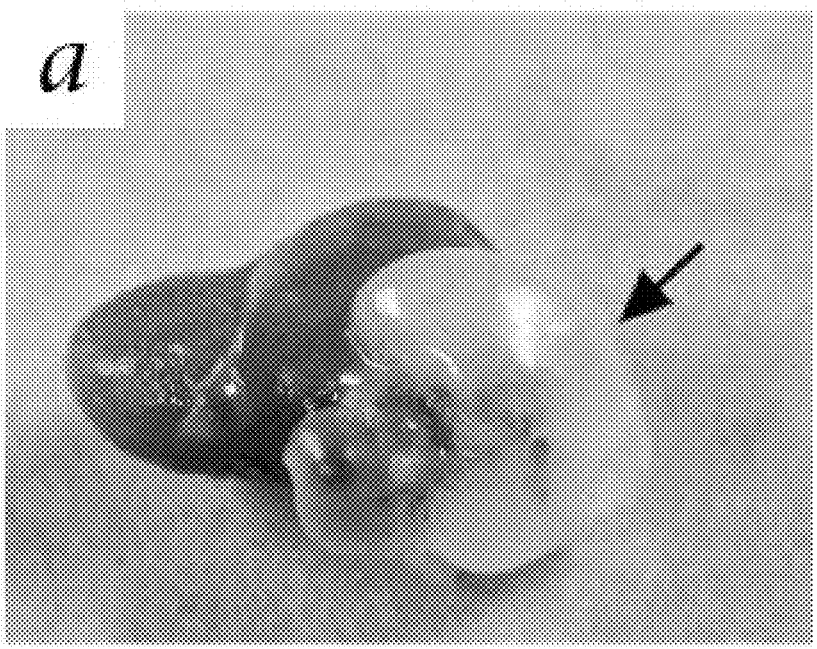
Figure 1B:
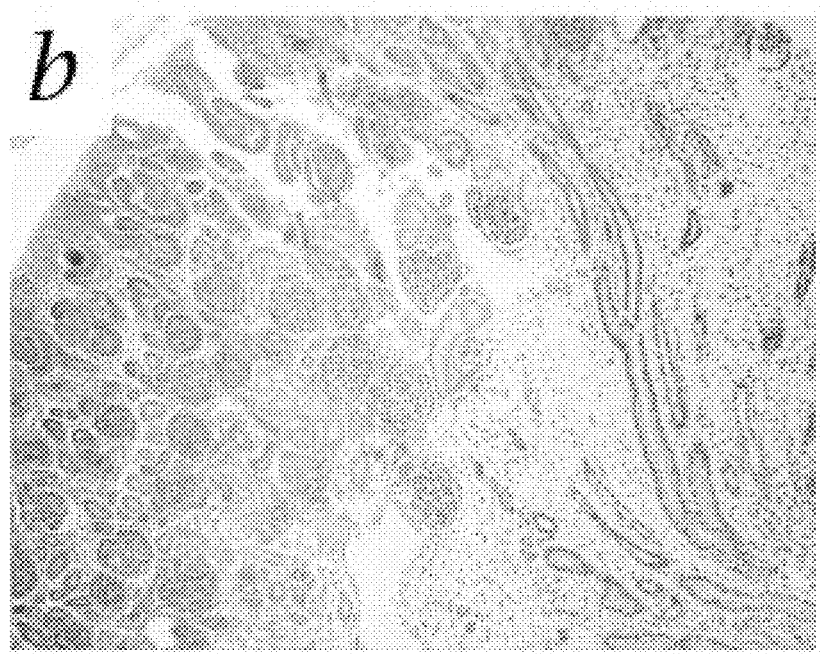

FIGS. 1a-b are photographs depicting significant growth and kidney-specific differentiation of 56-day gestational stage human renal transplanted into immunodeficient mouse hosts. FIG. 1a-b, respectively, depict a macroscopic view and histology (FIG. 1b; H&E; ×10 original magnification) of an 56-day gestational stage human renal tissue graft, 8 weeks posttransplantation. Note massive growth and the formed shape of a kidney (arrow) and appearance of layers of glomeruli and tubuli.

Figure 2A:
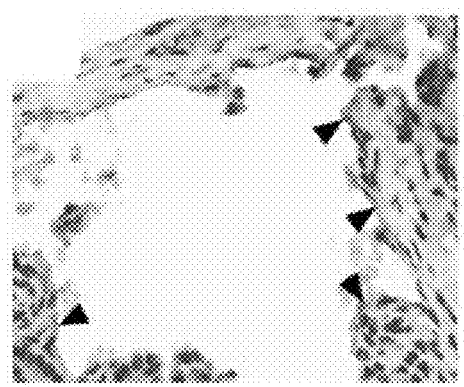
Figure 2B:
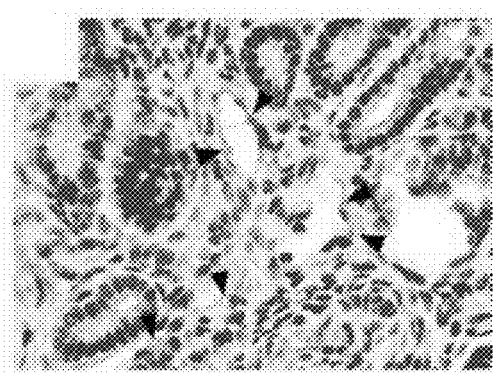
Figure 2C:
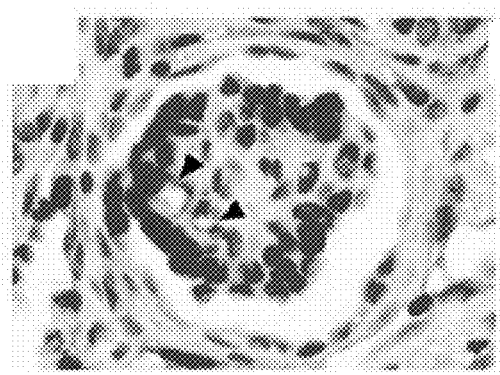
Figure 2D:
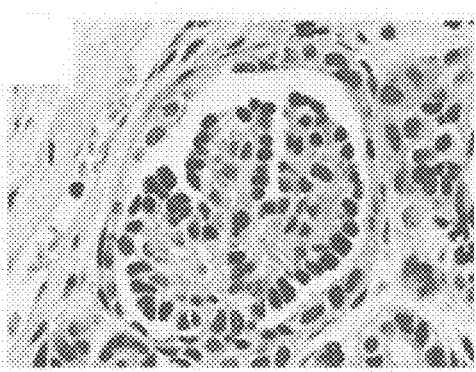
Figure 2E:
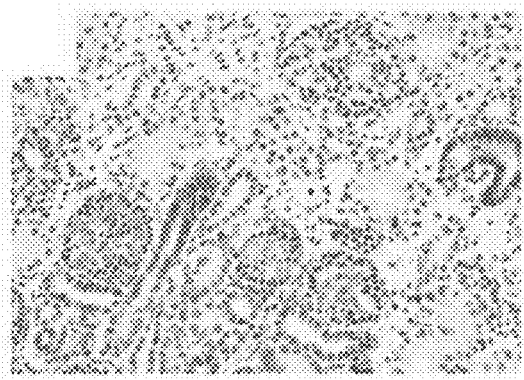

FIGS. 2a-e are photomicrographs depicting host-specific vascularization of human 56-day gestational stage renal grafts following transplantation into immunodeficient mouse hosts. Graft sections were immunostained 4 weeks posttransplantation with anti-mouse CD31 (PECAM) antibody. FIG. 2a depicts all larger vessels staining positive (arrowheads) for mouse CD31. FIG. 2b depicts positive staining (arrowheads) in medium and small-size capillaries. FIG. 2c depicts positive staining (arrowheads) in developing glomeruli. FIG. 2d depicts lack of staining in glomeruli and small-size capillaries in transplants of mature 112-day gestational stage human kidney tissue, 4 weeks posttransplantation. Original magnifications of FIGS. 2a-d are ×40. FIG. 2e depicts lack of positive staining for CD31 in negative control vascularized human fetal kidney (×20 original magnification).

Figure 3:
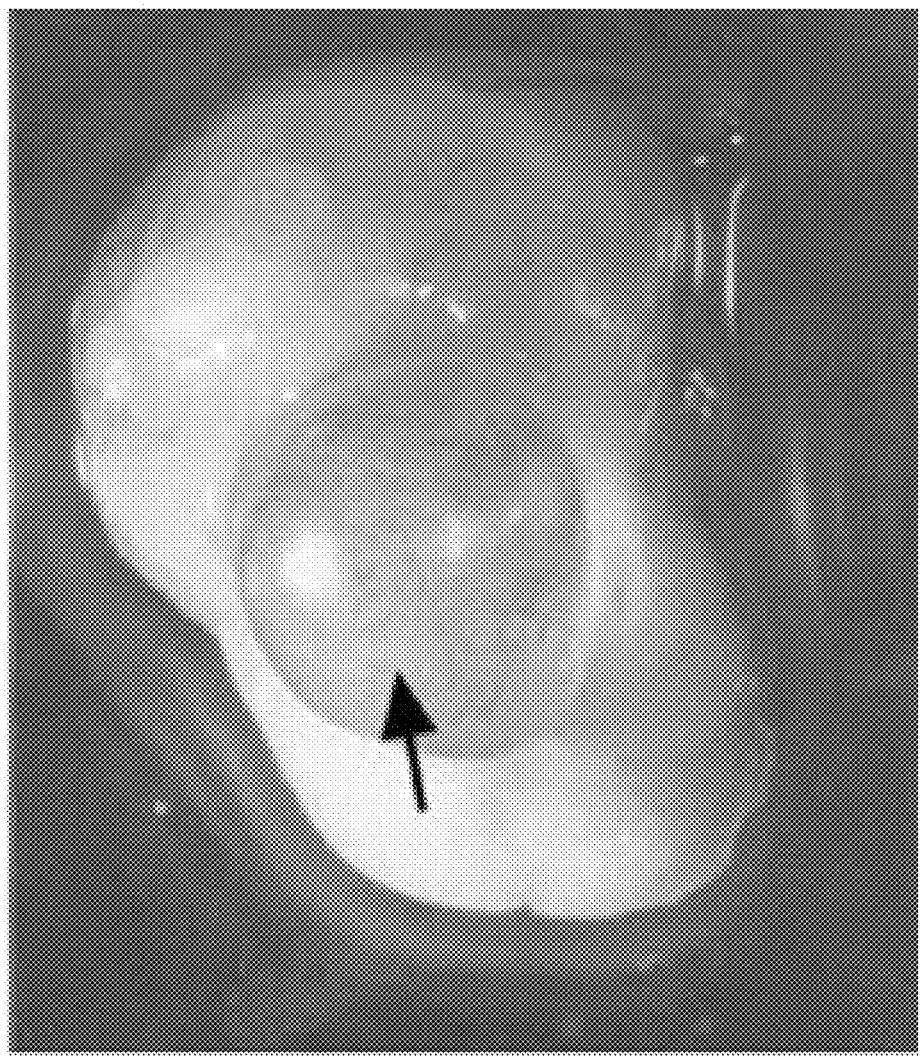

FIG. 3 is a whole-graft photograph depicting generation of large cysts filled with dilute urine generated by human 56-day gestational stage renal grafts transplanted into an immunodeficient host. Shown is a macroscopic view of an intra-abdominal graft containing a large cyst (indicated by arrows), 8 weeks posttransplantation.

FIGS. 4a-d are data plots depicting growth curves of 98-, 70-, 56-, and 49-day gestational stage human renal tissue grafts, respectively, in the presence (closed triangles) or absence (open squares) of alloreactive human PBMCs. In 98- or 70-day gestational stage renal tissue grafts, 8 weeks posttransplantation, P<0.01 and P<0.05 compared with controls, respectively.

Figure 4A:
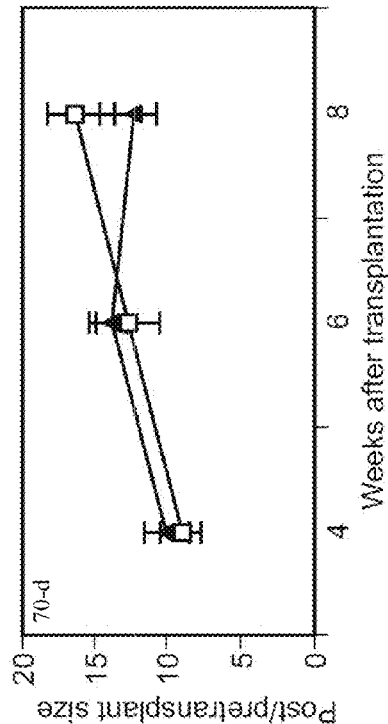
Figure 4B:
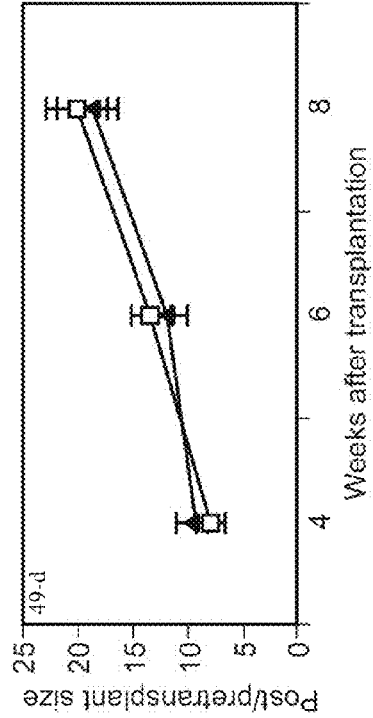
Figure 4C:
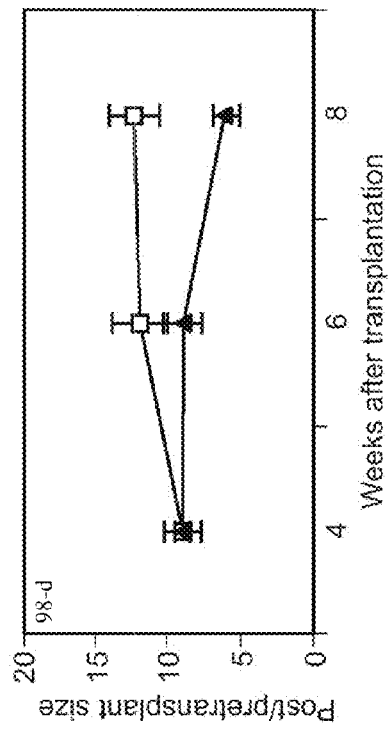
Figure 4D:
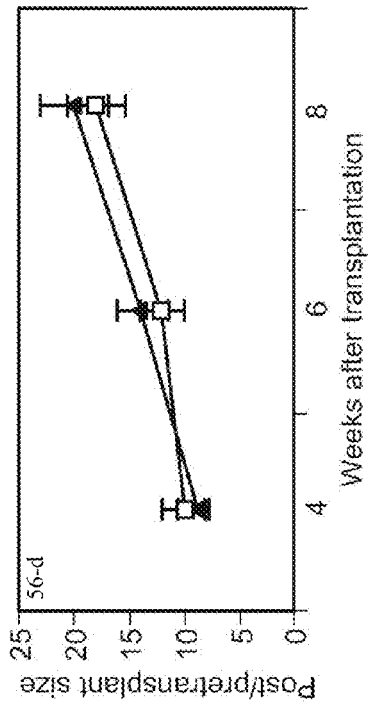
Figures 4E, 4F:
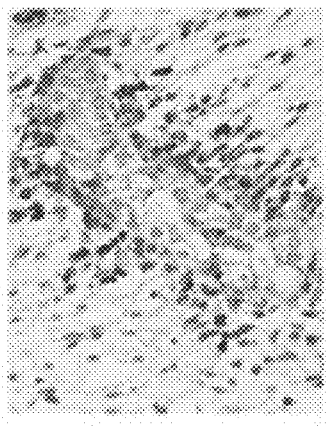

FIGS. 4e-f are photomicrographs depicting a transplant of a 98-day gestational stage human renal tissue graft immunostained with antibodies against human CD3 (×40 original magnification) demonstrating destruction of glomerulus (FIG. 4e) and tubule (FIG. 4f) by human T-lymphocytes.

Figures 4G, 4H:
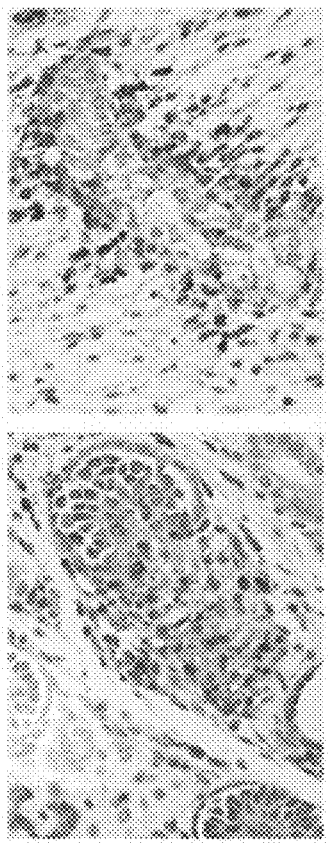

FIGS. 4g-h are photomicrographs depicting an 56-day gestational stage renal tissue-derived transplant immunostained with antibodies specific for human CD3 (×40 original magnification). Note the absence of T-lymphocyte infiltration, and the presence of intact glomeruli and tubuli (FIGS. 4g-h, respectively).

Figure 5A:
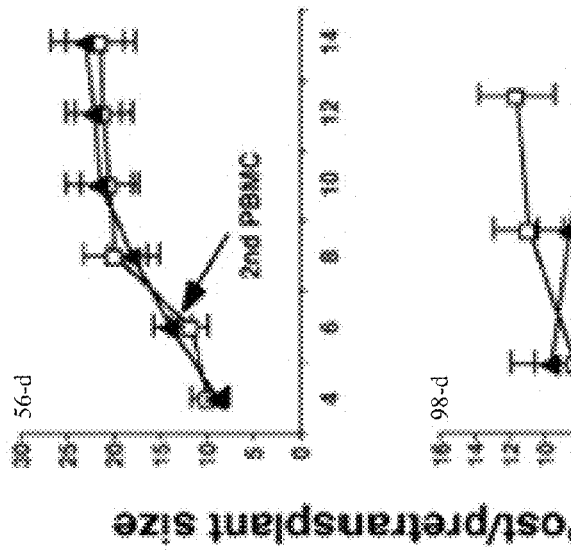
Figure 5B:
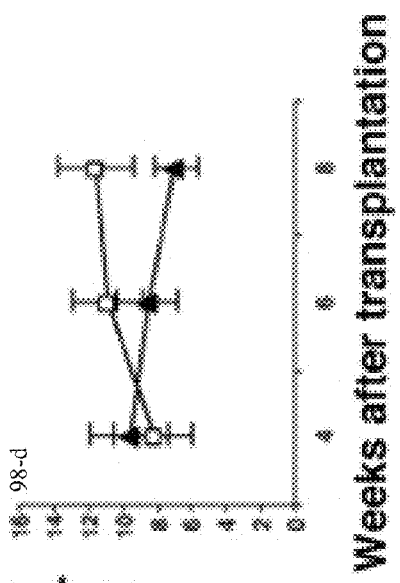

FIGS. 5a-b are data plots depicting similar growth curves of 56-day gestational stage human renal tissue-derived grafts (FIG. 5a) in recipients either receiving two independent infusions of alloreactive human PBMCs at the time of transplantation and 6 weeks post-transplant (closed triangles), or in recipients not infused with PBMCs (open squares). The growth curve of human 98-day gestational stage grafts demonstrates halted growth (FIG. 5b; closed triangles) when the latter are transplanted into recipients concomitantly with the second dose of allogeneic human PBMCs, as compared to those not subjected to PBMC infusion (open squares; P<0.05, 8 weeks posttransplantation).

FIGS. 6a-c are agarose gel electrophoresis UV photographs depicting specific lack of costimulatory molecule transcripts in human 56-day gestational stage renal grafts relative to later stage grafts following transplantation into immunodeficient mouse hosts bearing allogeneic human leukocytes. RT-PCR analysis of costimulatory molecule mRNA expression was performed on normal human developing kidney tissue (pre-transplant), on transplanted human developing renal grafts immediately following transplantation, but prior to administration of alloreactive human PBMCs (post-transplant), and on the developing grafts 2, 4 and 6 weeks following reconstitution of lymphoid-compartment deficient host mice with allogeneic human PBMCs. Transplants analyzed were derived from 56-, 98- and 154-day gestational stage human renal tissues (FIGS. 6a-c, respectively).

Figure 7A:
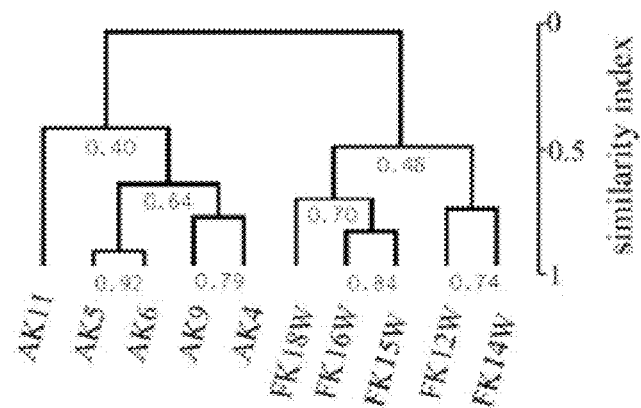
Figure 7B:
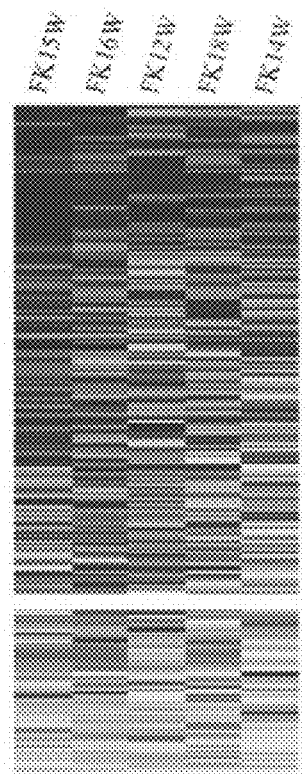
Figure 7C:
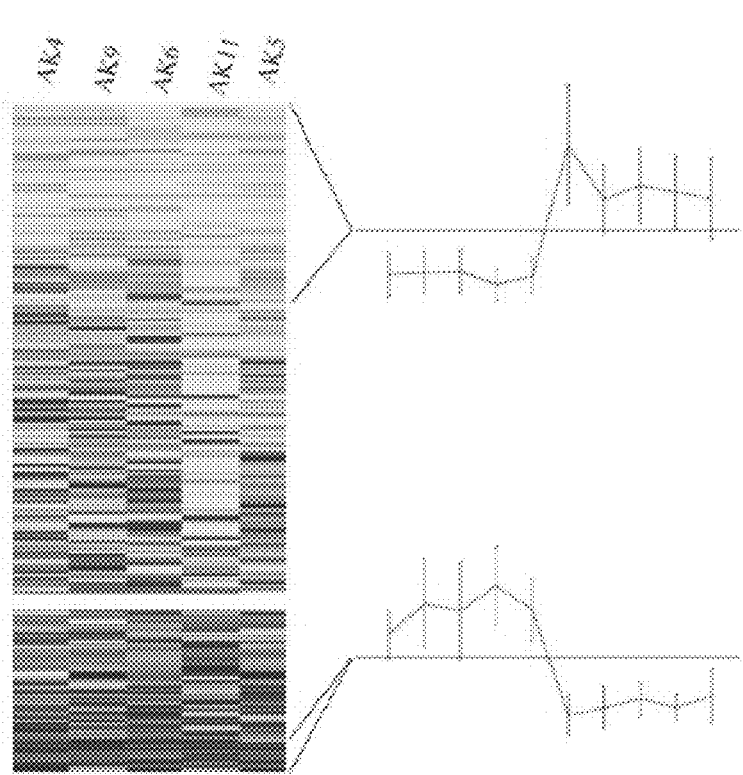

FIGS. 7a-c depict differential gene expression patterns of immunity related genes in normal adult versus gestational stage human renal tissues. FIG. 7a is a hierarchical clustering dendrogram (Zuo, F. et al., 2002. Proc. Natl. Acad. Sci. USA 99, 6292-6297) of the experimental groups generated on the basis of the similarity of their expression profiles depicting that the adult and fetal expression patterns cluster separately. FIG. 7b is a microarray analysis output diagram depicting gene expression patterns in the 231 immunity related genes analyzed showing that 122 of such genes scored a TNoM=0 or 1 (Kaminski, N. and Friedman, N., 2002. Am. J. Respir. Cell Mol. Biol. 27, 125-132). Gene expression values were divided by a geometric mean of all samples, log transformed and then plotted using PLOTTOPGENE software (Kaminski, N. and Friedman, N., 2002. Am. J. Respir. Cell Mol. Biol. 27, 125-132; Zuo, F. et al., 2002. Proc. Natl. Acad. Sci. U.S.A. 99, 6292-6297). Yellow and purple represent maximal and minimal expression, respectively. Note that most of the immunity related genes were expressed at lower levels in gestational stage compared to adult renal tissue. FIG. 7 is a data plot depicting gene expression of 68 genes having TNoM=0 (P<0.05). Plots are the mean expression values of all genes in the group. To eliminate outlier effect, genes were normalized to a range of [0,1], signifying that the maximum value for every gene was set to be 1, the minimum value to be zero, and the rest of the values were linearly fitted to this range. Note again that most statistically significant genes (57/68) were lower in gestational stage as compared to adult stage renal tissue.

Figure 8A:
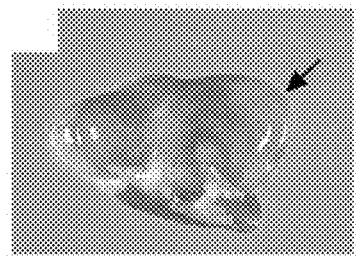
Figure 8B:
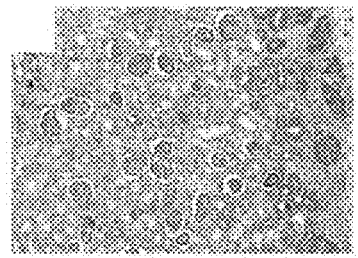
Figure 8C:
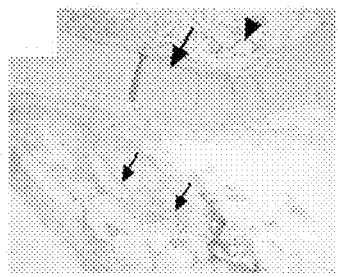
Figure 8D:
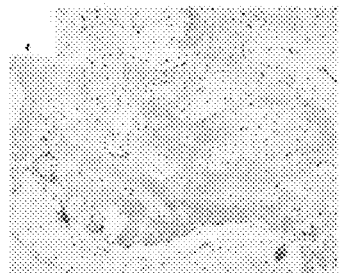
Figure 8E:
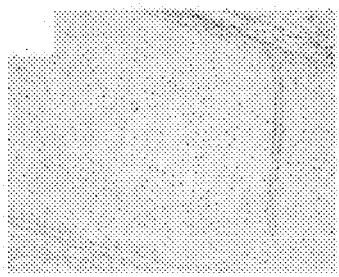
Figure 8F:
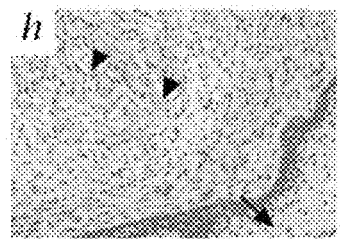
Figure 8G:
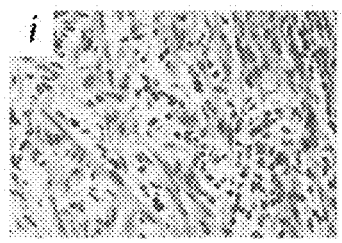
Figure 8H:
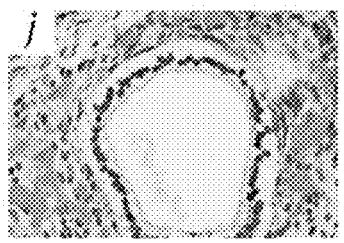

FIGS. 8a-h are photographs depicting optimal growth and renal differentiation by developing porcine renal grafts at a gestational stage of 27-28 days, following transplantation into immunodeficient mice. FIGS. 8a-b are a macroscopic view and a histological photomicrograph (H&E; ×10 original magnification), respectively, of a porcine 28-day gestational stage renal graft, 8 weeks posttransplantation. Note massive growth (arrow) and external vascular beds and numerous glomeruli and tubuli. FIGS. 8c-e depict 20- to 21-day gestational stage grafts. FIG. 8c is a ×4 original magnification H&E histology photomicrograph showing blood vessels (arrowhead), cartilage (large arrow), and bone (small arrows). FIGS. 8d-e are ×40 original magnification H&E histology photomicrographs depicting bone and cartilage, respectively. FIGS. 8f-h depict 24- to 25-day gestational stage grafts. FIG.

8*f* is a ×10 original magnification H&E histology photomicrograph showing myofibroblasts (arrowheads) and cartilage (large arrow). FIGS. 8*g-h* are ×40 original magnification H&E histology photomicrographs depicting myofibroblasts and a representative glandular tissue-like structure, respectively.

Figure 9A:
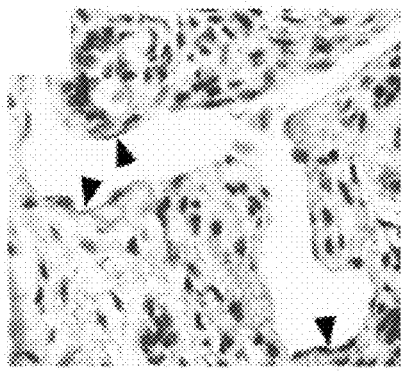
Figure 9B:
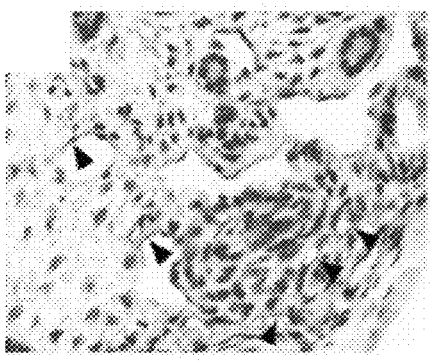
Figure 9C:
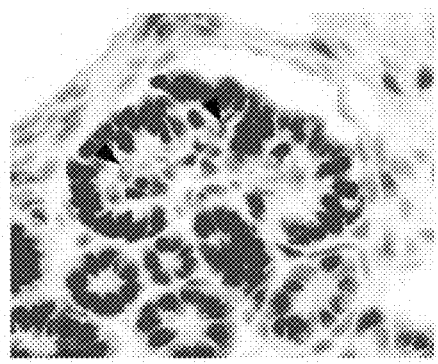
Figure 9D:
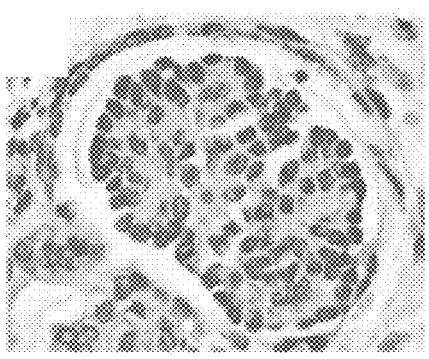
Figure 9E:
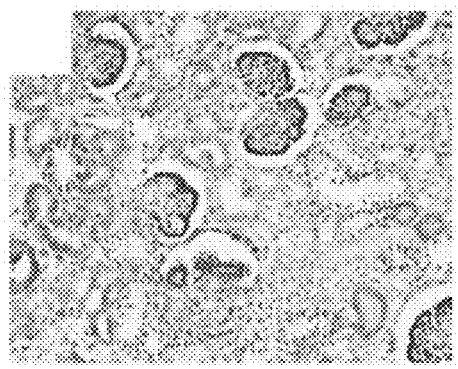

FIGS. 9*a-e* are photomicrographs depicting host-specific vascularization of porcine 28-day gestational stage renal grafts, in contrast to later-stage grafts. Grafts of 28-day gestational stage porcine developing kidneys were immunostained 4 weeks posttransplantation with antibody against mouse CD31 (PECAM). FIG. 9*a* depicts positive staining (arrowheads) in larger vessels. FIG. 9*b* depicts positive staining (arrowheads) in medium and small-size capillaries. FIG. 9*c* depicts positive staining (arrowheads) in developing glomeruli. FIG. 9*d* depicts lack of staining in glomeruli and small-size capillaries in transplants of mature 56-day gestational stage porcine fetal kidney tissue, 4 weeks posttransplantation. Original magnifications of FIGS. 9*a-d* are ×40. FIG. 9*e* depicts lack of positive staining for CD31 in negative control vascularized human fetal kidney (×20 original magnification).

Figure 10:
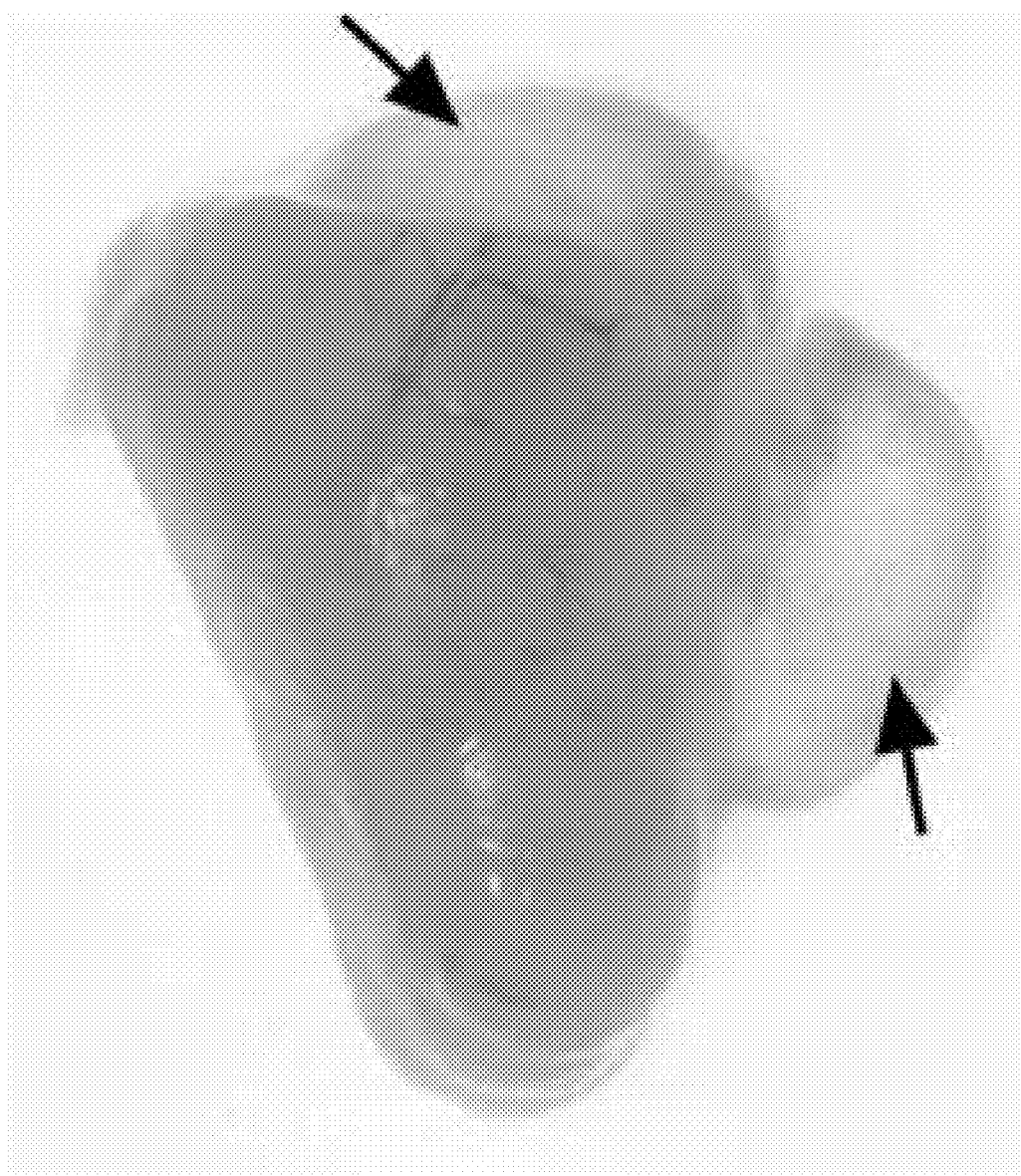

FIG. 10 is a whole-graft photograph depicting generation of large cysts filled with dilute urine (indicated by arrows) by porcine 28-day gestational stage renal grafts transplanted into immunodeficient mice, 8 weeks posttransplantation.

Figure 11A:
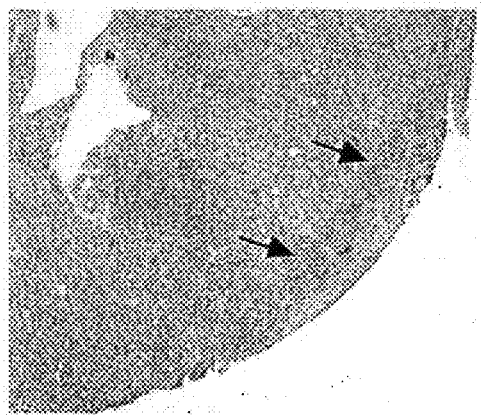
Figure 11B:
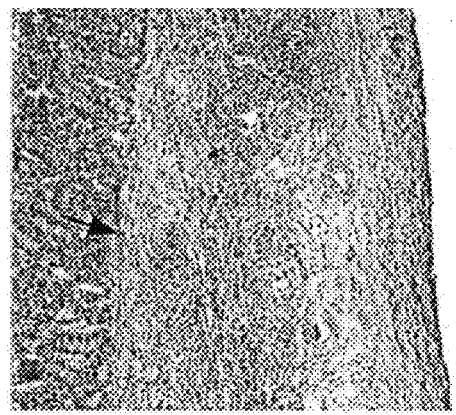
Figure 11C:
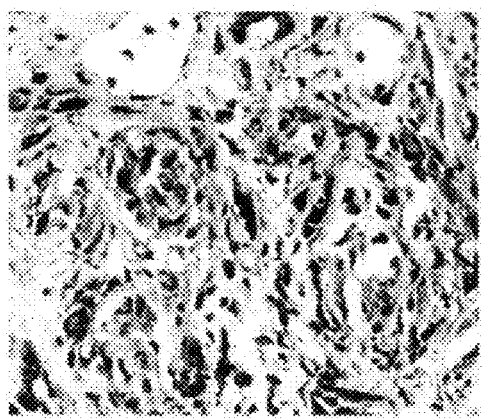

FIGS. 11*a-c* are photomicrographs depicting rejection of adult porcine renal grafts following transplantation into immunodeficient mouse hosts bearing human leukocytes. FIGS. 11*a-b* are ×4 and ×20 magnification views, respectively, depicting hematoxylin and eosin (H&E) histological staining of subcapsular adult porcine kidney tissue-derived grafts, 4 weeks following intraperitoneal infusion of human PBMCs. FIG. 11*c* depicts T-lymphocyte infiltration in transplanted tissue, as determined via immunohistochemical analysis of human CD3 expression.

FIGS. 12*a-d* are data plots depicting the significantly optimally high growth/low immunogenicity of porcine renal grafts at a gestational stage of 28-days or earlier, relative to later stage grafts following transplantation into immunodeficient mouse hosts bearing human leukocytes. FIGS. 12*a-d* respectively depict growth curves of 21-, 28-, 42- and 56-day gestational stage grafts transplanted into hosts infused (closed triangles) or not infused (open squares) with human PBMCs, 8 weeks posttransplantation. In 42- or 56-day gestational stage grafts, $P<0.01$ and $P<0.05$ compared with controls, respectively.

FIGS. 13*a-c* are photomicrographs depicting destruction of transplant tissue by invading human T-lymphocytes in 56-day gestational stage porcine renal grafts following transplantation into immunodeficient mouse hosts bearing human leukocytes. FIGS. 13*a-b* (×40 original magnification) depict immunostaining with anti-human CD3 antibody, and FIG. 13*c* depicts H&E histological staining (×10 original magnification), 4 weeks posttransplantation.

FIGS. 14*a-b* are photomicrographs depicting preserved glomeruli and tubuli with no infiltration of human T-lymphocytes in porcine 28-day gestational stage renal grafts following transplantation into immunodeficient mouse hosts bearing human leukocytes. Graft sections were analyzed via anti-human CD3 immunohistochemistry, 4 weeks posttransplantation (×40 original magnification).

Figures 15A, 15B:
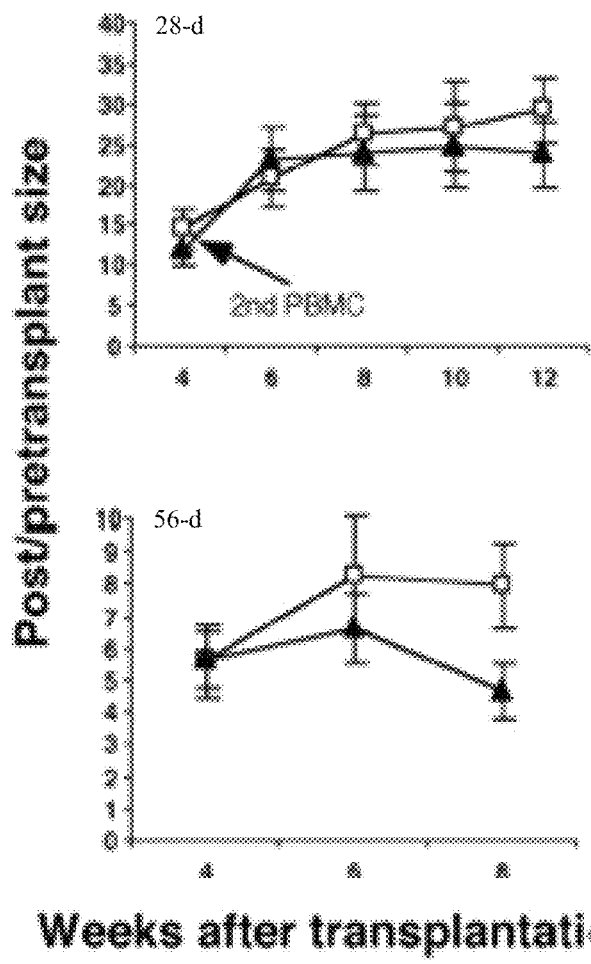

FIGS. 15*a-b* are data plots respectively depicting significant growth of, and tolerance to, porcine 28-day gestational stage renal grafts, and reversed growth, and rejection of 56-day gestational stage renal grafts in immunodeficient mouse hosts bearing human leukocytes from two different donors. FIG. 15*a* depicts the growth curve of 28-day gestational stage grafts following transplantation into immunodeficient mouse hosts in conjunction with 100 million human PBMCs from a first donor, and following infusion of the hosts 4 weeks posttransplantation with a second dose of 100 million PBMCs from a different human donor. FIG. 15*b* depicts the growth curve of 56-day gestational stage grafts following transplantation into immunodeficient mouse hosts in conjunction with 100 million human PBMCs from a first donor, and following infusion of the hosts 6 weeks posttransplantation with second dose of 100 million PBMCs from a different human donor. Graft growth in host receiving (closed triangles), or not receiving (open squares), a second infusion of PBMCs was measured at the indicated time-points ($P<0.05$, 8 weeks posttransplantation).

Figure 15E:
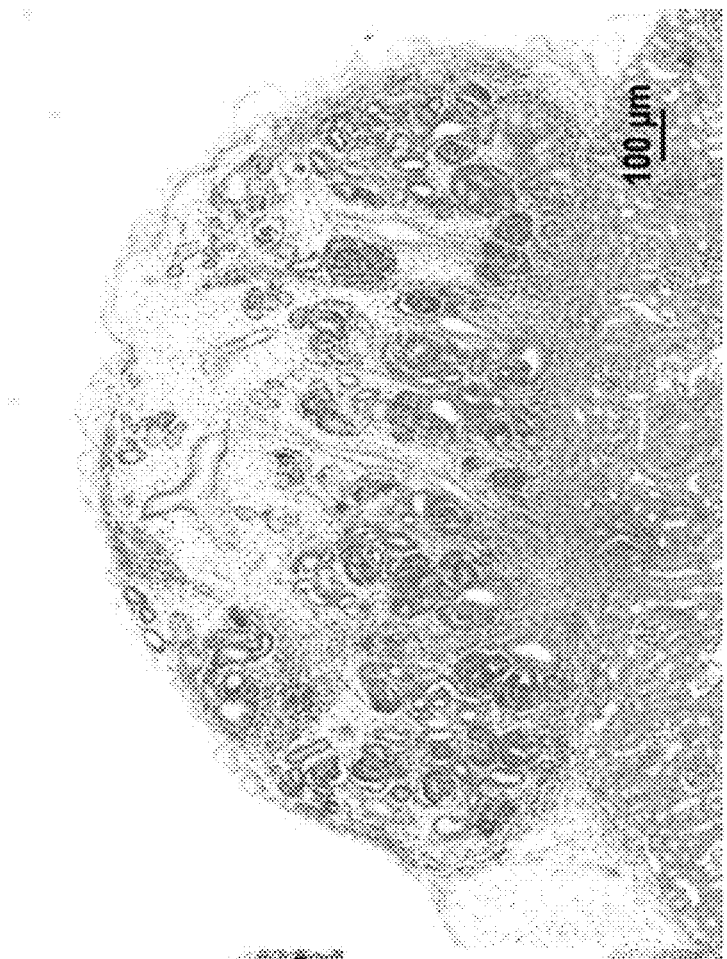
Figure 15C:
Figure 15D:
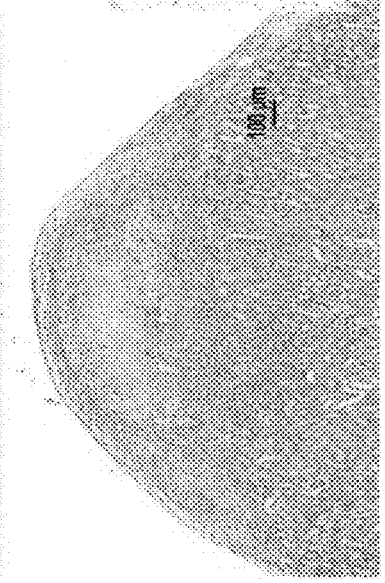

FIGS. 15*c-e* are H&E histochemistry photomicrographs depicting that porcine 28-day gestational stage renal grafts transplanted into immunocompetent C57BL/6 mice treated with rapamycin, CTLA4-Ig and anti-CD40L antibody generate well developed and tolerated renal organs. FIG. 15*c* depicts transplantation of grafts into immune deficient NOD-SCID mice, FIG. 15*d* depicts transplantation of grafts into immunocompetent C57BL/6 mice receiving no treatment, and FIG. 15*e* depicts transplantation of grafts into C57BL/6 mice treated with rapamycin, CTLA4-Ig and anti-CD40L antibody. Grafts were analyzed at 2 weeks posttransplantation.

FIGS. 16*a-e* are histology micrographs depicting generation of teratomas following subcapsular transplantation of porcine 21- or 24-day gestational stage liver grafts (FIGS. 16*a* and 16*b*, respectively) and generation of teratoma-free fully differentiated hepatic tissues following transplantation of porcine 28-day gestational stage hepatic grafts (FIGS. 16*c-e*). Grafts were transplanted under the renal capsule, and were analyzed histochemically for lineage-specific differentiation at 6 weeks posttransplantation. FIG. 16*a* depicts formation of teratomas by 21-day gestational stage grafts, as evidenced by Alcian-blue staining of cartilage (indicated by asterisk), a non-hepatic tissue type. In contrast, note generation, in the absence of teratoma-like structures, of well differentiated hepatic tissues demonstrating high levels of glycogen storage by 28-day gestational stage grafts, as evidenced via PAS staining (FIG. 16*c*), and significant levels of porcine albumin, as evidenced via anti-pig albumin immunohistochemistry (FIG. 16*d*; original magnification, ×4). FIG. 16*e* is an H&E histochemical analysis showing fully differentiated hepatic tissue architecture as evidenced by organization of the hepatocytes along hepatic cords surrounding the central veins (arrow head) while the portal elements of the liver are evident by formation of bile ducts (arrows).

Figure 17A:
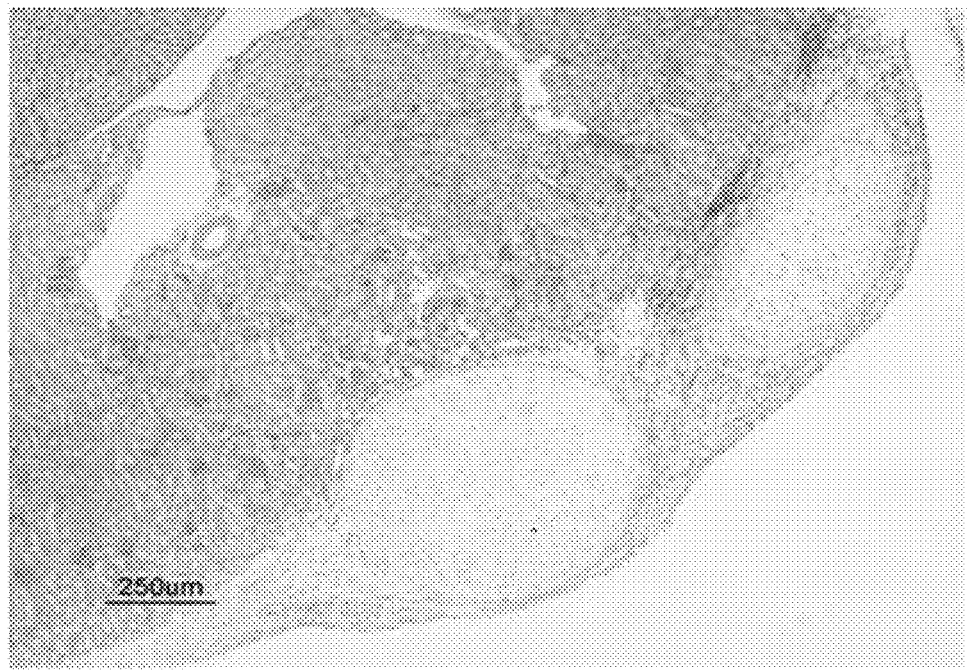
Figure 17B:
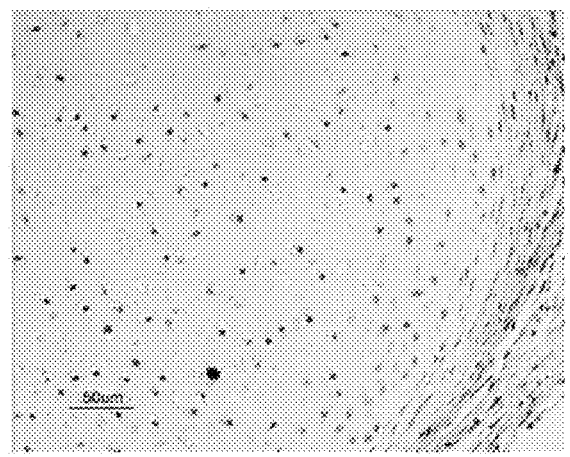

FIGS. 17*a-b* are photomicrographs depicting teratoma formation following intrasplenic transplantation of porcine 21-day gestational stage hepatic grafts. FIGS. 17*a* and 17*b* depict images at ×4 and ×20 original magnification, respectively. Note in FIG. 17*a* clear teratoma development with extensive cartilage differentiation. Grafts were implanted intrasplenically in NOD/SCID mouse recipients, and were analyzed via H&E staining at 7 weeks posttransplantation.

Figure 18A:
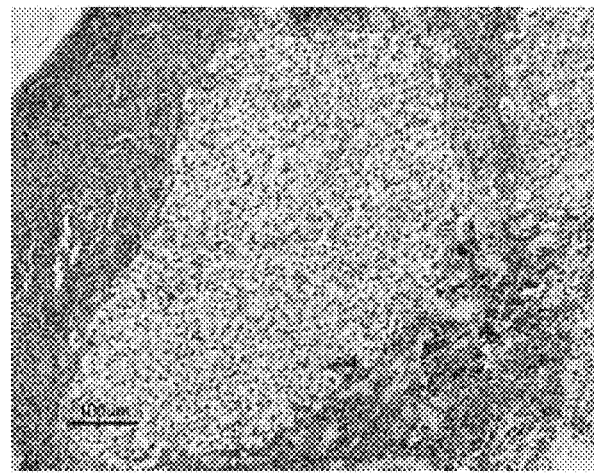
Figure 18B:
Figure 18D:
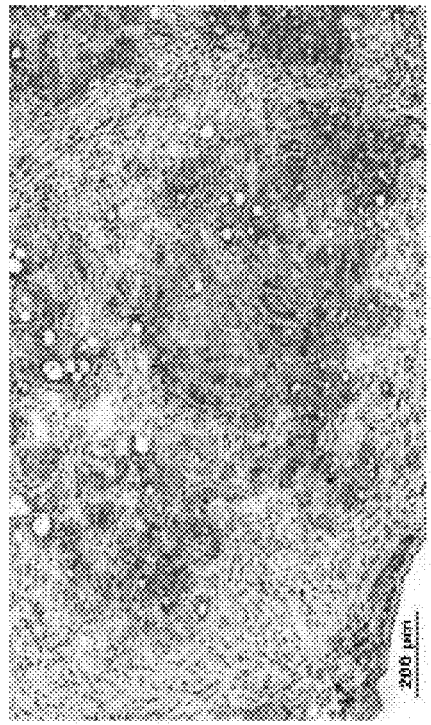
Figure 18F:
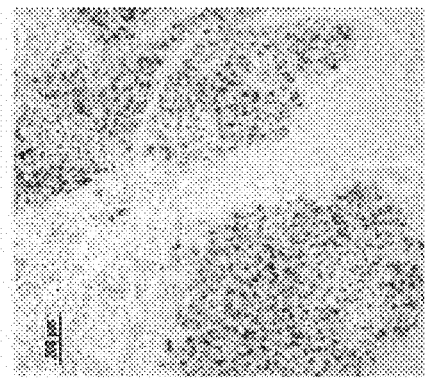
Figure 18C:
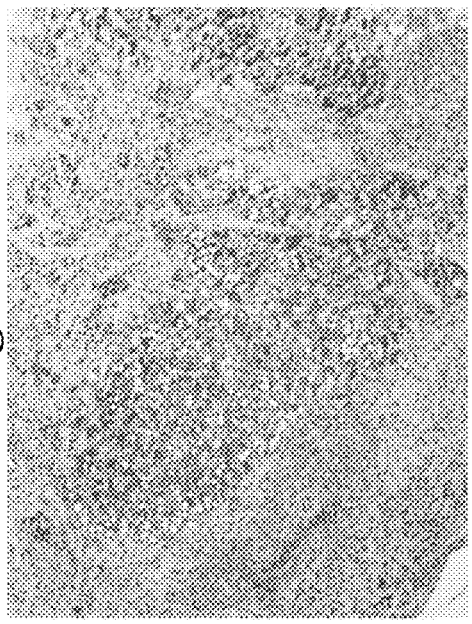
Figure 18E:
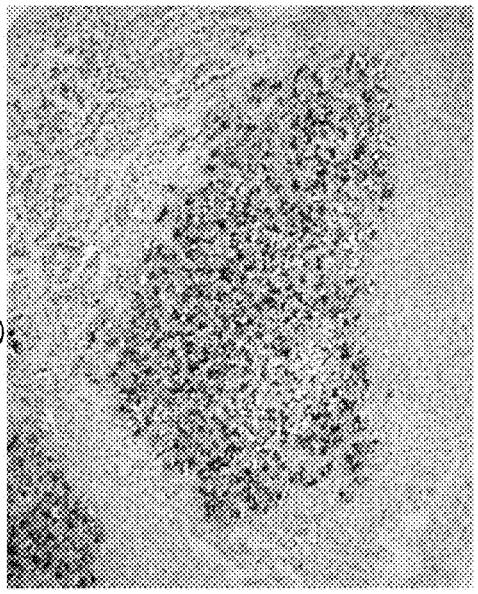
Figure 18G:
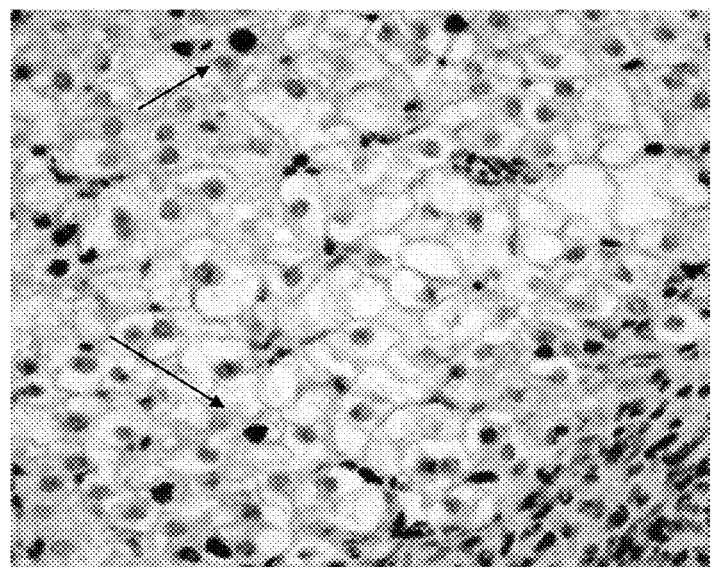
Figure 18H:
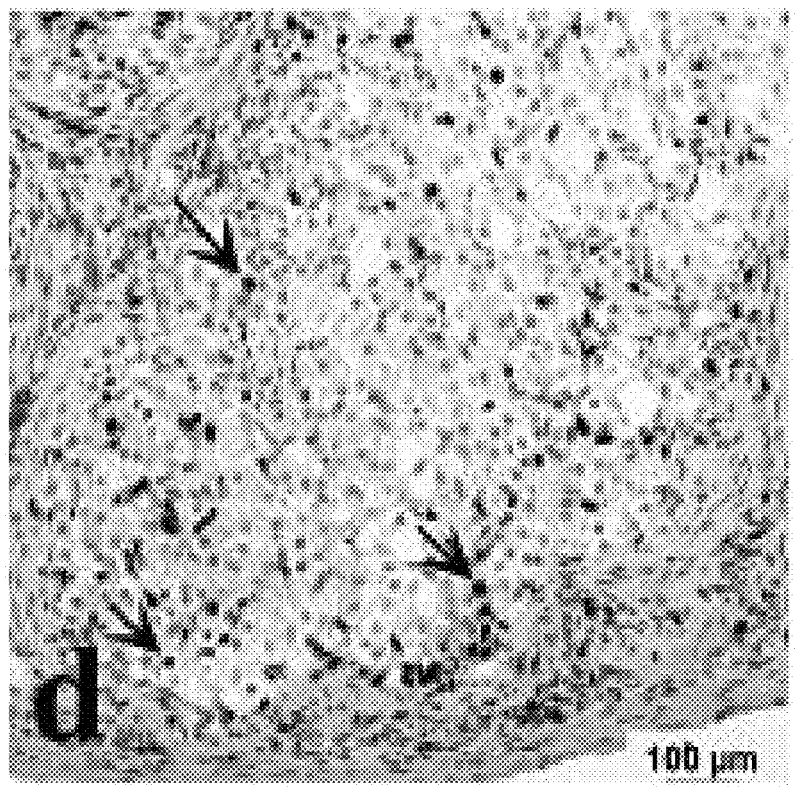

FIGS. 18*a-h* are histology photomicrographs depicting full hepatic development of graft-derived tissues following intrasplenic transplantation of porcine 28-day gestational stage grafts. Grafts were analyzed via staining with H&E (FIG. 18*a-b*), periodic acid-Schiff (PAS; FIG. 18*c-d*), anti-pig albumin antibody (FIG. 18*e-f*), and anti-Ki67 antibody (FIG. 18*g-h*). Note lobular patterns of hepatocyte arrangement in FIGS. 18*a* and 18*c-d*. Functionality of growing liver is indicated by positive PAS staining for glycogen (FIGS.

18c-d) and by positive anti-pig albumin antibody staining (FIGS. 18e-f). Original magnification of photomicrographs in FIGS. 18a, 18c and 18e, ×10. In FIGS. 18g-h, positive staining of hepatocyte nuclei (arrows) with anti-Ki67 antibody demonstrates proliferation of graft-derived hepatocytes. Grafts were implanted intrasplenically in NOD/SCID mouse recipients, and histological analysis was performed 6 weeks posttransplantation.

Figure 19A:
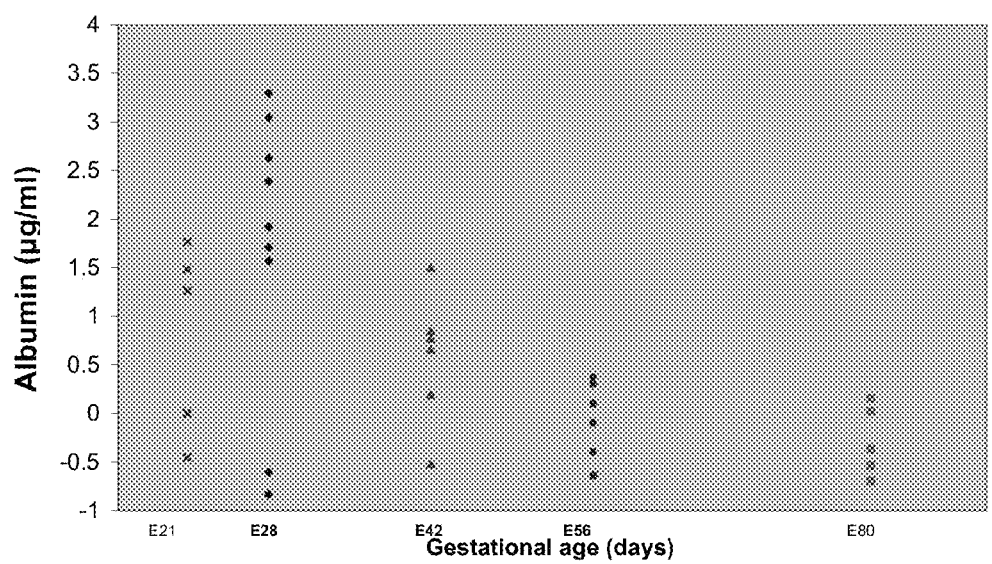
Figure 19B:
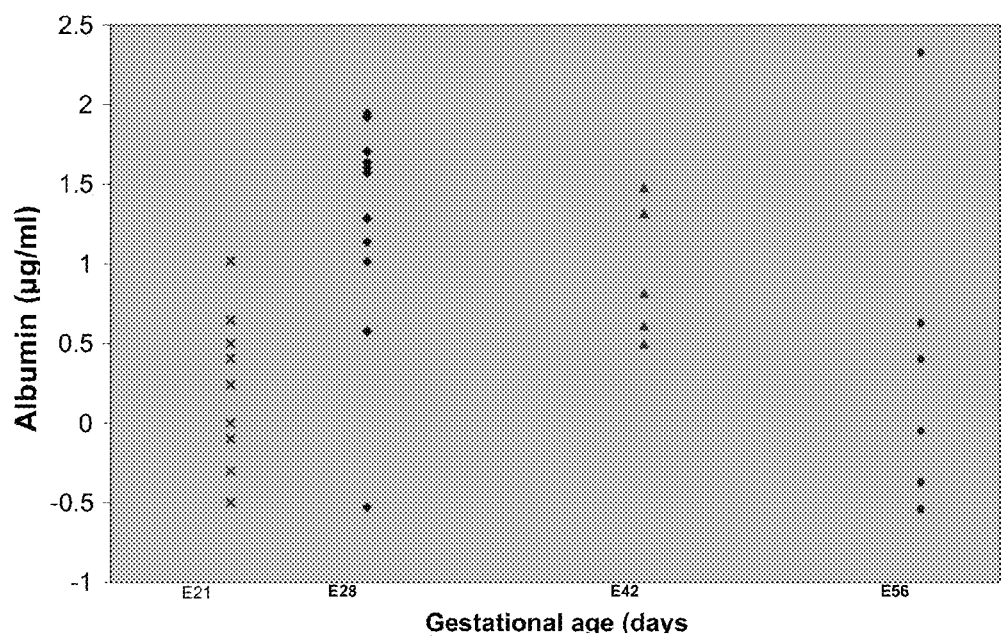

FIGS. 19a-b are cumulative dot plot ELISA histograms depicting that porcine 28-day gestational stage hepatic grafts are at an optimal gestational stage for generation of functional/albumin-secreting hepatic organs following transplantation into xenogeneic hosts. Pig albumin secretion in serum of mouse recipients of grafts at the indicated gestational stages was determined by ELISA using highly specific anti-pig albumin antibody, 6 weeks following intrasplenic (FIG. 19a) or subcapsular (FIG. 19b) transplantation.

Figure 19C:
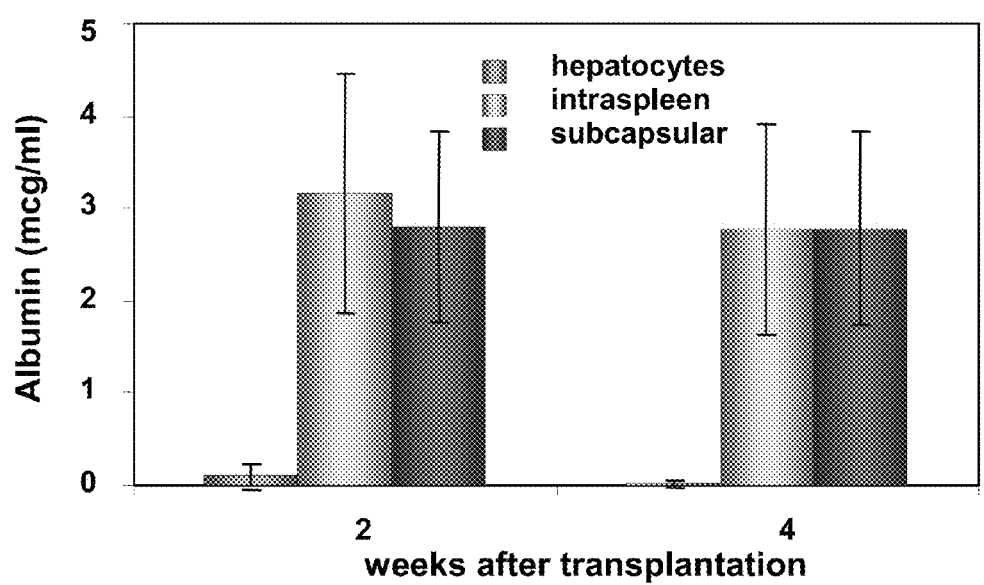

FIG. 19c is an ELISA histogram depicting significant levels of pig albumin secretion in serum of recipient mice at 2 and 4 weeks after receiving transplants of 28-day gestational stage porcine hepatic grafts into the spleen or under the renal capsule. Recipient hepatocytes were used as negative controls.

Figures 20A, 20B, 20C:
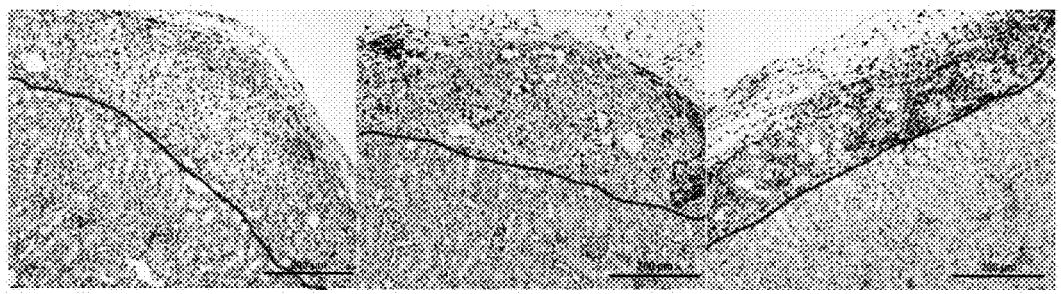

FIGS. 20a-c are immunohistochemistry photomicrographs depicting the rejection pattern of porcine gestational stage hepatic grafts mediated by human leukocytes, 4 weeks after transplantation under the kidney capsule of NOD-SCID mice. Grafts implanted at gestational stages of 24, 28 and 42 days (FIGS. 20a-c, respectively) were analyzed for infiltration by human lymphocytes via anti-human CD45 immunohistochemistry.

Figures 21A, 21B, 21C, 21D:
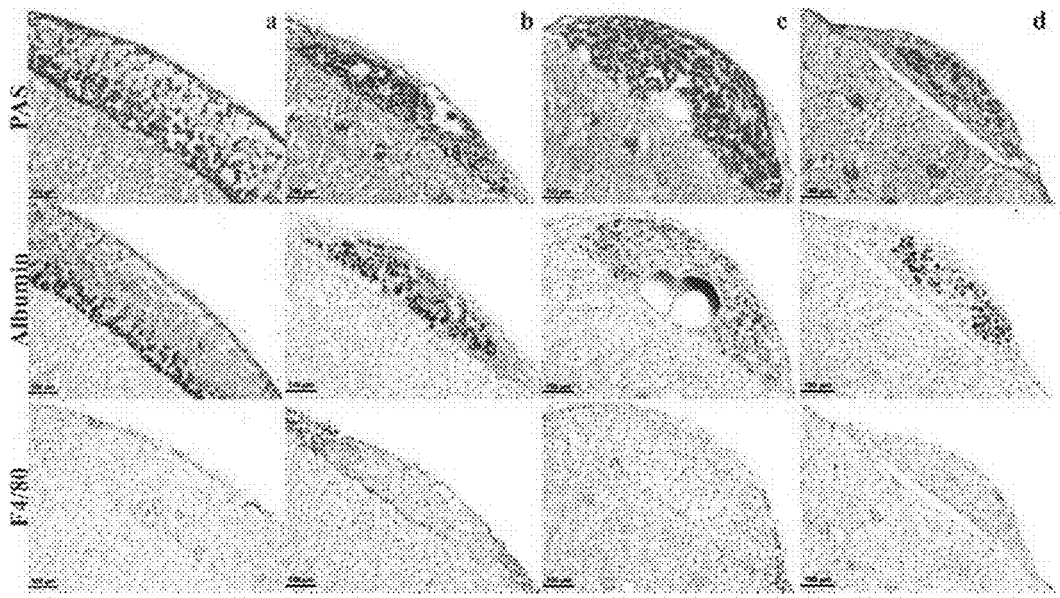

FIGS. 21a-d are histochemistry photomicrographs depicting that porcine hepatic grafts at gestational stages of 28-42 days transplanted into normal immunocompetent C57BL/6 mice treated with rapamycin, CTLA4-Ig and anti CD40L generate well developed and tolerated, functional hepatic tissues. Sections of graft-generated tissues were analyzed for hepatic functionality via PAS (glycogen detection), anti-pig albumin antibody and F4/80 antibody staining (mouse-specific glycoprotein detection). FIGS. 21a-b show analysis at 2 weeks posttransplantation of 28-day gestational stage grafts implanted into immunodeficient NOD-SCID mice, or into normal immunocompetent mice treated with rapamycin, CTLA4-Ig and anti CD40L, respectively. FIGS. 21c-d show analysis at 4 and 6 weeks posttransplantation, respectively, of 42-day gestational stage grafts implanted into C57BL/6 mice treated with rapamycin, CTLA4-Ig and anti-CD40L antibody.

Figure 22:
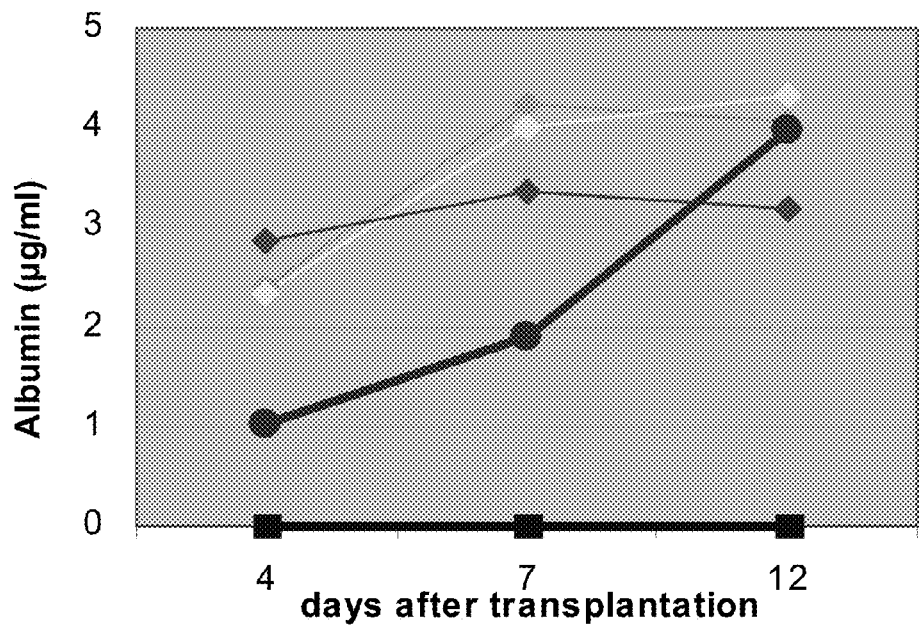

FIG. 22 is an ELISA data plot depicting that porcine 28-day gestational stage hepatic grafts transplanted into C57BL/6 mice treated with anti-CD40L antibody, CTLA-4 and rapamycin generate functionally differentiated hepatic organs capable of secreting porcine albumin (diamonds). As controls, such grafts were transplanted into immunodeficient NOD-SCID mice (circles), or into non-treated immunocompetent C57BL/6 mice (squares).

Figure 23:
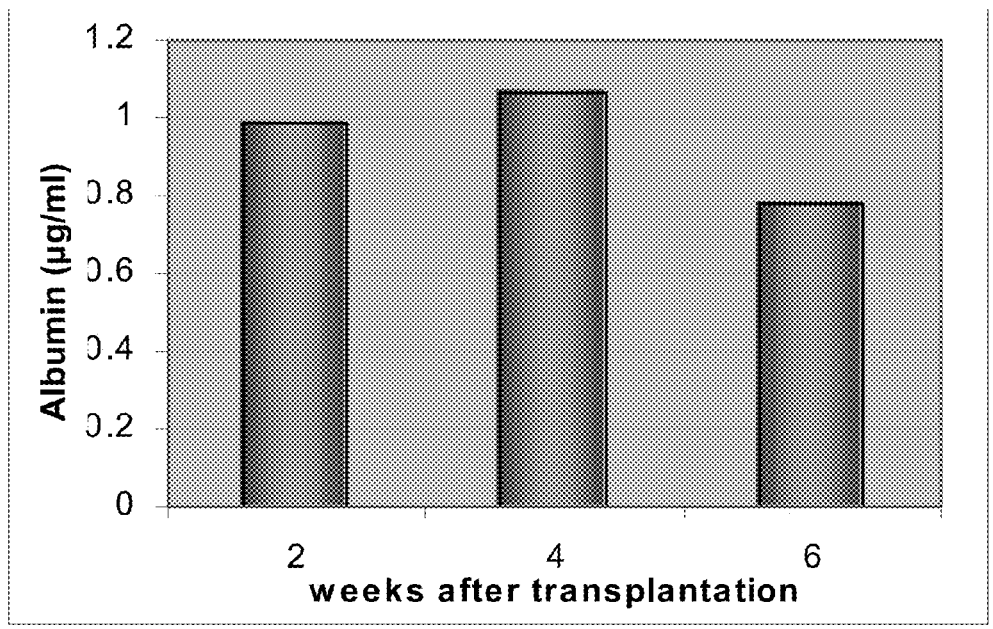

FIG. 23 is a ELISA histogram depicting that porcine 42-day gestational stage hepatic grafts transplanted into C57B1 mice treated with rapamycin, CTLA4-Ig and anti-CD40L antibody have the capacity to generate functional hepatic tissues which can secrete pig albumin for at least 6 weeks.

FIGS. 24a-b are histochemistry photomicrographs depicting that human 7-week gestational stage hepatic grafts have the capacity to generate fully differentiated functional hepatic organs following transplantation into immune deficient mammalian hosts. FIG. 24a is an H&E-stained graft section depicting bile duct differentiation (arrows), original magnification ×4. FIG. 24b is a PAS-stained graft section depicting the presence of well-differentiated, glycogen-storing hepatocytes, original magnification ×40. Grafts were transplanted under the renal capsule of NOD/SCID mice, and were analyzed 6 weeks posttransplantation.

DESCRIPTION OF THE PREFERRED EMBODIMENTS

The present invention is of methods of treating disorders by transplantation of grafts derived from developing human or porcine, kidney or liver. Specifically, the present invention relates to transplantation of porcine 27- to 28-day gestational stage renal grafts, or of human 49- to 56-day gestational stage renal grafts to treat renal disorders in humans. The present invention further specifically relates to transplantation of porcine 28-day gestational stage hepatic grafts, or of human 7-week gestational stage hepatic grafts to treat disorders amenable to treatment via hepatic transplantation in humans, such as hepatic failure, or a deficiency of a circulating enzyme or cell which can be produced by a healthy hepatic tissue. Such renal or hepatic grafts have the capacity to generate, without or with minimal risk of teratoma formation, highly developed, functional renal or hepatic organs, respectively, which will be well tolerated following transplantation into a non-syngeneic human host treated with minimal immunosuppression. The present invention therefore provides for the first time an essentially unlimited source of renal or hepatic grafts which can be used to treat human diseases amenable to treatment via transplantation of such grafts, such transplantation circumventing the severely restrictive prior art requirement for HLA-matching and, in the case of porcine grafts, harvesting of grafts from human donors.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Transplantation of fully differentiated/adult-stage renal allografts is currently the optimal or sole therapy for numerous highly debilitating and/or lethal renal disorders, and transplantation of fully differentiated/adult-stage hepatic allografts is currently the optimal or sole therapy for numerous highly debilitating and/or lethal hepatic and/or enzyme-deficiency disorders. However, current methods of renal or hepatic allograft transplantation are severely hampered by inadequate sources of matching donor organs/tissues, by the requirement for permanent and harmful immunosuppressive treatment of graft recipients to prevent graft rejection, and by the medical and ethical obstacles inherent to harvesting of grafts from human donors. It is well established in the prior art that the less an organ/tissue is differentiated, the lower the risk/strength of rejection of a graft derived from such an organ/tissue following transplantation thereof into a non-syngeneic recipient. Thus, a potentially optimal strategy for overcoming prior art obstacles to renal or hepatic transplantation would be to use grafts derived from porcine or allogeneic human developing kidney or developing liver. Ideally, in order to be optimal for non-syngeneic transplantation, a renal or hepatic graft should be derived from developing renal or hepatic organs/tissues, respectively, which are at a sufficiently early gestational stage to avoid graft rejection, while being at a sufficiently advanced gestational stage so as to be able to generate functional organs/tissues of graft lineage without risk of teratoma formation following transplantation. Such grafts would be well tolerated, would have potentially high potential capacity for growth and differentiation and thereby high potential capacity for integration with host anatomy/physiology. Critically, in the case of porcine grafts, such grafts would be in essentially unlimited supply, and their use would circumvent the medical and/or ethical drawbacks inherent to harvesting and use of grafts from human donors.

Various approaches involving use of grafts derived from developing kidney or liver for practicing non-syngeneic transplantation have been suggested or attempted in the prior art.

Such prior art approaches involve: transplanting cultured mouse ES cells into immune deficient allogeneic mice; generating genetically modified cultured ES cell-derived hepatocytes for transplantation; transplanting rat 15-day gestational stage (Barakat and Harrison, 1971. J. Anat. 110:393-407; Rogers, S. A. et al., 1998. Kidney Int. 54, 27-37; Rogers, S. A. et al., 2001. Am. J. Physiol. Regul. Integr. Comp. Physiol. 280, R132-136; Rogers, S. A. and Hammerman, M. R., 2001. Am. J. Physiol. Regul. Integr. Comp. Physiol. 281, R661-665; U.S. Pat. No. 5,976,524 to Hammerman), 17-day gestational stage (Barakat and Harrison, 1971. J. Anat. 110: 393-407; Abrahamson et al., 1991. Lab. Invest 64:629-639), or 1-day old neonatal (Barakat and Harrison, 1971. J. Anat. 110:393-407) renal grafts into allogeneic recipients; transplanting mouse 12-day gestational stage renal grafts into allogeneic recipients; transplanting rat 15-day gestational stage renal grafts into immunosuppressed mouse recipients (Rogers, S. A. and Hammerman, M. R., 2001. Am. J. Physiol. Regul. Integr. Comp. Physiol. 280, R1865-1869); transplanting human 98- to 154-day gestational stage renal grafts into chimeric rodents bearing human PBMCs (Dekel B. et al., 1997. Transplantation 64, 1550); transplanting human 70-day gestational stage (Dekel B. et al., 2000. Transplantation 69, 1470) renal grafts into immune deficient rodents; transplanting porcine approximately 20- to 30-day gestational stage renal grafts into human recipients (U.S. Pat. No. 5,976,524 to Hammerman); transplanting porcine embryonic hepatocytes into the spleen of immune deficient rats (Kokudo N. et al., 1996. Cell Transplantation 5:S21-2); transplanting encapsulated porcine fetal liver fragments into the omentum of rodent (Takebe K. et al., 1996. Cell Transplant 5:S31-3), or canine (Kanai N. et al., 1999. Cell Transplantation 8:413-7) recipients with hepatic failure; transplanting porcine fetal liver tissue into dogs (Kanai N. et al., 1999. Transplant Immunology 7:95-9); and transplanting rat fetal liver into immunosuppressed allogeneic recipients (Kokudo N. et al., 1996. Cell Transplantation 5:S21-2).

However, all prior art approaches for transplantation of human or porcine developing renal or hepatic grafts have significant disadvantages, including: undemonstrated or suboptimal short- or long-term immune tolerance by graft hosts, and/or requirement for graft host immunosuppressive treatment; undemonstrated or suboptimal short- or long-term structural and functional graft differentiation into renal or hepatic organs; predominantly graft-derived, as opposed to host-derived, graft vascularization following transplantation (which strongly correlates with risk of graft rejection); inadequate availability of transplantable grafts; and failure to demonstrate that the grafts employed are, at a sufficiently advanced developmental stage to avoid teratoma/undesired tissue lineage differentiation following transplantation, and hence failure to demonstrate safety for therapeutic applications. Xenogeneic approaches involving non-porcine organ grafts fail to provide grafts which are optimal for therapeutic transplantation in humans. Approaches involving encapsulated hepatic grafts fail to provide hepatic grafts capable of providing any of the numerous critical hepatic functions requiring free contact between the liver and circulating cells/particles.

The risk of teratoma formation by transplanted grafts derived from organs/tissues at sufficiently early developmental stages, and the undesirability of teratoma formation in the transplantation context is well established in the prior art (refer, for example, to: Bjorklund L M. et al., 2002. Proc. Natl. Acad. Sci. U.S.A. 99:2344-2349; Freed CR., 2002. Proc. Natl. Acad. Sci. U.S.A. 99:1755-1757). It is further well established in the prior art that tissues/organs of different lineages, such as renal or hepatic lineages, have potentially distinct developmental stage thresholds at which these attain terminal differentiation, and thereby become substantially devoid of pluripotential cells capable of generating teratomas. However, the developmental stage thresholds at which renal or hepatic graft are not only sufficiently differentiated so as to be capable of generating following transplantation into non-syngeneic hosts functional renal or hepatic organs/tissues, respectively, but are also sufficiently differentiated so as to avoid risk of teratoma formation, has never been suitably characterized in the prior art, nor does the prior art provide for any method of accurately and precisely predicting such thresholds for a renal or hepatic graft. Furthermore, the developmental stage ceiling at which a renal or hepatic graft remains sufficiently undifferentiated so as to have minimal tendency to undergo immune rejection following transplantation into a non-syngeneic host has similarly never been empirically characterized in the prior art, nor does the prior art provide for any method of reliably predicting such a ceiling for a renal or hepatic graft.

Thus, the prior art has failed to prove the hypothetical existence of developmental time-windows for either of renal or hepatic organs/tissues at which such grafts derived therefrom will have the capacity, following transplantation into a non-syngeneic host, to generate, in the absence of teratoma formation, well-developed and tolerated functional renal or hepatic organs/tissues, respectively.

While reducing the present invention to practice, as described and illustrated in Examples 1-3 of the Examples section below, the present inventors have performed numerous transplantation experiments which unexpectedly confirmed for the first time theoretical speculation that there may exist developmental stages at which porcine or allogeneic human renal grafts, respectively, can be transplanted into a minimally immunosuppressed mammalian host so as to be capable of generating, without risk of teratoma formation, highly developed, functional renal organs which are well tolerated by the host. In particular, while reducing the present invention to practice, the present inventors have identified porcine renal grafts at a gestational stage of 27 to 28 days, and human renal grafts at a gestational stage of 49 to 56 days, as being at optimal gestational stages for therapeutic transplantation. Thus, transplantation of porcine or human renal grafts at such gestational stages can be used to structurally/functionally replace/repair renal organs/tissues which are lacking or deficient in, or which display pathological physiology/morphology in, minimally immunosuppressed recipients of such grafts. As such, the presently disclosed experimental data enables optimal treatment of renal disorders in humans via transplantation of xenogeneic or allogeneic renal grafts.

Further while reducing the present invention to practice, as described in Examples 5-6 of the Examples section below, the present inventors have performed trial and error experiments which for the first time define the timing of, and thereby unexpectedly confirm speculation to the effect that there exist, a developmental stage at which porcine hepatic grafts can be transplanted into a minimally immunosuppressed xenogeneic mammalian host so as to be capable of generating, without risk of teratoma formation, well developed and tolerated, functional hepatic organs. In particular, while reducing the present invention to practice, the present inventors have identified porcine hepatic grafts at a gestational stage of 28 days as being at an optimal developmental stage for therapeutic transplantation. Further while reducing the present invention to practice, as described in Example 7 of the Examples section below, the present inventors have performed trial and error experiments which for the first time define the timing of, and thereby unexpectedly confirm speculation to the effect that there exist, a developmental stage at which human hepatic grafts can be transplanted into a non-syngeneic mammalian host so as to be capable of generating highly developed, functional hepatic organs. In particular, while reducing the present invention to practice, the present inventors have identified human hepatic grafts at a gestational stage of 7 weeks as being at a suitable developmental stage for therapeutic transplantation. Thus, transplantation of porcine or human hepatic grafts at such a gestational stages can be used to structurally/functionally replace/repair hepatic organs/tissues, respectively, which are lacking or deficient in, or which display pathological physiology/morphology in, recipients of such grafts. As such, the presently disclosed experimental data enables optimal treatment of a hepatic and/or enzyme deficiency disorder in a human via transplantation of xenogeneic or allogeneic hepatic grafts.

Thus, according to one aspect of the present invention there is provided a method of treating a disorder in a subject in need thereof. The method is effected by transplanting into the subject a therapeutically effective renal or hepatic graft selected at a predetermined stage of differentiation which: (i) is sufficiently advanced so as to enable the graft to generate, preferably in the absence of graft-derived teratoma formation, a functional organ/tissue of graft lineage in the subject, following transplantation thereof into the subject; (ii) is sufficiently early so as to enable the graft to be optimally tolerated by the subject relative to later-stage grafts following transplantation thereof into the subject; or (iii) where the subject is non-syngeneic with the graft, preferably all of which.

As used herein, "treating" the disorder includes curing, alleviating, or stabilizing the disorder, or inhibiting future onset or development of the disorder.

As used herein, the term "disorder" refers to any disease, or to any pathological or undesired condition, state, or syndrome, or to any physical, morphological or physiological abnormality which is amenable to treatment via renal and/or hepatic transplantation. Examples of such disorders are provided hereinbelow.

Depending on the transplantation context, in order to facilitate engraftment of the graft, the method may further advantageously comprise treating the subject with a minimal immunosuppressive regimen prior to, concomitantly with, or following transplantation of the graft. Such immunosuppressive treatment is described hereinbelow.

Transplanting the graft may be effected in numerous ways, depending on various parameters, such as, for example, the graft type; the type, stage or severity of the disorder; the physical or physiological parameters specific to the individual subject; and/or the desired therapeutic outcome. Depending on the application and purpose, transplanting the graft may be effected using a graft originating from any of various mammalian species, by implanting the graft into various anatomical locations of the subject, using a graft consisting of a whole or partial organ or tissue, and/or by using a graft consisting of various numbers of discrete organs, tissues, and/or portions thereof. Regardless of the particular method employed, it will be appreciated that transplanting the graft should be effected so as to achieve optimal treatment of the disorder.

Optionally, when transplanting a graft of the present invention into a subject having a defective renal or hepatic organ/tissue, respectively, the diseased organ/tissue it may be advantageous to first remove the defective organ/tissue from the subject so as to enable optimal development of the graft, and structural/functional integration thereof with the anatomy/physiology of the subject.

One of ordinary skill in the art, such as a physician, in particular a transplant surgeon specialized in the disorder, would possess the expertise required for applying the teachings of the present invention towards treating essentially any disorder in the subject amenable to treatment via renal or hepatic transplantation. Guidance for performing renal or hepatic transplantation according to the teachings of the present invention is provided further hereinbelow.

Depending on the application and purpose the method may be effected using a graft which is syngeneic or non-syngeneic with the subject. Preferably, the graft is non-syngeneic with the subject.

As used herein, a graft which is "syngeneic" with the subject refers to a graft which is essentially genetically identical with the subject. Typically, essentially fully inbred mammals, mammalian clones, or homozygotic twin mammals are syngeneic.

Examples of syngeneic grafts include a graft derived from the subject (also referred to in the art as an "autologous graft"), a clone of the subject, or a homozygotic twin of the subject.

As used herein, a graft which is "non-syngeneic" with the subject refers to a graft which is allogeneic or xenogeneic with the subject's lymphocytes. Typically, a graft which is derived from a donor which is non-syngeneic with the subject is non-syngeneic with the subject.

As used herein, a graft which is "allogeneic" with the subject refers to a graft which is derived from a donor which is of the same species as the subject, but which is substantially non-clonal with the subject. Typically, outbred, non-zygotic twin mammals of the same species are allogeneic with each other.

As used herein, a graft which is "xenogeneic" with the subject refers to a graft which substantially expresses antigens of a different species relative to the species of a substantial proportion of the lymphocytes of the subject. Typically, outbred mammals of different species are xenogeneic with each other.

As is described and illustrated in the Examples section below, transplanting a graft of the present invention into immunodeficient mice, or normal mice subjected to a minimal immunosuppressive regimen according to the teachings of the present invention can be used to generate in such mice, with no/minimal risk of teratoma formation, graft-derived well developed and tolerated functional organs/tissues of graft lineage.

As mentioned hereinabove, the graft may be derived from any one of various mammalian species.

Preferably, the graft is derived from a mammalian organ/tissue, more preferably from a human organ/tissue, and most preferably from a porcine organ/tissue.

Porcine grafts are widely considered to be a potentially ideal animal alternative to human grafts for therapeutic transplantation in humans due to their morphological compatibility with the human anatomy, and due to their essentially unlimited supply which would overcome the restricted availability impediment inherent to prior art human grafts (Auchincloss, H. and Sachs, D. H., 1998. Annu. Rev. Immunol. 16, 433-470; Hammerman, M. R., 2002. Curr. Opin. Nephrol. Hypertens. 11, 11-16).

Grafts of porcine origin are preferably obtained from a source which is known to be free of porcine zoonoses, such as porcine endogenous retroviruses. Similarly human-derived grafts are preferably obtained from substantially pathogen-free sources.

As described hereinabove, while reducing the present invention to practice, the gestational stages of human or porcine renal organ/tissue grafts during which these are at optimal predetermined stages of differentiation for practicing therapeutic non-syngeneic renal transplantation were identified, as described and illustrated in Examples 2 and 3, respectively, of the Examples section below.

When using a porcine renal graft for practicing the renal transplantation method of the present invention, the graft is preferably derived from a porcine kidney which is at a developmental stage selected from a range of 26 to 29 days of gestation, and most preferably which is at a developmental stage of 27 to 28 days of gestation.

As is described and shown in Example 3 of the Examples section which follows, porcine renal grafts at 27-28 days of gestation, unlike earlier-/later-stage grafts, have the capacity to generate, in the absence of teratoma formation, well developed and tolerated functional, urine-producing renal organs following transplantation into immunodeficient mice. As is further described in Example 3 of the Examples section which follows, porcine renal grafts at a gestational stage of 28 days have the capacity to generate, in the absence of teratoma formation, well developed and tolerated renal tissues following transplantation into normal mice minimally immunosuppressed via treatment with CTLA4-Ig, anti-CD40L and rapamycin according to the teachings of the present invention.

The presently taught method of using grafts derived from porcine 27- to 28-day gestational stage kidney for performing renal transplantation is clearly novel and non-obvious over the prior art, including over the closest relevant prior art, U.S. Pat. No. 5,976,524 to Hammerman (hereinafter the '524 patent). The '524 patent can be shown, in fact, to provide vague, contradictory, unvalidated, speculative and substantially incorrect teachings as to suitable developmental stages of porcine developing kidney for therapeutic transplantation. In a first instance, the '524 patent teaches that a suitable gestational stage corresponds to "approximately" 20-30 days of gestation (column 5, sentence starting at line 17) which, with a conservative interpretation of the qualifier "approximately" as indicating a minimal variation of plus/minus 1 day, corresponds to a developmental stage of 19-31 days of gestation. In a second instance, the '524 patent teaches that the optimal gestational stage is 2 to 4 days after metanephros formation (column 4, sentence starting at line 48), which according to the '524 patent occurs at day 20 of gestation (column 5, Table 1), resulting in an optimum range of 22 to 24 days of gestation. In a third instance, clearly contradictory to the second instance, the '524 patent teaches that grafts optimal for therapeutic transplantation have a diameter of 10 millimeters (column 5, sentence starting at line 16), a diameter which narrowly corresponds to that of a 21-day gestational stage kidney. The ordinarily skilled artisan will be aware that the developmental progression of a porcine kidney between 21 and 24 days of gestation is quite extensive, and is correspondingly even more extensive from 19 to 31 days of gestation. As such, the '524 patent provides confusing and unclear teachings with regard to suitable/optimal developmental stages of porcine renal grafts for transplantation. Moreover, even when combining for the sake of argument the contradictory optima of 21 days of gestation and 22-24 days of gestation to a hypothetically taught optimum of 21-24 days of gestation, the presently disclosed reduction to practice nevertheless unexpectedly convincingly teaches that grafts throughout this gestational stage range are very clearly suboptimal for therapeutic transplantation. Namely, while reducing the present invention to practice, as is summarized in Table 4 of the Examples section which follows, porcine renal grafts at a gestational stage of 21-25 days of gestation are presently shown to be associated, following transplantation thereof into an immunodeficient xenogeneic host with a significant incidence of growth failure, an approximately 50 percent failure rate in generation of renal tissues, and an approximately 50 percent incidence of teratoma-like differentiation, all of which being highly unsuitable and undesirable characteristics in the therapeutic transplantation context. In sharp and critical contrast, however, the significantly larger number of transplants of 27- to 28-day gestational stage porcine renal grafts analyzed under identical conditions while reducing the present invention to practice (Table 4 of the Examples section which follows) unexpectedly displayed a 100 percent incidence of graft growth, of renal differentiation, and complete absence of teratoma formation, thereby demonstrating for the first time that grafts at such gestational stages are optimal for therapeutic transplantation. Thus, as unexpectedly proven in the present reduction to practice, most of the approximately 20- to 30-day gestational stage range described by the '524 patent as being suitable for transplantation, i.e. the range of 20-25 days of gestation, is in fact highly unsuitable for therapeutic transplantation. The presently disclosed undesirable capacity of porcine renal grafts at 21-25 days of gestation to generate teratomas following transplantation has in been fact been provided a supporting mechanism by recent in-vitro studies indicating that at such early gestational stages the developing kidney contains pluripotent progenitor cells with the ability to generate many cell types (Oliver, J. A. et al., 2002. Am. J. Physiol. Renal Physiol. 283, F799-809). Furthermore, the reduction to practice of the '524 patent does not describe transplantation of porcine or human developing kidneys, but rather is limited to transplantation of developing rat kidneys into the kidney or omentum of allogeneic recipients, or into the kidney of xenogeneic recipients. In the intra-kidney allogeneic model, lymphocyte accumulation at the graft-host interface must be prevented by intensive host immunosuppression using cyclosporin A ('524 patent, column 8, paragraph starting at line 3), and; in the intra-omental allogeneic model, lymphocyte accumulation, an undesirable prognostic indicator intimately associated with eventual graft rejection, occurs ('524 patent, column 9, "Example 3"), thereby confirming the aforementioned requirement for host immunosuppression to enable allograft tolerance. In the xenogeneic model, total degeneration of the renal graft into a fibrotic mass occurs in hosts which are not intensively immunosuppressed via cyclosporin A administration. Therefore, the reduction to practice of the '524 patent fails to teach a method of transplanting developing kidneys into a non-syngeneic host so as to achieve optimal graft tolerance without intensive host immunosuppression via cyclosporin A treatment, as most emphatically shown in the xenotransplantation context. The requirement for immunosuppression, including for allograft transplantation, when practicing the method of the '524 patent has in fact been confirmed by other investigators in recent studies (PCT Publication No. WO 2004/016276, refer to page 3, sentence starting at line 15). Critically, the teachings of the '524 patent reduction to practice are further lacking in that they fail to address the issue of, or in any way characterize, the undesirable risk of teratoma formation associated with transplantation of gestational stage renal grafts. In very sharp and critical contrast, however, the presently disclosed reduction to practice experimentally demonstrates for the first time a method of transplanting porcine or human developing renal allografts enabling generation of graft-derived renal organs which are optimally developed and functional, which do not display a capacity to generate teratomas/undesired tissue lineages, and which are well tolerated by functional xenogeneic or allogeneic leukocytes, respectively, such leukocytes, critically and in sharp distinction to the immunosuppressed murine host leukocytes of the reduction to practice of the '524 patent, being of human origin.

Thus, the prior art very clearly teaches away from the presently taught use of porcine 27- to 28-day gestational stage renal grafts for optimal therapeutic transplantation in humans. In fact, the validity of these presently disclosed teachings was confirmed by the author of the '524 patent and co-workers in studies published after issuance of the '524 patent and after the making of the present invention, which confirm that porcine renal grafts at a gestational stage of 28 days, significantly the only gestational stage thusly described therein, could be transplanted into non-syngeneic hosts so as to generate highly developed renal organs which are well tolerated by the host (Rogers S A. et al. 2003. ASAIO J. 49:48-52). In further support of the teachings of the present invention, there is a clear expectation in the art of technical and commercial success with regard to the presently taught use of porcine 28-day gestational stage kidneys for therapeutic transplantation in humans, as recently demonstrated by PCT Publication No. WO 2004/016276 to Intercytex Ltd., a company having received large financial investments for research and development of such technologies (described, for example, at the web site: http://www.intercytex.net/ICX.php?Page=newsitem&Item=IntercytexRaises£7Mi-11-11-03.htm). The aforementioned PCT publication describes and anticipates successful therapeutic transplantation in humans of developing porcine kidneys at a gestational stage of 28 days, again significantly the only gestational stage described therein for such use (page 41, "Example 10" in general, and in particular page 42, sentence starting at line 3).

As described hereinabove, the renal transplantation method of the present invention can be practiced using a human developing renal graft.

When using a human renal graft for practicing the renal transplantation method of the present invention, the graft is preferably derived from a human kidney which is at a developmental stage selected from a range of 48 to 57 days of gestation, more preferably which is at a developmental stage selected from a range of 49 to 56 days of gestation, and most preferably which is at a developmental stage of 49 or 56 days of gestation.

As is described and illustrated in Example 2 of the Examples section which follows, human renal grafts at a gestational stage of 49 or 56 days of gestation have the capacity to generate, in the absence of teratoma formation, well developed functional urine-producing renal organs following transplantation into immunodeficient mice.

As described hereinabove, while reducing the present invention to practice, the gestational stages of porcine or human hepatic organ/tissue grafts during which these are at optimal predetermined stages of differentiation for practicing therapeutic non-syngeneic hepatic transplantation were identified, as described in Examples 6 and 7, respectively, of the Examples section below.

While reducing the present invention to practice, it was unexpectedly uncovered that the well developed and tolerated, highly functional renal organs generated following transplantation of the porcine and human grafts at the optimal gestational stages taught by the present invention display predominantly host-derived vasculature, as detailed in Examples 2 and 3, respectively, of the Examples section which follows. Without being bound to a paradigm, the present inventors are of the opinion that renal grafts at the presently taught optimal gestational stages for transplantation have the capacity to generate graft-derived renal organs which, unlike later-stage grafts, have the capacity to be well tolerated by a xenogeneic host due to the gestational stage of such grafts being sufficiently early so as to confer upon such grafts the capacity to generate organs/tissues having such predominantly subject-derived vasculature. In support of this view, it is believed in the art, particularly with respect to xenografts, that the extent of host-derived vasculature of a transplanted graft correlates with host tolerance to the graft, and vice-versa.

The presently disclosed discovery that renal grafts at the presently taught optimal developmental stages for transplantation can be transplanted into a recipient so as to generate following transplantation into a recipient, in the absence of graft-derived teratoma formation, well developed, functional graft-derived renal organs which are well tolerated by functional allogeneic or xenogeneic leukocytes was clearly surprising since the developmental threshold beyond which such grafts are too developed to generate sufficiently host-vascularized renal organs had never been defined, and could not be predicted according to prior art knowledge for any given tissue lineage, such as kidney.

When using a porcine hepatic graft for practicing the hepatic transplantation method of the present invention, the graft is preferably derived from a porcine liver which is at a developmental stage selected from a range of 25 to 56 days of gestation, more preferably which is at a developmental stage selected from a range of 26 to 56, more preferably which is at a developmental stage selected from a range of 27 to 56 days of gestation, more preferably which is at a developmental stage selected from a range of 28 to 56 days of gestation, more preferably which is at a developmental stage selected from a range of 28 to 42 days of gestation, more preferably which is at a developmental stage selected from a range of 27 to 29 days of gestation, and most preferably which is at a developmental stage of 28 days of gestation.

As is described and illustrated in Example 6 of the Examples section which follows, porcine hepatic grafts at a gestational stage of 28 days have the novel capacity to generate, in the absence of teratoma formation, highly developed, functional hepatic tissues following transplantation into immunodeficient mice, or into normal mice minimally immunosuppressed via treatment with CTLA4-Ig, anti-CD40L and rapamycin according to the teachings of the present invention. In sharp contrast, such grafts at a developmental stage of up to 24 days of gestation possess substantial capacity to generate teratomas, and display a significant incidence of failure to display hepatic development, as summarized in Table 5 of the Examples section which follows. As is illustrated in Example 6 of the Examples section below, porcine hepatic grafts at a gestational stage of 28 days are clearly superior in generating functional hepatic organs/tissues relative to grafts at earlier or later developmental stages, and porcine hepatic grafts at gestational stages ranging from 28 to 56 days have the capacity to generate, in the absence of teratoma formation, functional hepatic tissues following transplantation into mammalian hosts.

When using a human hepatic graft for practicing the hepatic transplantation method of the present invention, the graft is preferably derived from a human liver which is at a developmental stage selected from a range of 6 to 14 weeks of gestation, more preferably which is at a stage of development selected from a range of 6 to 13 weeks of gestation, more preferably which is at a stage of development selected from a range of 6 to 12 weeks of gestation, more preferably which is at a stage of development selected from a range of 6 to 11 weeks of gestation, more preferably which is at a stage of development selected from a range of 6 to 10 weeks of gestation, more preferably which is at a stage of development selected from a range of 6 to 9 weeks of gestation, more preferably which is at a stage of development selected from a range of 6 to 8 weeks of gestation, and most preferably which is at a stage of development of 7 weeks of gestation.

As is described and shown in Example 7 of the Examples section which follows, human hepatic grafts at a gestational stage of 7 weeks have the capacity to generate highly developed, functional hepatic organs following transplantation into immunodeficient non-syngeneic mammalian hosts.

The present invention envisages that renal or hepatic grafts derived from species other than human or pig which are at stages of differentiation corresponding to the presently disclosed optimal gestational stages for transplantation may also be employed for practicing the method of the present invention. Animals such as the major domesticated or livestock animals, and primates, which have been extensively characterized with respect to correlation of stage of differentiation with gestational stage may be suitable for practicing the method. Such animals include bovines (e.g., cow), equids (e.g., horse), ovids (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

Various common art methods may be employed to obtain a graft at a stage of differentiation corresponding to a specific gestational period. Obtaining such a graft is optimally effected by harvesting the graft from a developing graft donor embryo or fetus at such a stage of gestation. It will be understood by one ordinarily versed in the art that the gestational stage of an organism is defined as the time period elapsed since its conception. The "conception" of an organism is defined herein as occurring at the time of fusion of the oocyte and the sperm involved in generating the organism. As used herein, a definition of a gestational stage of a graft or graft donor of the present invention in terms of a specific number of days refers to that number of days plus or minus one half-day (12 hours). Porcine and human gestational development have been extensively studied and characterized, and, as such, the ordinarily skilled artisan will possess the necessary expertise for suitably obtaining a porcine or human, renal or hepatic, organ or tissue at a specific gestational stage so as to enable the practicing of the present invention.

Alternately, the present invention envisages in-vitro culture of stem cells, or of renal or hepatic progenitor cells, to obtain a renal or hepatic graft, respectively, at the desired developmental stage. Controlled in-vitro differentiation of pluripotential cell lines, such as stem cell lines, to generate cultured cells/tissues/organs of desired lineages is routine in the art (refer, for example, to: Schuldiner M. et al., 2000. Proc Natl Acad Sci USA. 97:11307-11312; Itskovitz-Eldor J. et al., 2000. Mol Med 6:88).

Transplanting a renal graft of the present invention may be effected by transplanting the graft into any one of various anatomical locations, depending on the application and purpose. A renal graft of the present invention may be transplanted into a renal capsule or kidney of the subject, or it may be transplanted into an ectopic anatomical location, such as the intra-abdominal space, the omentum, and an intestinal loop. Transplantation of renal grafts into anatomical locations such as these is commonly practiced in the art to treat renal disorders.

As is shown in Examples 1-3 of the Examples section below, the renal transplantation method of the present invention may be practiced by transplanting a renal graft of the present invention under the renal capsule of a subject according to the present invention. As is described in Example 3 of the following Examples section urinary cysts were observed to form in intra-abdominal grafts where they were not growth-limited by the renal subcapsular space.

A renal graft of the present invention may advantageously be transplanted near a relatively large blood vessel, preferably within 1 cm thereto, in order to facilitate vascularization of the graft-derived renal organ. The renal graft may advantageously be implanted in a pouch formed in the retroperitoneal fat adjacent the large blood vessel.

Transplanting a renal graft of the present invention may be effected by transplanting into the subject one or more whole renal organs, and/or one or more partial renal organs. As is shown in Examples 1-3 of the Examples section which follows transplantation of whole renal organs into immunodeficient mammals, or into normal mice minimally immunosuppressed via treatment with CTLA4-Ig, anti-CD40L antibody and rapamycin, in accordance with the present teachings, can be used to generate in such hosts well developed and tolerated functional renal organs/tissues.

Transplanting a sufficient number of discrete renal organ grafts may be advantageously employed so as to achieve a sufficiently high urine production capacity to alleviate or cure a renal disorder in the subject. It will be appreciated that the lower the body weight of the subject, the less blood filtration capacity (renal functionality) will be required to treat a renal insufficiency in the subject. Therefore, transplantation of a limited number of renal grafts, or transplantation of renal grafts having limited capacity for hepatic functionality may be most advantageously employed to treat a such a disorder in a subject, such as a neonate, having a sufficiently/minimally low body weight as to render fully/optimally therapeutically effective such transplantation.

Current therapies for end-stage renal failure such as dialysis offer around 10 percent renal function. For comparison, approximately 40 percent of normal renal function is expected from allograft kidney transplantation. Typically, clinicians put a patient on dialysis at 7 percent of normal renal function. Therefore, it is preferable to perform the renal transplantation of the present invention in such a way as to achieve at least 10 percent of renal function, most preferably a maximal percentage of renal function.

Transplanting renal grafts into various anatomical locations of the subject may be exploited to achieve transplantation of a sufficient number of renal grafts into the subject so as to confer maximal/complete renal functionality to the subject so as to maximally/completely treat a renal disorder in the subject.

It will be appreciated by the ordinarily skilled artisan that in order to confer renal functionality to, and thereby treat a renal disorder in, a subject by transplantation of a renal graft of the present invention into the subject, it is necessary to achieve as a result of such transplantation: (i) vascularization of the graft so as to enable the graft-derived renal organ to filter the blood of the subject and generate urine; and (ii) removal of the graft-generated urine out of the subject.

With regard to achieving vascularization of the graft resulting in urine-production, it is clearly shown in Examples 2 and 3 of the following Examples section that a renal graft of the present invention, following transplantation thereof into a subject, has the inherent capacity to undergo host-derived vascularization in-vivo, and to filter the blood of the subject and produce urine. It will be appreciated that vascularization of a graft-derived renal organ may be augmented via any one of various standard vascular surgery techniques, as described hereinbelow, so as to achieve a desired blood filtration rate by the graft-derived renal organ. The graft-derived renal organ may advantageously be placed in fluid communication with a large blood vessel the subject via the hilum thereof, so as to achieve efficient blood filtration.

With regard to achieving removal of graft-generated urine from the subject, various techniques, or combinations thereof, may be employed. As is described and illustrated in Examples 1-3 of the Examples section which follows, a catheter of appropriate dimensions may be surgically attached to such urinary cysts so as to achieve drainage thereof outside the body of the subject. As is further described and illustrated therein, where subcapsular transplantation of the renal graft is employed, the catheter requires only a short length to reach the skin of the subject. Alternately, urinary cysts of graft-derived renal organs may be drained into a ureter, or the bladder, of the subject via any one of various commonly practiced techniques. For example, an in-situ prosthetic ureter may be surgically implanted in the subject according to effective standard art methods so as to achieve such drainage (refer, for example, to: Desgrandchamps F and Griffith D P., 2000. The prosthetic ureter. J. Endourol. 14:63-77). A typical in-situ prosthetic ureter is a simple silicone/silicone rubber tube connected to the urinary tract by end-to-end sutures or by intubation and closure. Ureteral replacement with alloplastics, including a coaxial assembly of an inner silicone and outer expanded polytetrafluoroethylene tube, is known in the art to produce good results. As a further alternative, a ureter of a graft-derived renal organ implanted into the abdominal cavity of the subject can be anastomosed to the ureter of the subject using an end to end, or end to side anastomosis, for example as described in U.S. Pat. No. 5,976,524. Alternately, the renal pelvis of the renal tissue transplant may be anastomosed to the host's urinary system. In cases where multiple grafts have been implanted into the subject, the ureters of each graft-derived renal organ may be joined via anastomosis to form an interconnecting manifold draining into a ureter, or the bladder, of the subject.

It will be appreciated that drainage of a renal graft urinary cyst via surgical intervention will generally need to be performed after a duration allowing formation of such a cyst. As is described in Examples 1-3 of the following Examples section, a suitable duration is 6-10 weeks posttransplantation. Monitoring of urinary cyst formation via medical imaging methods may be advantageously performed in order to ascertain a suitable time for performing surgical intervention to allow graft drainage. Suitable, widely practiced, imaging methods include computerized tomography (CT) and ultrasound imaging.

Following transplantation of a renal graft into a subject according to the present teachings, it is advisable, according to standard medical practice, to monitor the growth and differentiation of the graft and the renal functionality of the subject according to any one of various standard art techniques, and/or as described in the Examples section which follows. As described in Examples 1-4 of the Examples section below, the functionality of a renal graft of the present invention in the may be monitored following transplantation by analysis of urinary cyst fluid, in particular by analysis of such fluid for a urine specific metabolite or by product content. Supra plasma concentrations of urine specific byproducts, such as, for example, urea nitrogen and creatinine are indicative of renal functionality. Renal functionality may be conveniently assessed via standard insulin-clearance assays.

One of ordinary skill in the art, such as a surgeon specialized in kidney transplantation, will possess the necessary expertise to adapt the teachings of the present invention so as to achieve treatment of a renal disorder in a human subject. Ample guidance is provided in the art for practicing therapeutic renal transplantation (refer, for example, to: Ramanathan V. et al., 2001. Renal transplantation. Semin Nephrol. 21:213-9; Curtis J J., 1998. End-stage renal disease patients: referral for transplantation. J Am Soc Nephrol. 9:S137-40; French C G. et al., 2000. Progress in renal transplantation. Can J. Urol. 7):1030-7; Barry J M., 1999. Renal transplantation. Curr Opin Urol. 9:121-7; and Cecka J M., 2000. Kidney transplantation from living unrelated donors. Annu Rev Med. 51:393-406). Guidance regarding transplantation of developing kidneys is available in the art (refer, for example, to Hammerman MR., 2002. Clinical Science 103: 599-612; Hammerman MR., 2004. Am J. Transplant. 4 Suppl 6:14-24).

An exemplary scheme for performing renal transplantation in a human according to the teachings of the present invention is outlined in Example 4 of the Examples section below.

Transplanting a hepatic graft of the present invention may be effected by transplanting the graft into any one of various anatomical locations, depending on the application and purpose. A hepatic graft of the present invention is preferably transplanted into the liver, the portal vein, the renal capsule, the sub-cutis, the omentum, the spleen, and the intra-abdominal space. Transplantation of hepatic grafts into various anatomical locations such as these is commonly practiced in the art to treat diseases amenable to treatment via hepatic transplantation.

As is shown in Examples 5-7 of the Examples section below, the hepatic transplantation method of the present invention may be practiced by transplanting a hepatic graft of the present invention under the renal capsule, or into the spleen of a subject according to the present invention. As is described in Example 6 of the following Examples section, transplantation of a hepatic graft of the present invention either under the renal capsule or into the spleen of a mammalian subject of the present invention enabled generation of graft-derived hepatic organs capable of secreting significant quantities of hepatic enzymes into the serum of the subject.

Transplanting a hepatic graft of the present invention may be effected by transplanting into the subject one or more whole hepatic organs, and/or one or more partial hepatic organs.

As is shown in Examples 5-7 of the Examples section which follows transplantation into a mammalian subject of a hepatic graft consisting of liver fragments according to the present teachings can be used to generate in the subject highly developed functional hepatic organs in the subject.

Transplanting a sufficient number of discrete hepatic grafts may be advantageously employed so as to achieve a sufficiently high mass of graft-derived hepatic organs/tissues, and thereby a sufficiently high level of hepatic functionality to alleviate or cure a disorder in the subject amenable to treatment via hepatic transplantation.

It will be appreciated that the lower the body weight of the subject, the less graft-generated hepatic functionality will be required to treat in the subject a disorder amenable to treatment via hepatic transplantation. Therefore, transplantation of a limited number of hepatic grafts, or transplantation of hepatic grafts having limited capacity for hepatic functionality may be most advantageously employed to treat such a disorder in a subject, such as a neonate, having a sufficiently/minimally low body weight as to render fully/optimally therapeutically effective such transplantation.

Transplanting hepatic grafts into various anatomical locations of the subject may be exploited to achieve transplantation of a sufficient number of hepatic grafts into the subject so as to confer maximal/complete hepatic functionality to the subject so as to maximally/completely treat a disorder amenable to treatment via hepatic transplantation in the subject.

It will be appreciated by the ordinarily skilled artisan that in order to confer hepatic functionality to, and thereby treat a disorder amenable to hepatic transplantation in, a subject by transplantation of a hepatic graft of the present invention into the subject, it is necessary to achieve as a result of such transplantation hematological vascularization of the graft so as to enable the graft-derived hepatic organ to develop and confer hepatic functionality to the subject.

With regard to achievement of hematological vascularization of a hepatic graft of the present invention, it is clearly shown in Example 6 of the following Examples section that a hepatic graft of the present invention, following transplantation thereof into a subject, has the inherent capacity to develop vasculature which is integrated into the vascular system of the subject, as evidenced by secretion of significant levels of graft-derived albumin into the serum of the subject. It will be appreciated that vascularization of a graft-derived hepatic organ may be augmented via any one of various standard vascular surgery techniques, as described below.

Following transplantation of a hepatic graft into a subject according to the present teachings, it is advisable, according to standard medical practice, to monitor the growth and differentiation of the hepatic graft and the hepatic functionality of the subject according to any one of various standard art techniques, and/or as described in the Examples section which follows. As described in Examples 5-8 of the Examples section below, the functionality of a hepatic graft of the present invention may be monitored following transplantation by standard liver function tests (e.g. analysis of serum levels of creatinine or bilirubin, and analysis of blood-clotting time). Structural development of the graft may be monitored via computerized tomography, or ultrasound imaging.

One of ordinary skill in the art, such as a surgeon specialized in liver transplantation, will possess the necessary expertise to adapt the teachings of the present invention so as to achieve treatment of a disorder amenable to treatment via hepatic transplantation in a human subject by transplantation of a hepatic graft of the present invention. Ample guidance is provided in the art for practicing therapeutic hepatic transplantation (refer, for example, to: Frilling A. et al. 2001. Current status of liver transplantation for treatment of hepatocellular carcinoma. Dig Dis. 19:333-7; Brandhagen D J., 2001. Liver transplantation for hereditary hemochromatosis. Liver Transpl. 7:663-72; Seaman D S., 2001. Adult living donor liver transplantation: current status. J Clin Gastroenterol. 33:97-106; Keeffe E B., 2000. Liver transplantation at the millennium. Past, present, and future. Clin Liver Dis. 4:241-55; Keeffe E B., 2000. Liver transplantation at the millennium. Past, present, and future. Clin Liver Dis. 4:241-55; Van Thiel D H. et al., 2001. Liver transplantation for fulminant hepatic failure. J. Gastroenterol. 36:1-4; and Keeffe E B., 2001. Liver transplantation: current status and novel approaches to liver replacement. Gastroenterology 120:749-62).

An exemplary scheme for performing hepatic transplantation in a human according to the teachings of the present invention is outlined in Example 8 of the Examples section below.

As described hereinabove, increased vascularization of a graft-derived renal or hepatic organ of the present invention may be achieved by surgically connecting the vasculature of the graft to a blood vessel of the subject. This may be achieved by suitably surgically anastomosing the vasculature of the graft-derived organ with that of the subject so as to achieve a desired perfusion of the former. Alternatively, a graft of the present invention may be connected to a blood vessel of the subject via a tube or canula, or, angioplasty can be used to widen a smaller blood vessel to which the graft is connected so as to achieve increased blood flow through the graft-derived organ.

Following transplantation of a graft of the present invention, the status of the immunological tolerance of the subject to the graft is preferably closely monitored according to standard art methods.

Various methods may be employed to assess the subject's immunological tolerance to the graft.

For example the tolerance may be assessed by monitoring subject specific leukocyte or T-lymphocyte specific infiltration of the graft, by monitoring the origin of the graft vasculature, and/or by monitoring the histological appearance of organ or tissue specific structures. Such monitoring may be advantageously effected as described in Examples 1-3 of the Examples section below, and/or according to standard art methods (refer, for example, to Dekel B. et al., 1999. Int Immunol. 11, 1673; Dekel B. et al., 1997. Transplantation 64, 1541). Infiltration of subject leukocytes, neutrophils, natural killer (NK) cells, or T-lymphocytes into the graft, or lack thereof, are typically indicative of suboptimal or optimal engraftment of the graft in the subject, respectively. Ample guidance for ascertaining graft rejection is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623). Infiltration of a graft by T-lymphocytes of a graft recipient typically correlates with graft rejection.

As described hereinabove, the method of treating the disorder may advantageously comprise treating the subject with an immunosuppressive regimen, prior to, during or following transplantation of the graft.

Various types of immunosuppressive regimens may be used to immunosuppress the subject.

Examples of suitable types of immunosuppressive regimens include administration of immunosuppressive drugs, tolerance inducing cell populations, and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994.

Am J. Med. 97, 14; Hanto DW., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the immunosuppressive regimen consists of administering at least one immunosuppressant drug to the subject.

Examples of suitable immunosuppressive drugs include, but are not limited to, CTLA4-Ig, anti-CD40 antibodies, anti-CD40 ligand antibodies, anti-B7 antibodies, anti-CD3 antibodies (for example, anti-human CD3 antibody OKT3), methotrexate (MTX), rapamycin, prednisone, methyl prednisolone, azathioprene, cyclosporin A (CsA), tacrolimus, cyclophosphamide and fludarabin, mycophenolate mofetil, daclizumab [a humanized (IgG1 Fc) anti-IL2R alpha chain (CD25) antibody], and anti-T-lymphocyte antibodies conjugated to toxins (for example, cholera A chain, or *Pseudomonas* toxin).

Preferably, the at least one immunosuppressant drug comprises at least one drug which is capable of blocking binding of a lymphocyte coreceptor with a cognate lymphocyte coreceptor ligand thereof, and more preferably further comprises rapamycin.

Preferably, the lymphocyte coreceptor is B7-1, CD40 and/or CD40L (CD40 ligand). It will be appreciated by the ordinarily skilled artisan that CD40+CD40L, and B7-1+CD28 are lymphocyte receptor-lymphocyte coreceptor ligand pairs.

Examples of suitable drugs capable of blocking binding of a lymphocyte coreceptor with a cognate lymphocyte coreceptor ligand include, but are not limited to, CTLA4-Ig, anti-CD40 antibodies, anti-CD40 ligand antibodies, anti-B7-1 or -2 antibodies, and anti-CD28 antibodies. CTLA4-Ig is a genetically engineered fusion protein of human CTLA4 and the IgG1 Fc domain. It prevents T-lymphocyte activation by binding to human B7, which costimulates T-lymphocytes through CD28.

Such polypeptide drugs are particularly advantageous since these are, unlike commonly used immunosuppressant drugs like cyclosporin A, essentially non-toxic and/or non-carcinogenic, and by virtue of passively blocking cell surface receptor interactions, afford reversible and temporary immunosuppression of the subject.

Preferably, the at least one drug which is capable of blocking binding of a lymphocyte coreceptor with a cognate lymphocyte coreceptor ligand thereof comprises CTLA4-Ig, and more preferably comprises CTLA4-Ig and anti-CD40L.

A drug which is capable of blocking binding of a lymphocyte coreceptor with a cognate lymphocyte coreceptor ligand thereof can be suitably administered to a subject of the present invention in any of various ways known in the art. For example, ample guidance for administering immunosuppressant drugs such as CTLA4-Ig so as to facilitate immunosuppression of a transplant recipient is provided in the literature of the art (for example, refer to: Benhamou P Y., 2002. Transplantation 73, S40; Najafian N, and Sayegh M H., 2000. Expert Opin Investig Drugs 9, 2147-57).

Preferably, treatment of a subject of the present invention with CTLA4-Ig is effected by administering CTLA4-Ig to the subject at a daily dose selected from a range of 1 to 100 milligrams per kilogram body weight, and most preferably about 20 milligrams per kilogram body weight.

As used herein the term "about" refers to ±10%.

Preferably, treatment of a subject of the present invention with anti-CD40L antibody is effected by administering anti-CD40L antibody to the subject at a daily dose selected from a range of 0.8 to 80 milligrams per kilogram body weight per day, and most preferably about 20 milligrams per kilogram body weight per day.

Preferably, treatment of a subject of the present invention with rapamycin is effected by administering rapamycin to the subject at a daily dose selected from a range of 0.0012 to 12 milligrams per kilogram body weight per day, more preferably 0.012 to 1.2 milligrams per kilogram body weight per day, and most preferably about 0.06 milligram per kilogram body weight per day.

As is described in the Examples section which follows transplantation of a porcine graft of the present invention into a mouse (average weight 25 grams) can be effectively performed by administering to the mouse daily doses of 250, 200 and 30 micrograms of CTLA4-Ig, anti-CD40L and rapamycin, respectively, which corresponds to daily doses of 10, 8 and 1.2 milligrams per kilogram body weight per day, respectively. As is established in the art, CTLA4-Ig, anti-CD40L antibody and rapamycin may be suitably employed in humans in the context of non-syngeneic transplantation at daily doses of 20, 20 and 0.06 milligrams per kilogram body weight per day. As is particularly described and illustrated in Example 3 of the Examples section which follows (e.g. refer to FIG. 15e), transplantation of a porcine renal graft of the present invention into a normal mammalian xenogeneic recipient minimally immunosuppressed via treatment with CTLA4-Ig, anti-CD40L antibody, and rapamycin according to the teachings of the present invention can be used to generate in the recipient well developed and tolerated graft-derived renal tissues. Similarly, as is particularly described and illustrated in Example 6 of the Examples section which follows (e.g. refer to FIGS. 21b-d, 22 and 23), transplantation of a porcine hepatic graft of the present invention into a normal mammalian xenogeneic recipient minimally immunosuppressed via treatment with CTLA4-Ig, anti-CD40L antibody, and rapamycin according to the teachings of the present invention can be used to generate in the recipient well developed and tolerated, functional graft-derived hepatic tissues.

Preferably a drug of the present invention which is capable of blocking binding of a lymphocyte coreceptor with a cognate lymphocyte coreceptor ligand thereof is administered to the subject during a time period having a duration selected from a range of 1 to 60 days, more preferably 1 to 50 days, more preferably 1 to 40 days, more preferably 1 to 30 days, more preferably 1 to 20 days, more preferably 1 to 10 days, and most preferably about 6 days.

Preferably a drug of the present invention which is capable of blocking binding of a lymphocyte coreceptor with a cognate lymphocyte coreceptor ligand thereof is administered to the subject at a frequency selected from a range of every 1 to 4 days, more preferably 1 to 3 days and most preferably every 2 days.

Preferably, rapamycin is administered to the subject at a frequency selected from a range of every 3 days, more preferably every 2 days, and most preferably every day. Rapamycin may advantageously be indefinitely administered to the subject, according to need, so as to optimally prevent graft-rejection.

Preferably, administering the at least one immunosuppressant drug to the subject is effected starting on the day of the transplanting.

While the disease treatment method of the present invention may be practiced to treat a disorder in a subject of essentially any mammalian species, the method is preferably used to treat the disorder in a human subject.

As mentioned hereinabove, the treatment method of the present invention can be used to treat essentially any disorder which is amenable to treatment via renal transplantation.

Examples of renal disorders which can be treated via the renal transplantation method of the present invention include, without limitation, acute kidney failure, acute nephritic syndrome, analgesic nephropathy, atheroembolic kidney disease, chronic kidney failure, chronic nephritis, congenital nephrotic syndrome, end-stage kidney disease, Goodpasture's syndrome, IgM mesangial proliferative glomerulonephritis, interstitial nephritis, kidney cancer, kidney damage, kidney infection, kidney injury, kidney stones, lupus nephritis, membranoproliferative glomerulonephritis I, membranoproliferative glomerulonephritis II, membranous nephropathy, necrotizing glomerulonephritis, nephroblastoma, nephrocalcinosis, nephrogenic diabetes insipidus, IgA-mediated nephropathy, nephrosis, nephrotic syndrome, polycystic kidney disease, post-streptococcal glomerulonephritis, reflux nephropathy, renal artery embolism, renal artery stenosis, renal papillary necrosis, renal tubular acidosis type I, renal tubular acidosis type II, renal underperfusion and renal vein thrombosis.

As mentioned hereinabove, the treatment method of the present invention can be used to treat essentially any disorder which is amenable to treatment via hepatic transplantation.

Examples of diseases which are amenable to treatment via hepatic transplantation include essentially all hepatic disorders, as well as essentially all deficiencies in a circulating enzyme which can be produced by a liver.

Examples of hepatic disorders which are amenable to treatment via hepatic transplantation include, without limitation, hepatitis C infection, hepatobiliary malignancies such as hepatocellular carcinoma (Molmenti E P, Klintmalm G B., 2001. J Hepatobiliary Pancreat Surg. 8:427-34), cirrhosis, primary sclerosing cholangitis (Crippin J S., 2002. Can J. Gastroenterol. 16:700), alcoholic liver disease (Podevin P. et al., 2001. J Chir (Paris). 138:147), hepatitis B (Samuel D., 2000. Acta Gastroenterol Belg. 63:197-9), drug/toxin-induced hepatotoxicity, hepatic vascular injury, autoimmune hepatitis, blunt hepatic trauma, liver damage associated with inborn errors of metabolism, urea cycle defects, hypercholesterolemia, glycogen storage disease, primary hyperoxaluria type I, cryptogenic cirrhosis, Crigler-Najjar syndrome type I, congenital hepatic fibrosis, Neimann-Pick disease, primary biliary cirrhosis, amyloidosis, biliary atresia, hepatoblastoma, Alagille syndrome, hemangioendothelioma, cholestasis, acute/fulminant liver failure, Budd-Chiari syndrome, alpha-1-antitrypsin deficiency, Wilson disease, hemochromatosis, tyrosinemia, disorders of porphyrin metabolism such as protoporphyria, cystic fibrosis, malignant neoplasm of intrahepatic bile ducts, lipidoses, disorders of copper metabolism, disorders of purine and pyrimidine metabolism, disorders of bilirubin excretion, mucopolysaccharidosis, congenital factor VIII disorder, congenital factor IX disorder, necrosis of liver, alcoholic fatty liver, sequelae of chronic liver disease, disorders of gallbladder, bile duct obstruction, biliary atresia, perinatal jaundice due to hepatocellular damage, portal vein thrombosis (PVT), hemophilia (Liu et al., 1994. Transpl Int. 7:201), and lysosomal storage diseases/enzyme deficiencies such as Gaucher disease (Groth C G. et al., Birth Defects Orig Artic Ser. 9:102-5).

While reducing the present invention to practice, organs/tissues at defined stages of differentiation corresponding to a specific gestational stage found not expressing or presenting a molecule capable of stimulating or enhancing an immune response prior to and/or following transplantation thereof into a recipient were unexpectedly revealed to be capable of generating structurally and functionally differentiated organs/tissues well tolerated by non syngeneic lymphocytes when transplanted into a subject.

Thus, according to a further aspect of the present invention there is provided a method of evaluating the suitability of a mammalian organ or tissue at a stage of differentiation corresponding to a specific gestational stage for transplantation of a graft of the organ or tissue into a mammalian subject.

The method according to this aspect of the present invention is preferably effected by evaluating a test transplant taken from the organ or tissue for expression or presentation of the molecule capable of stimulating or enhancing an immune response (hereinafter "the molecule") in the subject prior to and/or following transplantation of the test transplant into a mammalian test recipient.

According to the teachings of the present invention, a test transplant found not substantially expressing or presenting the molecule prior to and/or following transplantation of the test transplant into the test recipient will be optimal for transplantation. In general, the lower the level of expression or presentation of the molecule in the test transplant, the more suitable the organ or tissue graft will be for transplantation. In particular, the lower the level of expression or presentation of the molecule in the test transplant, the better the graft will structurally differentiate, functionally differentiate, and be tolerated by non syngeneic lymphocytes following transplantation into the subject.

It will be appreciated that since test transplants at stages of differentiation corresponding to various gestational stages can be tested for expression of the molecule, the method according to this aspect of the present invention enables identification of an optimal stage of differentiation of the organ or tissue for transplantation of a graft thereof into the subject.

According to the teachings of the present invention, testing the test transplant for the presence of the molecule is preferably effected prior to transplantation of the test transplant into the test recipient, and/or following a posttransplantation period selected from a range of 1 second to 45 days, depending on the type of molecule tested, as described in further detail hereinbelow.

The method according to this aspect of the present invention may be practiced using a test recipient of any of various mammalian species, and/or displaying any of various characteristics, depending on the application and purpose.

According to the teachings of the present invention, the test recipient is preferably a rodent, and/or the subject.

Preferably, the rodent is a mouse.

The use of a mouse as the test recipient is highly advantageous since this species, for numerous reasons, is by far the most convenient, economical, and effective experimental mammal available.

According to further teachings of the present invention, the test recipient bears human T lymphocytes.

Preferably, the human T lymphocytes are non syngeneic with the organ or tissue.

As is described and forcefully illustrated in Example 2 of the Examples section below, the method according to this aspect of the present invention may be effectively practiced by transplanting a human test transplant into a test recipient bearing human T lymphocytes non syngeneic with the organ or tissue.

Hence, the method according to this aspect of the present invention may be utilized to determine a stage of differentiation or gestation of a human organ or tissue optimal for transplantation of such an organ or tissue into an allogeneic human subject.

Thus, the method of evaluating the stage of differentiation of a graft most suitable for transplantation of the present invention is unique and optimal relative to all such prior art methods, and may be conveniently used to identify the stage of differentiation or gestation of essentially any organ or tissue type optimally suitable for therapeutic transplantation of a graft thereof into a human.

Although the method according to this aspect of the present invention may be practiced using a graft derived from essentially any mammalian species, the organ or tissue is preferably a porcine organ or tissue, more preferably a human organ or tissue.

According to the teachings of the present invention, the method according to this aspect of the present invention may be advantageously effected using a human organ or tissue at a specific stage of differentiation selected corresponding to 5 to 16 weeks of gestation, more preferably 6 to 15 weeks of gestation, more preferably 7 to 14 weeks of gestation, more preferably 7 to 9 weeks of gestation, and most preferably 8 weeks of gestation.

As is described and illustrated in Example 2 of the Examples section below, the method according to this aspect of the present invention may be effectively practiced using a human organ or tissue at a stage of differentiation corresponding to 8 weeks of gestation.

Alternately, the method according to this aspect of the present invention may be advantageously effected using a porcine organ or tissue at a specific stage of differentiation selected corresponding to 20 to 63 days of gestation, more preferably 20 to 56 days of gestation, more preferably 20 to 42 days of gestation, more preferably 20 to 35 days of gestation, more preferably 20 to 28 days of gestation, more preferably 24 to 28 days of gestation, and most preferably 27 to 28 days of gestation.

The method of evaluating the stage of differentiation of a graft suitable for transplantation of the present invention may be effected by testing the test graft for any of various types of molecules capable of stimulating or enhancing an immune response in the subject.

Examples of such types of molecules include cytokines, chemokines, inflammatory mediators, immune cell receptors, immune cell coreceptors, MHC molecules, antigen-presenting molecules, adhesion molecules, innate immunity mediators, apoptosis mediators, metalloproteinases, immunomodulators, lymphocyte coreceptors and lymphocyte coreceptor ligands.

Preferably, a graft suitable for transplantation does not substantially express or present a lymphocyte coreceptor or lymphocyte coreceptor ligand.

Examples of such lymphocyte coreceptors and lymphocyte coreceptor ligands include CD28, B7-1 (CD80), B7-2 (CD86), CD40, CD40L (CD40 ligand, CD154), CD2, CD58 [lymphocyte function associated antigen-3 (LFA-3)], intercellular adhesion molecule-1 (ICAM-1) and lymphocyte function associated antigen-1 (LFA-1).

Preferably, a graft suitable for transplantation does not substantially express or present B7-1, more preferably CD40 or CD40L, more preferably CD40 and CD40L, and most preferably B7-1, CD40, and CD40L.

As mentioned hereinabove, testing the test transplant for the presence of the molecule is preferably effected prior to transplantation of the test transplant into the test recipient, and/or following a posttransplantation period selected from a range of 1 second to 45 days, depending on the type of molecule tested.

Preferably, testing the test transplant for the presence of CD40 or CD40L is effected both prior to and following transplantation of the test transplant into the test recipient.

Preferably, testing the test transplant for the presence of CD40 following transplantation of the test transplant into the test recipient is effected following a test transplant posttransplantation period selected from a range of 1 second to 45 days, more preferably 11 days to 45 days, more preferably 11 days to 42 days, more preferably 11 days to 31 days, and most preferably 14 days to 28 days.

Preferably, testing the test transplant for the presence of CD40L following transplantation of the test transplant into the test recipient is effected following a test transplant posttransplantation period selected from a range of: 1 second to 45 days; more preferably 11 days to 45 days; more preferably 14 days to 45 days; more preferably 14 days to 31 days; more preferably 17 days to 31 days or 14 days to 28 days; more preferably 25 days to 31 days; more preferably 27 days to 29 days; more preferably 27.5 days to 28.5 days; and most preferably 28 days.

Preferably, testing the test transplant for the presence of B7-1 is effected prior to transplantation of the test transplant.

As is described and shown in Example 1 of the Examples section below, grafts not substantially expressing B7-1, CD40, and CD40L at the respective optimal test transplant pretransplantation/posttransplantation periods set forth hereinabove are suitable for transplantation. In particular, such grafts can generate structurally and functionally differentiated organs/tissues which are well tolerated by non syngeneic/alloreactive human lymphocytes.

While not being bound by a paradigm, the present inventors are of the opinion that a graft which does not substantially express or present such molecules, which are major antigen presenting cell specific molecules, is well tolerated by an allogeneic or xenogeneic subject at least partly as a result of such grafts substantially lacking antigen presenting cells which have been proposed in the art as being critical for activation of graft rejection.

Numerous methods, well known to the ordinarily skilled artisan, may be used to analyze an organ, a tissue or cells, such as the test graft or a portion thereof, for expression or presentation of a specific molecule.

In cases where the molecule is a protein or RNA molecule, expression or presentation of the molecule is preferably evaluated by analysis of cells or tissues for the presence of mRNA encoding the protein molecule, or for the presence of the RNA molecule, respectively.

Analysis of an mRNA or RNA molecule in cells or tissues is preferably effected by RT-PCR analysis. RT-PCR analysis may be advantageously performed as described and illustrated in Example 1 of the Examples section, below. Alternately, analysis of the presence of an mRNA or RNA molecule in cells can be performed by modifications of the RT-PCR protocol described in Example 1 of the Examples section, below (e.g. using a nested PCR phase, competitive RT-PCR, etc.), by Northern blotting, or by microarray analysis.

Alternately, expression or presentation of the protein molecule can be directly detected by directly detecting the protein molecule using various biochemical techniques.

Various methods of detecting expression or presentation of a specific protein in an organ, tissue, or cells are well known to those of ordinary skill in the art. Such methods include immunofluorescence flow cytometry, Western immunoblotting analysis, fluorescence in situ hybridization (FISH), enzyme linked immunosorbent assay (ELISA), microarray hybridization, immunofluorescence confocal microscopy, and the like.

In cases where the molecule is a protein, expression or presentation of both the molecule as well as mRNA encoding the molecule are tested.

In cases where the molecule is a protein, an optimal graft is one which does not substantially express the molecule, more preferably mRNA encoding the molecule, or most preferably both the molecule and mRNA encoding the molecule.

According to the teachings of the present invention, evaluating the suitability of the graft for transplantation may advantageously comprise analyzing grafts for expression or presentation of substantially lower levels than adult stage graft type organs/tissues of the immunity related molecules listed in Table 3 of the Examples section below and on the World Wide Web/Internet (http://www.weizmann.ac.il/immunology/reisner/immunogenicity.xls).

As is described and illustrated in Example 2 of the Examples section below, grafts expressing substantially lower levels of such immunity related molecules than adult stage graft type organs/tissues are more suitable for transplantation than the latter. A graft which expresses or displays substantially lower levels than adult stage organs/tissues of graft organ tissue type of the greatest possible number of such immunity related molecules may be optimally suitable for transplantation.

Preferably, analysis of expression or presentation of such immunity related molecules in the graft is effected by microarray hybridization analysis of graft derived mRNA, preferably as described and illustrated in Example 1 of the Examples section, below.

Alternately, analysis of expression or presentation of such immunity related molecules in the graft may be effected using any of the analytic techniques described hereinabove for analysis of the graft for expression or presentation of the molecule capable of stimulating or enhancing an immune response in the subject.

The method of the present invention of evaluating the suitability of a graft for transplantation is clearly novel and non-obvious over the prior art, including over each of the prior art references: U.S. Pat. No. 5,635,365 to Ansari et al. (hereinafter the patent), U.S. Pat. No. 6,194,147 to Baxter-Lowe et al. (hereinafter the '147 patent), and U.S. Pat. No. 6,183,734 to Chen et al (hereinafter the '734 patent).

The '365 patent teaches a method of predicting the risk of rejection of a graft via analysis in cells of the recipient of expression levels of hypoxanthine-guanine phosphoribosyltransferase (HPRT), a non-transmembrane receptor intracellular metabolic enzyme. In critically sharp contrast, however, the method according to this aspect of the present invention teaches a method of evaluating the transplantation suitability of a graft via analysis in the graft of expression levels of a lymphocyte coreceptor or of a lymphocyte coreceptor ligand, such as B7-1, CD40 and CD40L. Thus, since the method according to this aspect of the present invention is effected via completely distinct method steps, i.e. via analysis of the graft, as opposed to analysis of the recipient, and via analysis of structurally and functionally distinct types of molecules, i.e. cell surface/immune receptors, as opposed to intracellular metabolic enzymes, the method according to this aspect of the present invention is clearly novel and non-obvious over the '365 patent.

The '147 patent teaches a method of characterizing HLA DNA of a potential graft donor to assess the absolute genetic suitability of a graft therefrom for transplantation into a recipient, regardless of the developmental stage of the potential graft donor. In critically sharp contrast, however, as described above, the method according to this aspect of the present invention teaches a method of evaluating the developmental stage suitability of a graft of any HLA haplotype for transplantation into a recipient via analysis of the graft for expression or presentation of molecules such as B7-1, CD40 and/or CD40L, whose expression levels, as taught for the first time in the present specification, vary according to developmental stage, and whose expression levels correlate with transplantation suitability of the graft. The novelty and non-obviousness of the method according to this aspect of the present invention can be illustrated, for example, by the fact that it provides a novel method of selecting an optimal graft for transplantation from among a set of identical grafts which share an HLA haplotype selected as optimal for transplantation, but which differ only with respect to their developmental stage. As such the method according to this aspect of the present invention has a clearly distinct utility from that of the '147 patent.

Thus, the method according to this aspect of the present invention is clearly novel and non-obvious over the '147 patent since: (i) it is effected by characterizing a variable physiological characteristic, i.e. analysis of expression levels of messenger RNA or protein molecules, as opposed to characterization of a DNA molecule, which is an unchangeable characteristic, and which may or may not be functionally expressed in a given graft; (ii) it is effected by characterizing molecules such as B7-1, CD40 and/or CD40L, which are structurally and functionally distinct from HLA molecules; and (iii) it has a distinct utility from that of the method taught by the '147 patent.

The '734 patent teaches a method of treating cancer effected by genetically modifying tumor cells of a subject to express the molecule B7, and reintroducing the genetically modified cells into the subject so as to induce anticancer immunity therein. Thus, the method according to this aspect of the present invention is clearly novel and non-obvious over the '734 patent simply due to its being drawn to an invention which is practiced completely distinctly from, and is only tangentially related to, the '734 patent, since it teaches a method of evaluating the transplantation suitability of a graft effected by analyzing expression levels of molecules such as B7 in the graft.

Furthermore, unlike the present specification which provides such unpredictable teachings for the first time, the '734 patent critically does not demonstrate, suggest, imply nor in any way teach, that:

(i) expression levels of molecules such as B7, CD40 or CD40L in a tissue vary according to gestational stage, as taught herein for the first time; and (ii) there exists a developmental stage threshold prior to which a tissue concomitantly expresses undetectable levels of such molecules, and that such expression levels can be used as a correlative indicator that the tissue is at a gestational stage optimally suitable for transplantation, as further taught herein for the first time.

Furthermore, while the '734 patent teaches that inducing, via genetic modification, abnormally high-level overexpression of B7 in cancer cells obtained from a subject can elicit immune responses against such cells following their reintroduction into the subject, this patent does not teach that normal physiological levels of B7 in such a cancer treatment context, and all the more so in the present non-syngeneic graft transplantation context, can result in elicitation of relevant immune responses. In sharp and critical contrast, the method according to the present invention provides teachings relating to threshold and normal physiological expression levels of molecules such as B7, CD40 or CD40L.

Moreover, the ordinarily skilled artisan would not consider that immune mechanisms occurring in the cancer physiology context between immune cells and syngeneic genetically modified cancer cells expressing abnormally high levels of a heterologous molecule such as B7 would be reasonably expected to be recapitulated between normal, gestational stage cells expressing physiologically normal threshold levels of such molecules in the non-syngeneic transplantation context of the present specification. As such, absent the novel and unpredictable teachings of the present specification, the ordinarily skilled artisan would not be motivated to practice the method according to this aspect of the present invention.

Thus, the method of evaluating the transplantation suitability of a graft of the present invention is clearly novel and non-obvious over the '734 patent.

Thus, the present invention provides for the first time grafts of porcine or human, renal or hepatic, organs/tissues which can be transplanted into a minimally immunosuppressed allogeneic/xenogeneic mammalian host so as to generate therein, in the absence of graft-derived teratoma formation, well developed and tolerated functional renal or hepatic organs/tissues, respectively. As such, the present invention provides novel and urgently needed renal or hepatic grafts which are suitable for therapeutic transplantation for treatment of diseases amenable to renal or hepatic transplantation. By virtue of providing grafts which do not need to be HLA-compatible with a recipient thereof, the transplantation methods of the present invention critically circumvent the prior art disadvantages of requiring HLA-compatible grafts. Furthermore, by virtue of requiring minimal graft recipient immunosuppression, the transplantation method of the present invention overcomes the prior art requirement for permanent administration of harmful immunosuppressants to graft recipients to prevent graft rejection. Additionally, by virtue of providing developing/animal grafts which are suitable for therapeutic transplantation into humans, the present invention provides a transplantation method which employs grafts which are in essentially limitless supply, and which thereby overcomes the disadvantages of prior art methods employ from human donors which are in critically limited supply and whose harvesting is associated with significant ethical and medical burdens.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

General Materials and Methods—Transplantation of Developing Renal Grafts

Preparation of Immunodeficient Mouse Hosts Bearing Human Leukocytes: Three month old Balb/c mice (Harlan Olac, Shaw's Farm, Blackthorn, Bicester, Oxon., UK) were subjected to the immune-modification procedure described hereinbelow to replace their leukocytes with human leukocytes, and were used as hosts for the transplantation studies. Balb/c mice were lethally irradiated by split-dose total body irradiation (TBI; 3.5 Gy followed 3 days later by 9.5 Gy) by a 150-A (60) Co gamma ray source (produced by the Atomic Energy Commission of Canada, Kanata, Ontario) with a focal skin distance of 75 centimeters and a dose rate of 0.7 Gy/minute, as previously described (Lubin I. et al., 1994. Blood 83, 2368; Reisner, Y. and Dagan, S., 1998. Trends Biotechnol. 16, 242-246; Segall, H. et al., 1996. Blood 88, 721-730). Bone marrow cells from NOD/SCID mice (Weizmann Institute Animal Breeding Center, Rehovot, Israel) were flushed from femur and tibia shafts of 4- to 8-week old mice, as previously described (Levite M. et al., 1995. Cell Immunol. 162, 138). Recipient Balb/c mice were immune-reconstituted with 3 million bone marrow cells from NOD/

SCID mice administered intravenously in 1 milliliter phosphate buffer saline solution one day following the second fraction of total body irradiation (TBI), as previously described (Reisner, Y. and Dagan, S., 1998. Trends Biotechnol. 16, 242-246; Segall, H. et al., 1996. Blood 88, 721-730). The resulting SCID (severe combined immunodeficiency) mouse-like animals have been shown to allow excellent engraftment of functioning human hematopoietic cells or solid tissues (Marcus H. et al., 1995. Blood 86, 398; Segall H. et al., 1996. Blood 88, 88; Reisner Y. and Dagan S., 1998. Trends Biotechnol. 16, 242; Bocher W O. et al., 2001. Eur J. Immunol. 31, 2071). Donor NOD/SCID mice were obtained from the Weizmann Institute Animal Breeding Center, Rehovot, Israel, and animal experiments were carried out according to the National Institutes of Health Guide for Care and Use of Experimental Animals and approved by the Weizmann Institute of Science Animal Care Committee.

One to three days following transplantation of renal tissue, 100 million human peripheral blood mononuclear cells (PBMCs) were injected intraperitoneally in host mice. Control mice did not receive human PBMCs. Generation of human PBMCs, their infusion into recipient mice, and analysis of engraftment of infused cells were performed as previously described (Segall, H. et al., 1996. Blood 88, 721-730). Human PBMCs were generated from buffy coats obtained from normal volunteers, as follows. Blood samples were overlayed on a cushion of Lymphoprep solution (Nycomed, Oslo, Norway) and centrifuged at 2,000 rpm for 20 minutes. The interface layer was collected and washed twice, and the cells were counted and resuspended in phosphate buffer saline solution (pH 7.4) at the desired concentration. For analysis of human lymphocyte engraftment, cells were recovered from peritonea 10 to 14 days following PBMC infusion. Single-cell suspensions were incubated for 30 minutes on ice with labeled anti-human CD3-PE and CD45-PerCP (pan-human leukocyte antigen) antibodies (Becton-Dickinson, Mountain View, Calif.). After washing, two- or three-color fluorescent analysis of these human antigens was performed using a FACScan analyzer (Becton-Dickinson). Data was collected from lymphocytes selectively gated via standard forward- and side-scatter characteristics. In certain experiments, dual PBMC infusions from separate human donors were administered to graft recipient mice.

Transplantation of developing renal tissue: Transplantation of human renal tissue under the renal capsule of recipient mice was performed as previously described (Dekel, B. et al., 1997. Transplantation 64, 1541-1550). Whole-organ human renal grafts at a gestational stage of up to 56 days, or whole or 1-2 mm-diameter fragments of renal tissues at later stages of gestation were used in transplantations. For analysis of growth, development and teratoma formation capacity, developing renal tissues were transplanted into NOD/SCID recipient mice. For immunogenicity assays, developing renal grafts were tested in the presence or absence of human PBMC. There, transplantation of renal tissues into Balb/c recipients was performed 7-10 days following reconstitution of irradiated Balb/c hosts with NOD/SCID bone marrow, in the presence or absence of human PBMCs. Transplantation was performed 7-10 days following reconstitution of irradiated hosts with NOD/SCID bone marrow. For growth assays, renal tissues were transplanted into SCID recipient mice. For transplantation, renal tissues were maintained in sterile conditions at 4 degrees centigrade for approximately two hours in either RPMI 1640 or Dulbecco's modified Eagle's medium supplemented with 10 percent fetal calf serum (FCS; Biological Industries, Beit Haemek, Israel). Transplantation of renal tissues was performed under general anesthesia induced by intraperitoneal injection of 2.5 percent Avertin in phosphate buffer saline solution (10 milliliters per kilogram body weight). Both host kidneys were exposed via a bilateral incision, a 1.5 mm incision was made at the caudal end of the renal capsule, and an approximately one cubic millimeter fragment of renal tissue was implanted under each renal capsule. Renal tissues were also transplanted intra-abdominally to control for renal subcapsular space-specific immune privilege. In some experiments, renal tissues were implanted and sutured (5-0 suture) onto the testicular fat pad in conjunction with a left nephrectomy. Transplanted mice were treated postoperatively with ciprofloxacin in their drinking water for 7 days.

Analysis of graft infiltration, growth and differentiation: Human immune cell infiltration as well as growth and development of renal graft derived tissues, glomeruli and tubuli were monitored following transplantation, as follows. Graft recipients were sacrificed 4-10 weeks posttransplantation, as indicated. Recipient kidneys and their capsules were then removed and fixed in 10 percent paraffin. Transplants were sectioned and mounted on slides coated with poly-L-lysine and sections were stained with hematoxylin and eosin (H&E). To determine growth of grafts from time of transplantation to time of harvest, the sizes of the graft pretransplant and at time of harvest (posttransplant) were measured, and posttransplant to pretransplant graft size ratios were calculated. Graft size was determined according to the formula graft size=L×W, where L and W represent the long and short axes of the graft, respectively. Assessment of graft development was performed by counting the number of mature glomeruli and tubuli in 10 consecutive microscopic fields (×40 magnification) per transplant in 3 transplants per group. Determination of human T-lymphocyte infiltration in graft sections was determined as previously described (Naveh M T. et al., 1992. J Clin Invest. 90, 2434). Briefly, graft sections were immunostained with rabbit anti-human CD3 antibody (Zymed, San Francisco, Calif.; pan T-lymphocyte), as previously described (Dekel, B. et al., 1999. Int. Immunol. 11, 1673-1683), and the number of human CD3 positive cells was counted in 10 consecutive microscopic fields (×100 magnification) per transplant in 3 transplants per group. Paraffin tissue blocks of transplants were cut 4-6 microns thick, deparaffinized in xylene, rehydrated and placed for 15 minutes in ethanol containing 3 percent hydrogen peroxide to block endogenous peroxidase. Slides were thoroughly washed with tap water and transferred to phosphate-buffered saline (PBS) solution. Sections were then treated with 1 percent bovine serum albumin (BSA) to prevent background staining and incubated for 1 hour with anti-CD3 antibody at room temperature in a humidified chamber. Slides were rinsed with PBS solution for 3 minutes, incubated with biotinylated anti-rabbit antibody for 30 minutes, and then incubated with peroxidase-conjugated streptavidin (StrAvigen; Biogenex, San Ramon, Calif.) for 30 minutes. After rinsing, the peroxidase label was visualized by incubation with 3-amino-9-ethylcarbazol (AEC) for 15 minutes and counterstained with Mayer's hematoxylin using an immunohistochemical staining kit (Biomeda, Foster City, Calif.), according to the manufacturer's instructions. The AEC reagent produces a red product that is soluble in alcohol and can be used with an aqueous mounting medium (Kaiser's glycerol gelatin). A negative control for staining of T-lymphocytes was performed by following all of the aforementioned steps but omitting addition of primary antibody. Staining was found to be uniformly negative in transplants from control mice not infused with human PBMCs.

Analysis of host-specific graft vasculogenesis: Five micron-thick paraffin sections of grafts were immunostained with a rat anti-mouse PECAM-1 antibody (Pharmingen, San Diego, Calif.) using a Histostain Plus kit (Zymed, San Francisco, Calif.), according to the manufacturer's instructions. Vessel counts were performed in similar regions within renal grafts (5 consecutive high-power magnification fields per transplant in 5 transplants per group).

Urine collection and analysis: Fluid produced by graft-derived organs was collected and analyzed for urinary marker content, as follows. Developing human and porcine transplants were surgically exposed in anesthetized mice via midline or left flank incision and a plastic microcatheter was inserted into an identifiable area of fluid concentration. At the site of insertion, the graft walls were sutured around the catheter using a 5-0 nylon suture, and fluid from the graft was collected via the microcatheter into small-volume PCR tubes sutured onto the skin of the mice. The drained fluid was subsequently analyzed for urea nitrogen and creatinine concentrations.

Statistical analysis: Comparisons between groups were evaluated by the Student's t-test. Data were expressed as mean±s.e.m., and were considered statistically significant if P values were 0.05 or less.

Example 2

Human 49- to 56-Day Gestational Stage Renal Grafts, Unlike Later-Stage Grafts, have the Capacity to Generate, in the Absence of Teratoma Formation, Well Developed and Tolerated Functional, Urine Producing Renal Organs Following Transplantation into Immunodeficient Mice Introduction: Renal allograft transplantation is presently by far the optimal therapeutic option for renal failure, a highly debilitating and potentially fatal medical condition of significant morbidity. Such transplantation, however, is often impossible to implement due to the difficulty of finding a haplotype-matched kidney donor. Moreover, even when a matched kidney donor is found, allogeneic transplantation is associated with significant drawbacks, such as the requirement for permanent administration of toxic, immunosuppressive drugs such as cyclosporin A to prevent graft rejection. Thus, there exists an urgent need for novel sources of renal grafts suitable for therapeutic transplantation in humans. A potentially optimal strategy for renal allograft transplantation would be to use gestational stage renal allografts, since it has been demonstrated that the earlier the developmental stage of allografts, the less vigorously such a graft tends to be rejected following transplantation into an allogeneic host. However, to date, the hypothetical existence of specific gestational stages during which human renal allografts are sufficiently differentiated so as to generate functional renal organs without, or with minimal, risk of teratoma formation, while at the same time being sufficiently undifferentiated so as to display significantly reduced immunogenicity relative to adult-stage grafts following transplantation has yet to be confirmed. While reducing the present invention to practice, such critical limitations of the prior art were overcome, as described below.

Materials and Methods:

Preparation of mouse graft hosts: refer to Example 1, "General Materials and Methods—Transplantation of developing renal grafts", above.

Harvesting of developing renal tissue: Gestational stage human renal tissues were obtained by curettage with the approval of a Helsinki committee and were surgically dissected from embryos under a dissection stereoscope as previously described (Rogers S. et al., 1998. Kidney Int. 54, 27). Adult kidney specimens were obtained from normal kidneys removed for stage I clear cell carcinoma. All specimens for gene expression analysis were snap-frozen in liquid nitrogen. Tissues for transplantation were kept in sterile conditions at 4° C. (for approximately 2 hours) in either RPMI 1640 or Dulbecco's modified Eagle's medium (DMEM) supplemented with 10 percent fetal calf serum (Biological Industries, Beit HaEmek, Israel).

Transplantation of developing renal tissue: Refer to Example 1, "General 97 Materials and Methods—Transplantation of developing renal grafts", above. Whole human renal organ precursors at a gestational stage of up to 56 days, or whole or 1-2 mm-diameter fragments of renal tissues at later stages of gestation were used in transplantations.

Analysis of graft infiltration, growth and differentiation: refer to Example 1, "General Materials and Methods—Transplantation of developing renal grafts", above.

Analysis of host-specific graft vasculogenesis: refer to Example 1, "General Materials and Methods—Renal Grafts", above.

Urine collection and analysis: refer to Example 1, "General Materials and Methods—Transplantation of developing renal grafts", above.

RT-PCR analysis of costimulatory molecule expression in grafts: Messenger RNA from 56-, 98-, and 154-day gestational stage renal tissue-derived grafts was analyzed via RT-PCR at the following time points: (i) prior to transplantation; (ii) immediately following transplantation but prior to infusion of alloreactive human PBMCs; and (iii) 2, 4, and 6 weeks following reconstitution of mice with human PBMCs, as follows. Grafts were carefully dissected from the subcapsular implantation site and total RNA was isolated from the dissected grafts as previously described (Dekel, B. et al., 1999. Int. Immunol. 11, 1673-1683). Briefly, the renal graft tissues were homogenized with a glass-Teflon tissue homogenizer in Tri-reagent (Molecular Research Center Inc., Cincinnati, Ohio) for isolation of total RNA, according to the manufacturer's instructions. The isolated RNA was air-dried, resuspended in nuclease-free water and quantified by spectrophotometry. Aliquots of 1 microgram of total RNA preparation were reverse-transcribed into cDNA with AMV reverse transcriptase using an Access RT-PCR kit (Promega Corp., Madison, Wis.), according to the manufacturer's instructions. Sequences specific to the costimulatory molecules and to the control housekeeping gene β-actin (Pratt, J. R. et al., 2002. Nature Med. 8, 582-587) were subsequently PCR amplified from the synthesized cDNA. Briefly, reverse transcription cDNA product was diluted 1:50, 1:100, and 1:500 in sterile water and PCR amplification was performed using thermostable Tfl DNA polymerase in a 50 microliter reaction mixture containing 40 micromolar of each dNTP, 0.4 micromolar of each primer (Table 1), 10 millimolar Tris HCl (pH 8.3), and 1.5 millimolar $MgCl_2$. Each sample was tested at least three times, and compared tissue samples were PCR-amplified in parallel using a single master reagent mix.

TABLE 1

Oligonucleotide primers used for PCR amplification of cDNA prepared from human developing renal tissues.

| Amplified sequences | Oligonucleotide primers* (sense/antisense) | | PCR product length (bp) |
|---|---|---|---|
| B7-1 | 5'-GACCAAGGAAGTGAAGTGGC-3' | (SEQ ID NO: 1)/ | 410 |
| | 5'-AGGAGAGGTGAGGCTCTGGAAAAC-3' | (SEQ ID NO: 2) | |

TABLE 1-continued

Oligonucleotide primers used for PCR amplification of cDNA
prepared from human developing renal tissues.

| Amplified sequences | Oligonucleotide primers* (sense/antisense) | | PCR product length (bp) |
|---|---|---|---|
| B7-2 | 5'-CACTATGGGACTGAGTAACATTC-3' | (SEQ ID NO: 3)/ | 383 |
|  | 5'-GCACTGACAGTTCAGAATTCATC-3' | (SEQ ID NO: 4) |  |
| CD40 | 5'-CTCTGCAGTGCGTCCTCTGGGG-3' | (SEQ ID NO: 5)/ | 410 |
|  | 5'-GATGGTATCAGAAACCCCTGTAGC-3' | (SEQ ID NO: 6) |  |
| CD40L | 5'-TATCACCCAGATGATTGGGTCAGC-3' | (SEQ ID NO: 7)/ | 349 |
|  | 5'-CCAGGGTTACCAAGTTGTTGCTCA-3' | (SEQ ID NO: 8) |  |
| HLA-DR | 5'-ATGAAGGTCTCCGCGGCAGCCC-3' | (SEQ ID NO: 9)/ | 215 |
|  | 5'-CTAGCTCATCTCCAAAGAGTTG-3' | (SEQ ID NO: 10) |  |
| β-actin | 5'-ACCATCAAGCTCTGCGTGACTG-3' | (SEQ ID NO: 11)/ | 310 |
|  | 5'-GCAGGTCAGTTCAGTTCCAGGTC-3' | (SEQ ID NO: 12) |  |

*Homology searches for all primer sequences were performed using the NCBI's GenBank database to ensure non-specificity of primers for mouse genes.

In order to minimize non-specific amplification of non-target sequences, the PCR annealing temperature was set high (64 degrees centigrade), and, in order to detect PCR signals in the linear phase of product amplification, the PCR reaction was performed with 20 to 35 thermal cycles. In all experiments the possibility of amplification from contaminating DNA was ruled out via control reactions using reverse transcription reactions in which reverse transcriptase or template cDNA was omitted. PCR reaction products were separated electrophoretically in 1.5 percent agarose gels, the gels were stained with ethidium bromide and photographed using a UV transilluminator, as previously described (Sharma V K. et al., 1996. Transplantation 62, 1860).

Statistical analysis: Refer to Example 1, "General Materials and Methods—Transplantation of developing renal grafts", above.

Microarray analysis: Labeled cRNA preparation and hybridization to a Genechip Human Genome HU95A array (Affymetrix) was performed as recommended by the microarray manufacturer. Analysis of Genechip data was performed as previously described (Zuo, F. et al., 2002. Proc. Natl. Acad. Sci. USA 99, 6292-6297; Kaminski, N. et al., 2000. Proc. Natl. Acad. Sci. USA 97, 1778-1783). For cluster analysis CLUSTER, GENE CLUSTER, and TREEVIEW programs (Eisen, M. B. et al., 1998. Proc. Natl. Acad. Sci. USA. 95, 14863-14868) and the SCOREGENE software package (http://FGUSheba.cs.huji.ac.il/) were used. Fold ratios were calculated for each sample against the geometric mean of all the samples. A detailed description of the scoring methods and the approach used for analysis of microarray data have been published (Kaminski N. and Friedman N., 2002. Am. J. Respir. Cell Mol. Biol. 27, 125-132).

Experimental Results:

Human renal grafts at a gestational stage of 49 to 56 days, unlike later-stage grafts, have the capacity to generate, in the absence of teratoma formation, well developed and tolerated functional renal organs following transplantation into immunodeficient mice: To assess the influence of developmental stage of human renal grafts on growth, and renal differentiation, human renal grafts at developmental stages ranging from 49 to 98 days of gestation were transplanted into immunodeficient mouse recipients, and the grafts were analyzed 8 weeks posttransplantation. As can be seen in Table 2, whole organ precursor grafts at gestational stages of 49 and 56 days (n=8) unexpectedly, and uniquely relative to grafts at later gestational stages, underwent remarkable growth (transplant size ratio was 20.1±2.7), displayed complete nephrogenesis [5.5±0.8 glomeruli and 19.3±2.7 tubuli per field (×40 original magnification)], and exhibited no teratoma formation. The renal differentiation observed was very significant since at the time of transplantation such grafts contained mainly metarenal mesenchymal stem cells and ureteric buds, in the absence of glomeruli.

The gross morphology and histological appearance of 56-day gestational stage human renal grafts, 8 weeks post-transplantation are shown in FIGS. 1a-b, respectively. Beyond the 56-day gestational stage time point, transplantation of developing whole fetal kidneys resulted in central graft necrosis and viability was reduced. Therefore small pieces of human fetal renal tissue were grafted into host animals, as previously described (Dekel, B. et al., 1997. Transplantation 64, 1550-1558; Dekel, B. et al., 2000. Transplantation 69, 1470-1478). Under identical conditions, sections of transplants derived from 10- and 98-day gestational stage tissues (n=14) had significantly lower transplant size ratios (14.8±2.2 and 12.3±1.8, respectively, P<0.01) as well as glomerular and tubular counts (4.2±0.8 and 15.3±2.7; 3.5±0.8 and 11.2±2.2 per high-power field (HPF), respectively; P<0.05), relative to 49- to 56-day gestational stage grafts. Therefore, human 49- to 56-day gestational stage renal tissues possess uniquely optimal characteristics for transplantation into allogeneic recipients relative to grafts at different developmental stages.

TABLE 2

Development of human renal grafts at various gestational stages
following transplantation into immunodeficient mice.

| Gestational stage of graft (days) | No. of transplants | Graft | Incidence of graft growth* | Incidence of graft renal differentiation** | Incidence of non-renal differentiation | Incidence of necrosis |
|---|---|---|---|---|---|---|
| 98 | 3 | whole | 3/3 | none | none | 3/3 |
|  | 8 | fragment | 7/8 | 7/7 | none | none |

TABLE 2-continued

Development of human renal grafts at various gestational stages following transplantation into immunodeficient mice.

| Gestational stage of graft (days) | No. of transplants | Graft | Incidence of graft growth* | Incidence of graft renal differentiation** | Incidence of non-renal differentiation | Incidence of necrosis |
|---|---|---|---|---|---|---|
| 70 | 2 | whole | 2/2 | none | none | 2/2 |
|  | 6 | fragment | 6/6 | 6/6 | none | none |
| 56 | 5 | whole | 5/5 | 5/5 | none | none |
| 49 | 3 | whole | 3/3 | 3/3 | none | none |

*Transplant growth and differentiation were assessed at 8 weeks posttransplantation.
**Differentiation was categorized as renal (only nephrons), non-renal (differentiated derivatives other than renal) and necrosis (in addition to nephrons, appearance of necrotic areas mostly in center of transplant).
In a control experiment, all adult-stage human renal grafts (5/5) were found to generate sclerotic and non-viable tissues when analyzed at 8 weeks posttransplantation.

Host-derived vascularization of transplanted human 49- to 56-day gestational stage renal grafts is associated with enhanced tolerance for such grafts by immunodeficient host mice: The ability of transplants to grow as tissues in non-syngeneic hosts depends primarily on their ability to sustain angiogenesis in such hosts (Gritsch, H. A. et al., 1994. Transplantation 57, 906-917). To determine the ability of recipient mice to support angiogenesis of avascular human 56-day gestational stage renal grafts by ingrowth of host-derived blood vessels, expression of mouse PECAM (CD31), a marker of sprouting endothelial cells, was immunohistochemically analyzed in the developing transplants. Counts of immunoreactive vessels reflecting the combined total number of capillary and larger vessels of host origin were performed per high power microscopic field, as previously described (Vermeulen, P. B. et al., 1996. Eur. J. Cancer 32A, 2474-2484). At 4 weeks posttransplantation, 23.5±4.0 vessels of host origin per high power microscopic field supplying the graft were found. In such 56-day gestational stage grafts, all larger vessels were positively stained positive for mouse CD31 (FIG. 2a). In addition, medium and small size capillaries of host origin were also detected in both glomeruli (FIG. 2b) and parenchyme (FIGS. 2c) of the gestational stage human renal transplants. In transplants of mature, vascularized 112-day gestational stage human renal tissues, there was a significantly reduced mouse CD31 positive vessel count (10.2±1.8, P<0.001) composed of mainly external larger vessels, but not endothelial cells in glomeruli and small capillaries (FIG. 2d). Negative control sections of vascularized fetal human renal tissues displayed no mouse CD31 positive vessels (FIG. 2e). Thus, 56-day gestational stage grafts, in contrast to later stage grafts, display host-specific vasculogenesis, including host-specific formation of the microcirculation.

Human renal grafts at a gestational stage of 56 days generate highly functionally differentiated, urine producing renal organs following transplantation into immunodeficient host mice: Human renal grafts implanted at a gestational stage of 56 days were found to form large fluid filled cysts (FIG. 3). Such cysts were observed to form in particular in abdominal grafts where they were not growth-limited by the renal subcapsular space. To assess whether the fluid in these cysts represented by-products of renal function, the cyst fluid was collected and analyzed for urea nitrogen and creatinine content, 6-8 weeks posttransplantation. As the transplants cannot use the host's excretory system for urine drainage, fluid was drained by insertion of a permanent microcatheter into the developing renal grafts. Average levels of urea nitrogen and creatinine were found to be higher in cyst fluid compared with those found in the sera of transplanted mice (518±169 mg/dl versus 45±8 mg/dl, P<0.001), indicating that the human renal grafts had produced urine. Levels of urea nitrogen and creatinine in the cyst fluid were significantly lower compared with native bladder urine (518±169 mg/dl versus 4,279±402 mg/dl, P<0.001). The generation of dilute urine in the cyst fluid is compatible with the reduced capacity of early gestational stage kidneys to concentrate urine. These results are in accordance with the demonstration that murine kidney precursors can develop into functional nephrons (Rogers, S. A. et al., 1998. Kidney Int. 54, 27-37; Rogers, S. A. et al., 2001. Am. J. Physiol. Regul. Integr. Comp. Physiol. 280, R132-136; Rogers, S. A. and Hammerman, M. R., 2001. Am. J. Physiol. Regul. Integr. Comp. Physiol. 280, R1865-1869; Rogers, S. A. and Hammerman, M. R., 2001. Am. J. Physiol. Regul. Integr. Comp. Physiol. 281, R661-665).

Human 49- to 56-day gestational stage renal grafts are well tolerated following transplantation into immunodeficient host mice bearing allogeneic human leukocytes: The relationship between the gestational stage of human renal grafts and their tolerance by allogeneic human lymphocytes was addressed. Preliminary experiments to establish baseline experimental conditions demonstrated that the minimal number of infused human donor PBMCs capable of inducing complete rejection of adult human renal allogeneic grafts transplanted into lymphoid cell-deficient recipient mice was 100 million cells (data not shown). Four weeks following transplantation of adult human kidney fragments into SCID/NOD bone marrow-reconstituted mouse recipients together with 100 million alloreactive human PBMCs, massive lymphocytic infiltration, tissue destruction and rejection were observed, as previously described (Dekel, B. et al., 1997. Transplantation 64, 1541-1550; Dekel, B. et al., 1999. Int. Immunol. 11, 1673-1683). At 4 weeks posttransplantation, 98-day gestational stage renal grafts displayed an average of 39.8±7.8 donor human T-lymphocytes per high power microscopic field. Despite the presence of allogeneic donor T-lymphocytes in these grafts, early rejection similar to that of adult transplants did not occur, and growth of 98-, 70-, 56-, and 49-day gestational stage allografts took place during the first month (Dekel, B. et al., 1997. Transplantation 64, 1550-1558; Dekel, B. et al., 2000. Transplantation 69, 1470-1478), as shown in FIGS. 4a-d, respectively. Nevertheless, analysis of allogeneic T-lymphocyte infiltration in 98-day gestational stage grafts at later time points (6-8 weeks post-transplant) revealed the harmful effects of the infiltrating cells as graft deterioration, in the form of tubule and glomerulus destruction, became apparent (FIGS. 4e-f, respectively), and transplant growth was significantly halted compared with transplants from animals that were not subjected to infusion of human PBMCs (FIG. 4a). Similar results were obtained for 70-day gestational stage human renal grafts (FIG. 4b). In sharp contrast, following infusion of 100 million graft-allogeneic human PBMCs into the host's peritoneum, 56- or 49-day gestational stage renal grafts exhibited preserved glomeruli and tubuli without infiltration of allogeneic human T-lymphocytes, (FIGS. 4g-h, respectively), and grew similarly to transplants of control mice not infused with PBMCs (FIGS. 4c-d, respectively), and hence displayed no apparent signs of destruction or rejection. Moreover, when the experimental protocol was altered so that two inocula of 100 million graft-allogeneic human PBMCs from different donors were infused 6 weeks apart, 56-day gestational stage grafts were not rejected, whereas 98-day gestational stage grafts transplanted in conjunction with PBMCs of the second allogeneic human donor were rejected (FIGS. 5a-b, respectively). Thus, the differentiated tissue, which developed for 6 weeks following implantation of 56-day gestational stage renal tissues remained tolerated by allogeneic human leukocytes, in strong contrast to 98-day gestational stage grafts.

RT-PCR analysis indicates human 56-day gestational stage renal tissues lack co-stimulatory molecule expression relative to later stage tissues: Among the multiple co-stimulatory pathways which have been identified, increasing evidence suggests that interaction of the T-lymphocyte costimulatory receptors CD28 and CD40 ligand (CD40L, CD154) with their respective ligands B7-1/-2 and CD40 expressed on antigen presenting cells (APCs) are critical for T-lymphocyte responses to alloantigens (Sayegh M H. and Turka L A., 1998. N Engl J. Med. 338, 1813; Boussiotis, V. A. et al., 1996. J. Exp. Med. 184, 365-376; Schwartz, R. H., 1996. J. Exp. Med. 184, 1-8; Sayegh, M. H. and Turka, L. A., 1998. N. Engl. J. Med. 338, 1813-1821; Li, Y. et al., 1999. Nature Med. 5, 1298-1302). Thus, in order to dissect the role of costimulatory molecule expression on renal graft tolerance by allogeneic human leukocytes, the expression of mRNA transcripts of the costimulatory molecules B7-1, B7-2, CD40, CD40L, and HLA-DR in human renal grafts at 56, 98 or 154 days of gestation was analyzed via RT-PCR prior to, immediately and at 2, 4 and 6 weeks posttransplantation into immunodeficient mouse hosts bearing allogeneic human leukocytes. The results surprisingly demonstrated that from the pretransplant stage to 6 weeks posttransplantation transcripts of the costimulatory molecules B7-1, and CD40 were expressed at extremely low or undetectable levels in 56-day gestational stage grafts at all time points analyzed (FIG. 6a), whereas in very sharp and significant contrast the later stage grafts (FIGS. 6a-c, respectively) displayed high and steadily increasing levels of these transcripts starting at 2 weeks posttransplantation. This pattern of co-stimulatory molecule gene expression is consistent with the in-vivo data demonstrating the optimal tolerance of allogeneic human leukocytes to human 49- to 56-day gestational stage renal grafts, and thereby provides a mechanism underlying such tolerance.

Microarray analysis indicates decreased expression of immunity-related genes in developing as opposed to mature human kidney tissue: To investigate inherent immunogenic properties of renal tissue during development which might account for decreased immunogenicity in developing relative to mature kidney, gene expression in fetal and adult human renal tissues was analyzed by microarray analysis. Namely, 231 genes having immunity related roles were analyzed (the complete list of genes can be found on the World Wide Web/Internet at http://www.weizmann.ac.il/immunology/reisner/immunogenicity.xls). These included genes encoding HLA molecules, cytokines, chemokines, chemokine receptors, apoptosis mediators, adhesion molecules, metalloproteinases, molecules of innate immunity and other immunomodulators. Hierarchical clustering (Eisen, M. B. et al., 1998. Proc. Natl. Acad. Sci. USA. 95, 14863-14868) of all genes on the basis of similarity in gene expression among the experimental groups revealed two main clusters, separating the adult from fetal tissues. Moreover, the immunity related genes were grouped according to gestational stage with a cluster of genes within gestational stage renal tissue and a cluster of genes within the adult kidney tissue on opposing sides of a hierarchical clustering dendrogram (FIG. 7a). The patterns of "immune" gene expression are presented in FIG. 7b. Such analysis unexpectedly uncovered that 68 genes were significantly changed between adult and fetal tissues (P<0.05, total number of misclassifications (TNoM)=0). Expression profiles of these genes demonstrated those increased in the adult tissues (n=57 genes; FIG. 7c, upper) and those decreased (n=11 genes; FIG. 7c, lower). Examples of the most significantly changed immunity related genes include those encoding molecules participating in both the acquired and the innate immune response (Table 3).

Thus, 13 of the 57 genes which were unexpectedly found to be significantly upregulated in adult versus developing renal tissues belong to the HLA class I and class II families. In addition, molecules that mediate trafficking of leukocytes, such as the chemokines RANTES and MCP-1 (Nelson, P. J. and Krensky, A. M., 2001. Immunity 14, 377-386), the adhesion molecule E-selectin (Tedder, T. F. et al., 1995. FASEB J. 9, 866-873), pro-inflammatory cytokines such as osteopontin (O'Regan, A. W. et al., 2000. Immunol. Today 21, 475-478; Ashkar, S. et al., 2000. Science 287, 860-863; Xie, Y. et al., 2001. Kidney Int. 60, 1645-1657) and complement genes known to be associated with innate immunity (Pratt, J. R. et al., 2002. Nature Med. 8, 582-587), were also unexpectedly found to be associated with the reduced immunogenicity of early gestational stage renal tissues relative to more mature tissues.

TABLE 3

Immunity related genes differentially expressed in fetal versus adult human renal tissue.

| Gene category | Differentially expressed gene |
|---|---|
| HLA | MHC class I, C |
|  | MHC class I, A |
|  | MHC class I, E |
|  | MHC class II, DPβ1 |
| Chemokines/ | RANTES |
| adhesion | monocyte chemotactic protein-1 (MCP-1) |
|  | monocyte chemotactic protein-2 (MCP-2) |
|  | E-selectin |
| Cytokines | osteopontin |
|  | interleukin-15 (IL-15) |
|  | prointerleukin-1β |
|  | interleukin-1 (IL-1) receptor |
| Innate immunity | complement component C1r |
|  | complement component 2 |
|  | complement control protein factor |
|  | mannose receptor-1 |
| Apoptosis | TNF receptor-1 associated protein (TRADD) |
|  | TNF-related apoptosis inducing ligand (TRAIL) |
|  | caspase-like apoptosis regulatory protein-2 |
|  | apoptotic cysteine Mch4 |

Discussion: In the presently disclosed experimental model, human renal grafts at different developmental stages were implanted in immunodeficient mouse hosts bearing allogeneic human leukocytes. The significant level of human alloreactive immunity generated in this model has been well documented (Segall, H. et al., 1996. Blood 88, 721-730; Reisner, Y. and Dagan, S., 1998. Trends Biotechnol. 16, 242-246). In the presently described results using this model, it was uncovered that both primary and secondary infusions of human PBMCs, obtained from separate graft-allogeneic donors and hence representing two independent T-lymphocyte repertoires, failed to reject human 49- to 56-day gestational stage renal grafts. The present results provide a mechanistic basis for the presently observed optimal tolerance to human renal grafts at a gestational stage of 49-56 days. Namely, global gene analysis suggests that developing human renal tissues display downregulation of multiple immune pathways relative to mature tissues. Furthermore, the presently uncovered absence of CD40 and B7-1 expression specifically observed in 49- and 56-day gestational stage human renal tissues for an extended period following transplantation implies that in such tissues there is a possible absence of, or immaturity of, donor hematopoietic antigen-presenting cells (APCs). In addition, the reduced alloreactive immunogenicity of such tissues could also be associated with the observed depletion of donor endothelial cells, shown recently to perform as APCs and/or as targets for T-lymphocyte mediated cytotoxicity in direct allorecognition (Kreisel, D. et al., 2002. Nature Med. 8, 233-239). Allogeneic tissue-engineered human skin, devoid of donor endothelial cells, and thereby limited in its antigen-presenting capabilities, has been shown to perform similarly to the early gestational stage renal tissues in a humanized model of skin rejection (Briscoe, D. M. et al., 1999. Transplantation 67, 1590-1599).

Thus, the presently described results unexpectedly showed that human 49- to 56-day gestational stage renal grafts transplanted into immunodeficient mouse hosts bearing allogeneic human leukocytes, in sharp contrast to earlier-/later-stage grafts, have the capacity to display, in the absence of teratoma formation, very significant growth, complete nephrogenesis, and formation of functional urine-producing renal organs which are well tolerated by the host's alloreactive immune system. At a gestational stage of 49-56 days, human renal tissues contain renal mesenchymal stem cells and ureteric bud branches, but no glomeruli, emphasizing their remarkable potential to differentiate following transplantation in the presence of an alloreactive human immune system. A key observation of the presently described results is that the apparent lack of immune rejection of 49- to 56-day gestational stage human renal grafts by allogeneic human leukocytes correlates with a host-specific origin of their vasculature, whereas, conversely, immune rejection of later stage grafts correlates with a graft-specific origin of their vasculature.

Conclusion: The presently disclosed results unexpectedly and convincingly demonstrated for the first time that there exists a narrowly defined gestational stage of human renal grafts, in particular a gestational stage of 49-56 days at which, unlike earlier-/later-stage grafts, such grafts can be transplanted into a host bearing allogeneic human leukocytes so as to generate, in the absence of teratoma formation, host-vascularized, well developed and tolerated, functional urine-producing renal organs. As such, the presently disclosed renal transplantation method overcomes critical limitations of the prior art by identifying for the first time human 49- to 56-day gestational stage renal grafts as being a source of allogeneic human renal grafts which is optimally suitable for therapeutic renal transplantation.

Example 3

Unlike Earlier-/Later-Stage Grafts, Porcine 27- to 28-Day Gestational Stage Renal Grafts have the Capacity to Generate, in the Absence of Teratoma Formation, Well Developed and Tolerated Functional, Urine Producing Renal Organs/Tissues Following Transplantation into Minimally Immunosuppressed Xenogeneic Mammalian Hosts Introduction: Allogeneic kidney transplantation is the optimal therapeutic option for renal failure, a highly debilitating and potentially fatal medical condition of significant morbidity. Such transplantation, however, is often impossible to implement due to the difficulty of finding a haplotype-matched kidney donor. Moreover, even when a matched kidney donor is found, allogeneic transplantation is associated with significant drawbacks, such as the requirement for permanent administration of toxic, immunosuppressive drugs such as cyclosporin A to prevent graft rejection, and the eventual inevitability of graft rejection in the long-term. Thus, there exists an urgent need for novel sources of renal grafts suitable for therapeutic transplantation in humans. A potentially optimal strategy for renal allograft transplantation would be to employ porcine renal grafts. Porcine hepatic grafts are considered an optimal animal alternative to human hepatic grafts due to their anatomical compatibility, their essentially limitless availability, and their use circumventing the medical/ethical drawbacks inherent to harvesting of organs from live/cadaveric human donors. However, porcine grafts cannot be used for transplantation in humans due to the current lack of any transplantation methods capable of overcoming the rapid and unavoidable rejection of transplanted xenografts. One proposed strategy for overcoming this obstacle suggests the use of gestational stage porcine grafts, since it has been demonstrated that the earlier the developmental stage of a graft, the less vigorously such a graft tends to be rejected following transplantation into a non-syngeneic host. However, to date, the hypothetical existence of specific gestational stages during which porcine grafts are sufficiently differentiated so as to be capable of generating functional renal organs without, or with minimal, risk of teratoma formation, while at the same time being sufficiently undifferentiated so as to be better tolerated than fully differentiated grafts following transplantation into a xenogeneic host has yet to be confirmed. While reducing the present invention to practice, such critical limitations of the prior art were overcome, as described below.

Materials and Methods:

Preparation of mouse graft hosts: refer to Example 1, "General Materials and Methods—Transplantation of developing renal grafts", above.

Harvesting of porcine renal grafts: Gestational-stage pigs were obtained from the Lahav Institute for Animal Research, Kibbutz Lahav, and grafts were harvested therefrom as previously described (Rogers S, et al., 1998. Kidney Int. 54, 27). All specimens for gene expression analysis were snap-frozen in liquid nitrogen. Tissues for transplantation were kept in sterile conditions at 4° C. (for approximately 2 hours) in either RPMI 1640 or Dulbecco's modified Eagle's medium (DMEM) supplemented with 10 percent fetal calf serum (FCS; Biological Industries, Beit HaEmek, Israel).

Transplantation of developing renal tissue: Refer to Example 1, "General Materials and Methods—Transplantation of developing renal grafts", above. Whole developing porcine kidneys at gestational stages of up to 28 days, or whole or 1-2 mm-diameter fragments of renal tissues at later stages of gestation were used in transplantations.

Analysis of graft infiltration, growth and differentiation: refer to Example 1, "General Materials and Methods—Transplantation of developing renal grafts", above.

Analysis of host-specific graft vasculogenesis: refer to Example 1, "General Materials and Methods—Transplantation of developing renal grafts", above.

Urine collection and analysis: refer to Example 1, "General Materials and Methods—Transplantation of developing renal grafts", above.

Transplantation of gestational stage porcine renal tissue grafts in normal immunocompetent mice in conjunction with mild, short-course costimulation blockade: Immunocompetent Balb/c mice received porcine 27- or 28-day gestational stage renal xenografts, and were subjected to costimulation blockade by intraperitoneal injection of 250 micrograms CTLA4-Ig (kindly provided by Steffen Jung, Hadassa Medical School, Jerusalem, Israel) every 48 hours for 2 weeks, starting 2 weeks posttransplantation. CTLA4-Ig is a fusion protein comprising the extracellular portion of mouse CTLA-4 fused to the constant region of human IgG which blocks the costimulatory interaction of the T-lymphocyte costimulatory receptor CD28 with its antigen presenting cell costimulatory ligands B7-1 and B7-2. Control mice were injected with PBS solution or control immunoglobulin.

Generation of minimally immunosuppressed normal mice as graft hosts: Minimally immunosuppressed C57BL/6 mice as graft hosts were generated by treatment with CTLA4-Ig, anti-CD40 and rapamycin, as follows. Anti-CD40L antibody and CTLA4-Ig were administered intraperitoneally at a dosage of 250 or 200 micrograms per mouse, respectively, on days 0, 2, 4, 6 posttransplantation. Rapamycin was administered subcutaneously at a dosage of 30 micrograms per mouse, every day beginning on day 0.

Statistical analysis: Refer to Example 1, "General Materials and Methods—Transplantation of developing renal grafts", above.

Experimental Results:

Porcine renal grafts at a gestational stage of 27-28 days, unlike earlier-/later-stage grafts, have the capacity to generate, in the absence of teratoma formation, well developed functional renal organs following transplantation into immunodeficient mouse hosts: To assess the influence of developmental stage of porcine renal xenografts on posttransplantation growth, renal differentiation, porcine renal grafts at developmental stages ranging from 20 days to 56 days of gestation were transplanted into immunodeficient mouse recipients, and the grafts were analyzed 8 weeks posttransplantation. As can be seen in Table 4, whole organ 27-28-day gestational stage grafts unexpectedly exhibited, uniquely relative to grafts at earlier or later gestational stages, significant growth with an average transplant size ratio at 8 weeks posttransplantation of 28.3±4.1, and full differentiation into mature glomeruli and tubuli (7.0±1.0 glomeruli and 35.5±5.1 tubuli per high power microscopic field).

The gross morphology and histological appearance of 28-day gestational stage grafts are shown in FIGS. 8a-b, respectively. In very sharp contrast, 42- and 56-day gestational stage grafts exhibited graft rejection and poor growth, as evidenced by central fibrosis and necrosis and graft deterioration, and a transplant size ratio of 8.2±1.2, respectively. In very sharp contrast, six of nine of the less developed 20- to 21-day gestational stage grafts failed to develop or generated few glomeruli and tubuli, but rather other teratoma-like differentiated derivatives, such as blood vessels (FIG. 8c), cartilage (FIG. 8d) and bone (FIGS. 8d-e). Also in very sharp contrast, more developed 24- to 25-day gestational stage porcine renal grafts were inferior to 27-28-day gestational stage grafts for nephrogenesis, as non-renal cell types and disorganized cell clusters were found in three of nine transplants (FIGS. 8f-h). These findings complement recent in-vitro data (Oliver, J. A. et al., 2002. Am. J. Physiol. Renal Physiol. 283, F799-809), which both indicate that early in gestation the developing kidney contains pluripotent progenitor cells, or embryonic renal stem cells, with the ability to generate many cell types.

TABLE 4

Development of porcine renal grafts at various gestational stages following transplantation into immunodeficient mouse hosts.

| Gestational stage of graft (days) | No. of transplants | Graft size | Incidence of graft growth* | Incidence of graft renal differentiation** | Incidence of teratoma formation | Incidence of necrosis |
|---|---|---|---|---|---|---|
| 56 | 7 | whole | 5/7 | none | none | 5/5 |
|  | 6 | fragments | 6/6 | 6/6 | none | none |
| 42 | 5 | whole | 4/5 | none | none | 4/4 |
|  | 6 | fragments | 6/6 | 6/6 | none | none |
| 27 to 28 | 12 | whole | 12/12 | 12/12 | none | none |
| 24 to 25 | 9 | whole | 8/9 | 5/8 | 3/8 | none |
| 20 to 21 | 9 | whole | 6/9 | 3/6 | 3/6 | none |

*Transplant growth and differentiation were assessed at 8 weeks posttransplantation.
** Differentiation was categorized as renal (only nephrons), non-renal (differentiated derivatives other than renal) and necrosis (in addition to nephrons, appearance of necrotic areas mostly in center of transplant).

Porcine 27- to 28-day gestational stage renal grafts display optimally host-derived vascularization: The ability of transplants to grow as tissues in non-syngeneic hosts depends primarily on their ability to sustain angiogenesis in such hosts (Gritsch, H. A. et al., 1994. Transplantation 57, 906-917). In the case of xenotransplantation, the particularly vigorous graft rejection which usually occurs is largely proportional to the extent of the donor-specific origin of the graft vasculature (Cascalho, M. and Platt, J. L., 2001. Immunity 14, 437-446). To determine the ability of recipient mice to support angiogenesis of avascular 28-day gestational stage renal grafts by ingrowth of host-derived blood vessels, expression of mouse PECAM (CD31), a marker of sprouting endothelial cells, was analyzed immunohistochemically in the developing transplants. Counts of immunoreactive vessels reflecting the combined total number of capillary and larger vessels of host origin were performed per high power microscopic field, as previously described (Vermeulen, P. B. et al., 1996. Eur. J. Cancer 32A, 2474-2484). At 4 weeks posttransplantation, 21.3±3.2 vessels of host origin per high power microscopic field supplying the developing grafts were found. Among these grafts, all larger vessels stained positive for mouse CD31 (FIG. 9a). In addition, medium and small size capillaries of host origin were detected in both glomeruli (FIG. 9b) and parenchyme (FIG. 9c) of the grafts. In transplants originating from mature, vascularized 56-day gestational stage porcine renal grafts, there was a significantly reduced mouse CD31 positive vessel count (11.5±2.2, respectively, P<0.001) composed of mainly external larger vessels, but not endothelial cells in glomeruli and small capillaries (FIG. 9d). Control sections of vascularized porcine renal tissues displayed no CD31-positive host-derived vessels (FIG. 9e). Thus, 28-day gestational stage grafts, in contrast to later stage grafts, display host-specific vasculogenesis, including host-specific formation of the microcirculation.

Porcine renal grafts at a gestational stage of 28-days have the capacity to generate urine producing renal organs following transplantation into immunodeficient mouse hosts: As can be seen in FIG. 10, examination porcine 28-day gestational stage renal grafts 8 weeks posttransplantation showed that such grafts unexpectedly have the capacity to generate urine-producing renal organs following transplantation into immunodeficient mouse hosts. Such cysts were observed to form in particular in abdominal grafts where they were not growth limited by the renal subcapsular space. To assess whether the fluid in these cysts represented by-products of renal function, a permanent microcatheter was connected to the cysts, and fluid from the grafts (n=4) was collected and analyzed for urea nitrogen and creatinine content, 6-8 weeks posttransplantation. Average levels of urea nitrogen and creatinine were found to be higher in cyst fluid compared with those found in the sera of the host animals ($7.2 \pm 1.9$ mg/dl versus $0.46 \pm 0.048$ mg/dl, respectively; $P<0.001$), indicating that the porcine renal grafts had produced urine. Levels of urea nitrogen and creatinine in the cyst fluid were significantly lower compared with native bladder urine ($7.2 \pm 1.9$ mg/dl versus $54 \pm 6$ mg/dl, respectively; $P<0.001$). The generation of dilute urine in the cyst fluid is compatible with the reduced capacity of early gestational stage kidneys to concentrate urine. These results are in accordance with reports that transplanted murine kidney precursors can develop into functional nephrons (Rogers, S. A. et al., 1998. Kidney Int. 54, 27-37; Rogers, S. A. et al., 2001. Am. J. Physiol. Regul. Integr. Comp. Physiol. 280, R132-136; Rogers, S. A. and Hammerman, M. R., 2001. Am. J. Physiol. Regul. Integr. Comp. Physiol. 280, 81865-1869; Rogers, S. A. and Hammerman, M. R., 2001. Am. J. Physiol. Regul. Integr. Comp. Physiol. 281, R661-665).

Figure 12A:
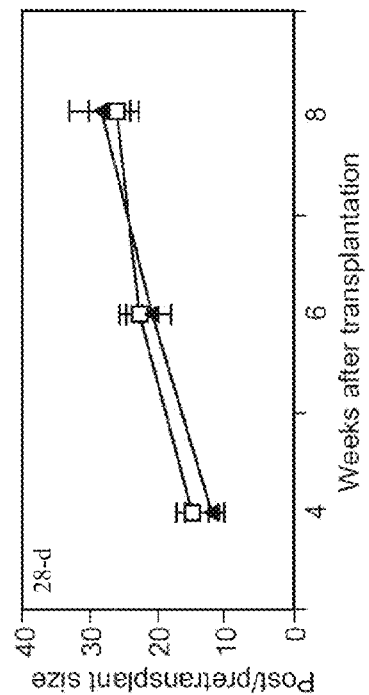
Figure 12B:
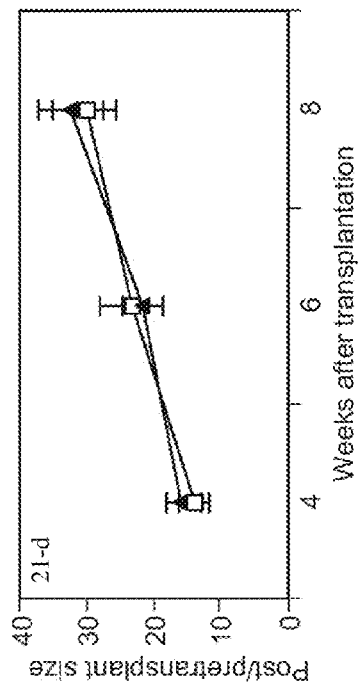
Figure 12C:
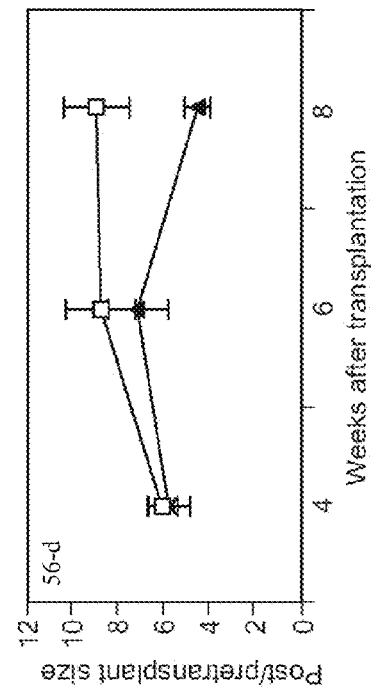
Figure 12D:
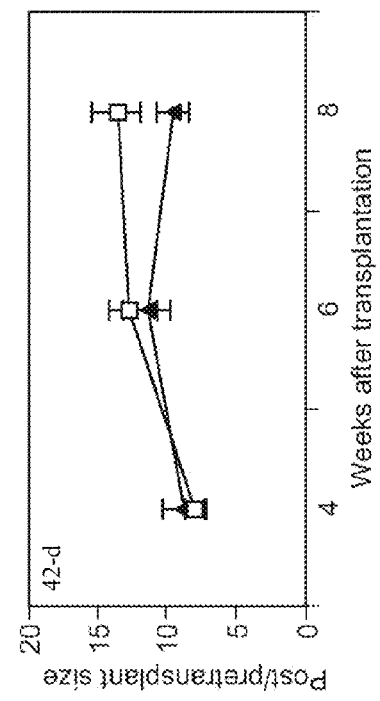

Porcine 27- to 28-day gestational stage renal grafts, unlike later-stage grafts, are well tolerated following transplantation into immunodeficient mouse hosts bearing human leukocytes: The relationship between the gestational stage of porcine renal grafts and their tolerance by human leukocytes posttransplantation was addressed. Preliminary experiments to establish baseline experimental conditions demonstrated that the minimal number of infused PBMCs capable of inducing complete rejection of adult porcine renal grafts transplanted into lymphoid compartment-deficient mice was 100 million (data not shown). In these experiments of six adult-stage porcine renal grafts were infiltrated and histologic damage and destruction were apparent within 3 weeks posttransplantation (data not shown). Analysis of such grafts 4 weeks posttransplantation via anti-CD3 immunohistochemistry showed significant human T-lymphocyte infiltration (FIGS. 11a-b), and analysis via H&E staining showed concomitant destruction of renal parenchyme tissue (FIG. 11c). Transplants of 21- and 28-day gestational stage porcine renal grafts were well tolerated, when examined 6 or 8 weeks following transplantation into immunodeficient mouse hosts bearing human leukocytes, as evidenced by their high and steadily increasing posttransplant to pretransplant size ratios (FIGS. 12a and 12b, respectively). In sharp contrast, however, 42- and 56-day gestational stage grafts displayed significant signs of rejection, as evidenced by significantly lower posttransplant to pretransplant size ratios (FIGS. 12c and 12d, respectively). Analysis at later time points indicated that five out of six 56-day gestational stage grafts displayed significant signs of rejection in the form of tissue damage concomitant with T-lymphocyte infiltration, as demonstrated by immunohistochemical assay with anti-human CD3 antibody (FIGS. 13a-b), and by H&E histochemical staining (FIG. 13c) of graft sections. These results, and similar findings from experiments with porcine 42-day gestational stage renal grafts showed that grafts at such developmental stages were vigorously rejected following transplantation into immunodeficient mouse hosts bearing human leukocytes. In sharp contrast, as shown in FIGS. 14a-b, porcine renal grafts at a gestational stage of 28 days displayed intact glomeruli and tubuli and did not display T-lymphocyte infiltration following transplantation into immunodeficient mouse hosts bearing graft-xenogeneic human leukocytes. Furthermore, such 28-day gestational stage grafts displayed growth and were well tolerated following transplantation into immunodeficient mouse hosts in conjunction with 100 million human PBMCs from a first donor, and following infusion of the hosts 4 weeks posttransplantation with second dose of 100 million PBMCs from a different human donor (FIG. 15a). In sharp contrast, however, 56-day gestational stage grafts displayed reversed growth and were rejected following transplantation into immunodeficient mouse hosts in conjunction with 100 million human PBMCs from a first donor, and following infusion of the hosts 6 weeks posttransplantation with second dose of 100 million PBMCs from a different human donor (FIG. 15b).

The optimally low immunogenicity of porcine 27- to 28-day gestational stage renal xenografts was further demonstrated by transplanting either adult-stage or 27- to 28-day gestational stage porcine renal grafts into normal, immunocompetent Balb/c mice receiving adjunct short-course costimulatory blockade treatment with CTLA4-Ig (250 micrograms every 48 hours, for the period 2-4 weeks following transplantation). CTLA4-Ig an immunoglobulin fusion protein that inhibits CD28-mediated costimulation of T-lymphocyte of activation by B7 expressed on antigen-presenting cells (Linsley, P. S. et al., 1991. J. Exp. Med. 174, 561-569). Six of ten porcine 27- to 28-day gestational stage renal grafts transplanted with adjunct short-course CTLA4-Ig treatment displayed significant growth and renal differentiation, whereas all adult grafts (8/8) transplanted under similar conditions exhibited abnormal graft morphology, necrosis and a high degree of lymphocyte infiltration. In control experiments, evaluation of adult (n=10) and 27- to 28-day gestational stage renal (n=10) grafts 2 weeks posttransplantation showed that such grafts were rejected. These results therefore support the experimental results disclosed above indicating that porcine 27- to 28-day gestational stage renal grafts are at an optimal stage of development for xenotransplantation compared to grafts at later stages of development.

Porcine 28-day gestational stage renal grafts transplanted into minimally immunosuppressed normal mice generate well developed and tolerated renal organs: Porcine 28-day gestational stage renal grafts were transplanted into C57BL/6 mice receiving no treatment, or receiving treatment with rapamycin, CTLA4-Ig and anti-CD40L, and graft sections were analyzed via H&E histochemistry at 2 weeks posttransplantation. Control transplantation of such grafts into immunodeficient NOD-SCID mice showed generation of well-developed renal structures (FIG. 15c). While transplantation of such grafts into untreated immunocompetent C57BL/6 mice showed heavy lymphocytic infiltration into the host's kidney and fibrosis, without significant residual kidney tissue (FIG. 15d), transplantation of grafts into immunocompetent C57BL/6 mice treated with rapamycin, CTLA4-Ig and anti-CD40L antibody generated normal kidney tissue, containing glomeruli and tubuli (FIG. 15e). The grafts in the latter experimental group appeared more organized, less fibrotic and more mature than those transplanted into the untreated immunocompetent mice.

Discussion: The immunogenicity of developing porcine renal xenografts was evaluated using two different immunological models. In the first model, the grafts were transplanted into immunodeficient mouse hosts bearing human leukocytes. The significant level of human specific immunity generated in this model following infusion of human PBMCs has been well documented (Segall, H. et al., 1996. Blood 88, 721-730; Reisner, Y. and Dagan, S., 1998. Trends Biotechnol. 16, 242-246). In the presently disclosed results using this model, both primary and secondary infusions of human PBMCs, obtained from separate donors and hence representing two independent T-lymphocyte repertoires, were not capable of rejecting porcine 27- to 28-day gestational stage grafts. In the second immunological model employed, the grafts were transplanted into hosts bearing normal immunocompetent mouse leukocytes. Rejection in such hosts can be triggered by donor antigen presenting cells transferred in the implant, or, alternatively, by cross-priming against host antigen presenting cells loaded with donor antigens in a fashion similar to the normal process for the presentation of bacterial or viral antigens (Sayegh, M. H. and Turka, L. A., 1998. N. Engl. J. Med. 338, 1813-1821; Benichou, G., 1999. J. Immunol. 162, 352-358). Because the 27- to 28-day gestational stage renal tissues possibly lack mature antigen presenting cells, in addition to a relative reduction in homing receptors and specific cytokines or chemokines, the hypothesis that blockade of cross priming may be sufficient to alleviate the observed rejection of these implants was tested. The presently disclosed results indicated that immune rejection of porcine 27- to 28-day gestational stage renal grafts by the immunocompetent mouse leukocytes could be obviated by short course co-stimulatory blockade with CTLA4-Ig, a protocol that failed to prevent rejection of adult stage grafts. These results can therefore easily be adapted for facilitating transplantation of porcine 27- to 28-day gestational stage renal organs in human recipients.

Thus, the presently described results unexpectedly showed that porcine 27- to 28-day gestational stage renal grafts, unlike earlier-/later-stage grafts, transplanted into immunodeficient mouse hosts bearing human leukocytes have the capacity to generate, in the absence of teratoma formation, renal organs which display very significant growth, complete nephrogenesis, and formation of urine-production capacity, and which are well tolerated by human leukocytes. This is in sharp contrast to earlier gestational stage grafts which fail to mature exclusively into differentiated renal structures and form teratoma-like non-renal differentiated derivatives and disorganized cell clusters. At a gestational stage of 27-28 days, porcine renal tissues contain renal mesenchymal stem cells and ureteric bud branches, but no glomeruli, emphasizing their remarkable potential to differentiate following transplantation. A key observation of the presently described results is that tolerance to 27- to porcine 28-day gestational stage renal grafts by human leukocytes in immunodeficient mouse hosts correlates with the host-specific origin of their vasculature, whereas immune rejection of later stage grafts correlates with the graft-specific origin of their vasculature. The suitability of porcine 28-day gestational stage renal grafts for transplantation was further demonstrated by the optimal growth and development of graft-derived renal tissues in normal mouse hosts minimally immunosuppressed by treatment with CTLA4-Ig, anti-CD40L and rapamycin as described above.

Conclusion: The presently disclosed results unexpectedly and convincingly demonstrated for the first time that there exists a narrowly defined gestational stage of porcine renal grafts, in particular a gestational stage of 27-28 days, at which, unlike earlier-/later-stage grafts, such grafts can be transplanted into a minimally immunosuppressed normal xenogeneic mammalian host so as to generate, in the absence of teratoma formation, host-vascularized, structurally and functionally differentiated, urine-producing renal organs which are well developed and tolerated. As such, the presently disclosed renal transplantation method overcomes critical limitations of the prior art by identifying for the first time porcine 27- to 28-day gestational stage renal grafts as a novel source of renal grafts which, by virtue of their optimal differentiation capacity, low immunogenicity, non-human origin, and essentially unlimited availability, are optimally suitable for therapeutic renal transplantation in humans.

Example 4

Treatment of Human Renal Failure by Transplantation of 27- to 28-Day Gestational Stage Porcine Renal Grafts, or Allogeneic Human 49- to 56-Day Gestational Stage renal grafts Introduction: Renal allograft transplantation, the optimal treatment for renal failure in humans, is impossible to practice in a large number of cases due to unavailability of immunologically-matched allograft donors. As respectively shown in Examples 2 and 3 above, human 49- to 56-day gestational stage renal grafts, or porcine 27- to 28-day gestational stage renal grafts are capable of generating, in the absence of teratoma formation, highly developed, functional, urine-producing, renal organs which are well tolerated by the functional allogeneic or xenogeneic, respectively, leukocyte compartment of the host. Thus, transplantation of such grafts can be used for effectively treating renal failure in humans as described below.

Materials and Methods:

Harvesting of renal grafts: For harvesting of porcine grafts, sows (under appropriate rearing conditions, e.g. following Good Manufacturing Practice) are brought into oestrous either by natural means (housing near males) or more likely by hormone injections known to those skilled in the art. Once the sows reach oestrous they are inseminated with semen from tested boars of a suitable quality. Following insemination, sows are monitored and tested for pregnancy as appropriate. At 27-28 days of gestation (full gestation 112-115 days), sows are anaesthetised and a hysterectomy performed. The uterus is passed to a clean room and opened under sterile conditions (e.g. flow cabinet). Individual fetuses are removed, and are held in cold buffer before dissection of the metanephroi. Once they have been dissected, metanephroi are stored in vials. Each vial is labeled such that each metanephroi can be traced back to a specific pig. Appropriate samples may be taken for biological safety evaluation. After biological safety clearance, vials are shipped to a clinical center (for example, a hospital). Alternatively, isolation of metanephroi may take place the clinical center, and final safety evaluation is then obtained retrospectively.

Human 49- to 56-day gestational stage renal organs are harvested as described in Example 2 above.

Transplantation: Starting on the day of the transplantation, short course costimulation blockade treatment in the form of a CTLA4-Ig administration regimen essentially corresponding to that described in Example 3 above, is administered to a human patient suffering from renal failure.

While the patient is being prepped for surgery, the renal grafts are prepared for transplantation.

The patient's abdomen is opened, and, depending on the patient's body weight and renal functionality requirements, a suitable number of metanephroi are transplanted adjacent to a blood vessel at an intestinal loop. For example, between one and ten metanephroi are transplanted. Preferably at least two metanephroi are transplanted to take into account possible transplant failure.

After the operation, the patient remains in the clinic or hospital to recover (for example, for about 3 or 4 days). However, it is possible that transplantation may be performed using a laparoscope, and if so the recovery time would be much shorter.

Initially, the patient may continue to undergo a normal dialysis programme. The patient is monitored as required for signs of graft rejection, and appropriate immunosuppressive treatment for preventing graft rejection is administered if the need arises. The patient could return for imaging after a suitable time following discharge (for example, about 2-3 weeks following discharge). Using a CT imaging procedure, the degree of transplant development is assessed and this information used to schedule surgical connection of graft-derived urinary cysts with the urinary system of the patient.

Urinary Connection: As the graft-derived renal organ matures, it begins to produce urine. If urine is not allowed to flow (i.e. an obstruction occurs), the backpressure produced inhibits nephrogenesis, and inhibits kidney development. However, time is required for the ureter to reach a size that allows it to be anastomosed to the host urinary tract. Hence there is an optimum time, typically at about 6-8 weeks post-transplantation, which is assessed clinically, to perform surgical connection of graft-derived urinary cysts with the urinary system of the patient. Growth and differentiation of graft(s) into functional renal organ(s) is monitored via computerized tomography/ultrasound imaging until urine-filled cyst(s) are detected, at which time urinary anastomosis is performed between the cyst(s) and the subject's urinary system so as to allow drainage of graft-produced urine via the ureter route.

Excess transplants may be removed at this stage. The patient is likely to require a stay in the clinic or hospital to recover, for example of four days or so.

For a period of time prior to and following urinary connection, until equilibrium is reached, the patient may be asked to collect total daily urine samples.

The volume of the daily urine samples is monitored and samples tested. In addition, the patient may have daily blood samples taken to monitor electrolytes (in addition to whatever is needed to monitor immunosuppression). Based on clinical signs, dialysis may be continued as required, but slowly reduced (and eventually terminated) as renal function increases. Imaging is preferably performed regularly during the early follow-up period to monitor graft-derived renal organ development, and to monitor the functional status of the surgically implanted urinary drainage system.

Results:

As a result of the renal functionality conferred to the patient by the transplanted renal graft(s), the end-stage renal disease is cured, or substantially alleviated in the patient, without having required an HLA-matched human organ donor, and without the need for permanent, harmful, immunosuppression to prevent graft rejection, in sharp contrast to all prior art methods of therapeutic renal transplantation.

Example 5

General Materials and Methods—Transplantation of Developing Hepatic Grafts

Animal graft hosts: Animal graft hosts were maintained under conditions approved by the Institutional Animal Care and Use Committee at the Weizmann Institute. Immune deficient, or human PBMC-reconstituted, NOD/SCID mice at the age of 8-10 weeks (Weizmann Institute Animal Breeding Center, Rehovot, Israel) were used as hosts for the transplantation studies. NOD/SCID mice bearing a human leukocyte compartment were generated by intraperitoneal injection of $80 \times 10^6$ human PBMCs, and mice testing positive for engraftment were selected as hosts for transplantation experiments. All mice were kept in small cages (up to 5 animals in each cage) and fed sterile food and acid water containing ciprofloxacin (20 mg/ml).

Transplantation procedures: Transplantations were performed in NOD/SCID recipients under general anesthesia induced by intraperitoneal injection of 2.5 percent Avertin in PBS (10 ml/kg). For transplantation under the renal capsule, the host kidney was exposed through a left lateral incision. A 1.5-mm incision was made at the caudal end of the renal capsule, and 1-2 mm-diameter fragments of gestational stage liver grafts were implanted under the renal capsule. For intrasplenic transplantation, graft tissue was minced to 1 mm fragments in sterile PBS. The host spleen was exposed through a left lateral incision and a suspension of 1 mm-diameter fragments of gestational stage liver was injected into the lower pole of the spleen. Hemostasis was achieved by suture ligation below the injection site. For intrasplenic transplantation, the host spleen was exposed via a left lateral incision and a suspension of liver fragments 1 mm diameter in sterile PBS was injected into the lower pole of the spleen. Hemostasis was achieved by suture ligation below the injection site. +/−

Histological analysis: Tissues were fixed by overnight incubation in 4 percent paraformaldehyde in phosphate-buffered saline (PBS) solution, the fixed tissues were processed through graded alcohols, through xylenes, and were paraffin-embedded. Four micron-thick sections of embedded tissues were cut and mounted on positively charged (poly-L-lysine-coated) glass slides. The slide-mounted tissue sections were deparaffinized in xylene following rehydration in graded alcohols. Endogenous peroxidase was quenched in 0.6 percent hydrogen peroxide in 70 percent methanol for 20 minutes. Antigen retrieval by microwave boiling or protease pretreatment was applied when needed. For immunostaining, slides were incubated in a humidified chamber for 60 minutes with primary antibody, following application of DAKO Envision TM+ system, horseradish peroxidase (HRP). Diaminobenzidine (DAB) or aminoethylcarbasole (AEC) reagents were used as chromogens. The slides were hematoxylin counterstained and mounted. Anti-pig albumin antibody was obtained from Bethyl Laboratories; anti-Ki67 antibody was used as a marker of cell proliferation. Periodic acid-Schiff (PAS) dye was used as a marker of glycogen synthesis. Sections were stained with hematoxylin-eosin (H+E).

Example 6

Porcine 28-Day Gestational Stage Hepatic Grafts, Unlike Earlier-Stage Grafts, have the Capacity to Generate, without Risk of Teratoma Formation, Well Developed and Tolerated, Functional Hepatic Organs/Tissues Following Transplantation into Minimally Immunosuppressed Xenogeneic Mammalian Hosts Introduction: Hepatic allograft transplantation is the only therapeutic option for hepatic failure in humans, a highly debilitating and potentially fatal medical condition of significant morbidity. Such transplantation, however, is often impossible to implement due to the difficulty of finding a haplotype-matched liver donor. Moreover, even when a matched donor is found, allogeneic transplantation is associated with significant drawbacks, such as the requirement for permanent administration of toxic immunosuppressive drugs such as cyclosporin A to prevent graft rejection. Thus, there exists an urgent need for novel sources of liver grafts suitable for therapeutic transplantation in humans. A potentially optimal strategy for hepatic allograft transplantation would be the use of porcine hepatic grafts. Porcine hepatic grafts are considered an optimal animal alternative to human hepatic grafts due to their anatomical compatibility, their essentially unlimited availability, and their non-human origin circumventing the medical/ethical drawbacks inherent to harvesting of organs from live/cadaveric human donors. However, porcine grafts cannot be used for transplantation in humans due to the current lack of any transplantation methods capable of overcoming the rapid and unavoidable rejection of transplanted xenografts. One proposed strategy for overcoming this obstacle suggests the use of gestational stage porcine grafts, since it has been demonstrated that the earlier the developmental stage of a graft, the less vigorously such a graft tends to be rejected following transplantation into a non-syngeneic host. However, to date, the hypothetical existence of specific gestational stages during which porcine grafts are sufficiently differentiated so as to be capable of generating functional renal organs without, or with minimal, risk of teratoma formation, while at the same time being sufficiently undifferentiated so as to be well tolerated following transplantation into a xenogeneic host has yet to be confirmed. While reducing the present invention to practice, such critical limitations of the prior art were overcome, as described below.

Materials and Methods:

Animal graft hosts: Refer to Example 5, "General Materials and Methods—Transplantation of developing hepatic grafts", above.

Harvesting of porcine gestational stage hepatic organs/tissues: Porcine gestational stage hepatic grafts for transplantation were obtained with the assistance of the Lahav Institute for animal research, Kibbutz Lahav. Hepatic tissues were harvested from pregnant sows on days 21, 24, 28, 42, 56 and 80 of pregnancy operated on under general anesthesia. The study protocol was approved by the ethics committees of both The Lahav Institute and The Weizmann Institute of Science, Rehovot. Warm ischemia time of gestational stage pigs was less than 10 minutes prior to transfer and maintenance in cold PBS. Tissues for transplantation were extracted under the stereoscope and were maintained under sterile conditions at 4 degrees centigrade in RPMI 1640 (Biological Industries, Beit HaEmek, Israel) prior to transplantation. Cold ischemia time prior to transplantation was kept below 2 hours.

Transplantation Procedures Refer to Example 5, "General Materials and Methods—Transplantation of developing hepatic grafts", above.

Transplant growth measurement: Graft recipients were sacrificed at 6-8 weeks posttransplantation and organs bearing the transplanted grafts were harvested and either fixed in 10 percent paraformaldehyde or cryopreserved. The long (L) and short (W) axes of the grafts were measured and the transplant size was calculated by multiplying L×W.

Histological Analysis: Refer to Example 5, "General Materials and Methods—Transplantation of developing hepatic grafts", above.

Porcine albumin serum secretion analysis: Serial bleedings at 2, 4, 6, and 8 weeks posttransplantation were performed from the retro-orbital plexus. Serum was separated and kept frozen for porcine albumin ELISAs.

Generation of minimally immunosuppressed normal mice as graft hosts: Minimally immunosuppressed C57BL/6 mice as graft hosts were generated by treatment with CTLA4-Ig, anti-CD40 and rapamycin, as follows. Anti-CD40L antibody and CTLA4-Ig were administered intraperitoneally at a dosage of 250 or 200 micrograms per mouse, respectively, on days 0, 2, 4, 6 posttransplantation. Rapamycin was administered subcutaneously at a dosage of 30 micrograms per mouse, every day beginning on day 0.

Experimental Results:

Porcine hepatic grafts at a gestational stage of 28 days, unlike earlier-stage grafts, have the capacity to generate, in the absence of teratoma formation, well developed functional hepatic organs/tissues following transplantation into immunodeficient mice: The potential of porcine hepatic grafts at various developmental stages to form teratomas, as opposed to tissues fully committed along the hepatic lineage, following transplantation into xenogeneic hosts was analyzed. Porcine hepatic grafts at various gestational stages were transplanted under the renal capsule in SCID mouse recipients, and the grafts were harvested at 6 weeks posttransplantation and subjected to histochemical analysis of lineage-specific differentiation. As can be seen in Table 5, a considerable incidence of teratoma formation occurred following transplantation of 21- and 24-day gestational stage grafts, whereas, in very sharp and surprising contrast, fully differentiated hepatic tissues which were free of teratoma-like structures were formed following transplantation of 28-day gestational stage grafts.

TABLE 5

Analysis of capacity of porcine hepatic grafts at various gestational stages to generate of structurally and functionally differentiated hepatic organs/tissues in the absence of teratoma formation following transplantation into immunodeficient mice

| Gestational stage of graft (days) | Incidence of teratoma formation | Incidence of hepatic growth and differentiation |
|---|---|---|
| 21 | 10/27 | 5/27 |
| 24 | 3/8 | 5/8 |
| 28 | 0/23 | 21/23 |

Grafts were implanted under the renal capsule of recipients, and were examined for lineage-specific differentiation at 6 weeks posttransplantation.

Histochemical analysis of lineage-specific markers in tissues derived from 21- or 28-day gestational stage grafts implanted under the renal capsule was performed at 6 weeks posttransplantation. As can be seen in FIG. 16a, 21-day gestational stage grafts generated teratoma-like structures including substantial amounts cartilage, as determined via staining with Alcian-blue. FIG. 16b depicts cartilage formation derived from 24-day gestational stage grafts. In very sharp contrast, however, as can be seen in FIGS. 16c-e, 28-day gestational stage grafts generated fully differentiated, functional hepatic tissues in the absence of teratoma formation. FIGS. 16c and 16d respectively show significant levels of glycogen synthesis and storage as determined via PAS and anti-pig albumin antibody staining. FIG. 16e clearly shows, via H&E histochemical staining, the such grafts display liver specific tissue architecture, as evidenced by organization of hepatocytes along hepatic cords surrounding central veins (arrow head) while the portal elements of the liver are evidenced by bile duct formation (arrows). It can be observed that the interface between the kidney and the graft is not sharp, indicating that such grafts have the capacity to integrate within the host kidney Similar results were obtained following intrasplenic transplantation. Histochemical analysis via H&E staining of 21-day gestational stage grafts analyzed at 7 weeks posttransplantation clearly showed that such grafts generated teratomas, as evidenced by extensive cartilage differentiation (FIGS. 17a-b). In sharp contrast, as was the case with subcapsular transplantation, 28-day gestational stage grafts transplanted intrasplenically and analyzed at 6 weeks posttransplantation displayed significant structural and functional hepatic development, in the absence of teratoma formation. Tissue sections of such grafts analyzed by staining with H&E (FIGS. 18a-b), PAS (FIG. 18c-d), or anti-pig albumin antibody (FIG. 18e-f), all displayed marked differentiation of hepatic lobular structures. As shown in FIG. 18b nests of partially vacuolized hepatocytes organized in hepatic lobules were formed. Liver functionality was demonstrated by glycogen synthesis/storage (FIGS. 18c-d), and by albumin synthesis (FIG. 18e-f). Furthermore, staining of sections with antibody specific for the proliferation marker Ki67 demonstrated the clear proliferative capacity of the graft-derived hepatocytes (FIG. 18g-h).

To define the gestational stage at which porcine hepatic grafts have the capacity to generate optimally functional hepatic organs, grafts at various stages of development (21, 28, 42, 56 or 80 days of gestation) were transplanted either under the renal capsule or intrasplenically, and secretion of graft-derived (i.e. porcine) albumin in the serum of the hosts was analyzed 6 weeks posttransplantation via ELISA using a highly specific anti-pig albumin antibody for detection. Porcine albumin secretion could be selectively detected as early as 3 days following transplantation of liver embryonic precursors (data not shown). FIGS. 19a-b respectively summarize the results of 8 independent analyses of sera from hosts subjected to either subcapsular or intrasplenic transplantation of the grafts. As can be seen with both types of transplantation, grafts at a gestational stage of 28 days were very unexpectedly found to very clearly display optimal albumin secretion levels as compared to grafts at both earlier and later developmental stages. This trend was well in accordance with the above-described histological data. FIG. 19c shows significant levels of pig albumin secretion in serum of recipient mice at 2 and 4 weeks posttransplantation of 28-day gestational stage porcine hepatic grafts into the spleen or under the renal capsule of recipients.

Immunogenicity of porcine developing hepatic tissues increases as a function of their gestational stage at time of transplantation: Transplantation of porcine hepatic grafts at various gestational stages into NOD-SCID mice reconstituted with a human leukocyte compartment was employed to study the immunogenicity of such grafts. Transplants from grafts at gestational stages of 24, 28 or 42 days were analyzed via anti-human CD45 immunohistochemistry at 4 weeks posttransplantation The results, shown in FIGS. 20a-c, respectively, imply that cellular infiltration and fibrosis increases as the grafts' gestational stage increases. The growing implants generated by 24- or 28-day gestational stage grafts were found to be composed of well-organized hepatic tissue while those generated by 42-day gestational stage grafts showed clear signs of lymphocytic infiltration and hepatocyte destruction, and residual hepatic tissue. In the tissues generated by 24-day gestational stage grafts, there are almost no signs of human lymphocytic infiltration, with only a few scattered cells visible in the graft, while those generated by 28-day gestational stage grafts display significant diffuse human lymphocytic infiltration. The immunogenicity of embryonic pig liver may be due to the presence of hematopoiesis in embryonic liver.

Porcine hepatic grafts at gestational stages of 28-42 days transplanted into minimally immunosuppressed normal mice generate well tolerated and developed functional hepatic organs/tissues: Immunocompetent C57BL/6 recipient mice treated with rapamycin, CTLA4-Ig and anti-CD40L antibody for two weeks were transplanted with gestational stage porcine hepatic grafts and graft-generated tissues were analyzed for hepatic development following transplantation. Positive and negative control groups included immune deficient NOD-SCID and untreated immunocompetent C57BL/6 mice, respectively. Growth and function of 28-day gestational stage grafts transplanted into C57BL/6 mice untreated, or treated with rapamycin, CTLA4-Ig and anti-CD40L antibody was analyzed. Blood was withdrawn on days 4, 7 and prior to sacrificing the recipients, and the serum was analyzed for pig albumin levels. Histological findings and negligible serum pig albumin levels indicated heavy infiltration and fibrosis without residual hepatic tissue in the untreated immunocompetent mice (data not shown). In the treated animals nearly normal hepatic tissue with abundant hepatocytes and many blood vessels was observed. Moreover, specific stainings show that the hepatocytes contain glycogen and express albumin (FIGS. 21a-b). The effectiveness of this immune suppressive regimen was also confirmed by pig albumin ELISA of recipient serum. As can be seen in FIG. 22 stable albumin secretion was observed in 3 out of 4 animals in this treatment group, while albumin secretion decreased to 0 at day 7 in the negative control group.

The marked efficacy of the immunosuppressant triple cocktail treatment is best exemplified when analyzing, at time points later than 2 weeks posttransplantation into treated animals, tissues generated by the more immunogenic 42-day gestational stage grafts. As can be seen in FIGS. 21c-d, tissues derived from such grafts analyzed at 4 or 6 weeks posttransplantation, respectively, exhibited normal hepatic tissue with hepatocytes containing glycogen and expressing albumin. Blood sinuses were also observed. Moreover, the levels of pig albumin detected in the serum of the recipients' mice revealed significant albumin secretion during the first 4 weeks posttransplantation (FIG. 23). The decrease in pig albumin secretion 6 weeks after transplantation is similar to the pattern observed when transplanting 42-day gestational stage grafts into NOD-SCID mice.

Thus, these results indicate that to achieve successful engraftment of porcine 28-day gestational stage hepatic grafts into xenogeneic recipients it might be possible to successfully use immunosuppression with CTLA4-Ig and anti-CD40L antibody, without or with a reduced dose of rapamycin.

Conclusion: The presently disclosed data unexpectedly demonstrated that porcine 28-day gestational stage hepatic grafts have optimal capacity to generate, without risk of teratoma formation, highly developed, functional hepatic organs which are well tolerated following transplantation into immunocompetent mice minimally immunosuppressed by treatment with CTLA4-Ig, anti-CD40L and rapamycin as described above. As such, the presently disclosed findings enables optimal therapeutic liver transplantation in humans using gestational stage porcine hepatic grafts relative to prior art methods. By virtue of employing porcine grafts, the method enabled by the present findings is far superior to the use of human grafts, the prior art method of choice, which suffers from the ethical and medical drawbacks inherent to harvesting of organs from live/cadaveric human donors.

Example 7

Human 7-Week Gestational Stage Hepatic Grafts Transplanted into Immunodeficient Mice have the Capacity to Generate Well Developed, Functional Hepatic Organs Tissues Introduction: Hepatic allograft transplantation is the optimal therapeutic option for hepatic failure, a highly debilitating and potentially fatal medical condition of significant morbidity. Such transplantation, however, is often impossible to implement due to the difficulty of finding a haplotype-matched kidney donor. Moreover, even when a matched kidney donor is found, allogeneic transplantation is associated with significant drawbacks, such as the requirement for permanent administration of toxic, immunosuppressive drugs such as cyclosporin A to prevent graft rejection. Thus, there exists an urgent need for novel sources of hepatic grafts suitable for therapeutic transplantation in humans. A potentially optimal strategy for hepatic allograft transplantation would be to use gestational stage hepatic allografts, since it has been demonstrated that the earlier the developmental stage of allografts, the less vigorously such a graft tends to be rejected following transplantation into an allogeneic host. However, to date, the hypothetical existence has yet to be confirmed of specific gestational stages during which human hepatic grafts are sufficiently differentiated so as to generate functional hepatic organs without, or with minimal, risk of teratoma formation, while at the same time being sufficiently undifferentiated so as to display reduced immunogenicity, relative to adult-stage grafts, following transplantation into a non-syngeneic host. While reducing the present invention to practice, such critical limitations of the prior art were overcome, as described below.

Materials and Methods:

Animal graft hosts: Refer to Example 5, "General Materials and Methods—Transplantation of developing hepatic grafts", above.

Harvesting of human gestational stage hepatic organs/tissues: Human gestational stage hepatic organs/tissues for transplantation were obtained by extraction of organ/tissue fragments following voluntary abortions performed mechanically by aspiration at a gestational stage of 7 weeks, after obtaining informed consent. The warm ischemia time of the harvested samples was kept at under 30 minutes, and following dissection, the organ precursors were kept at 40 degrees centigrade in UW solution or PBS for less than 45 minutes under sterile conditions. The study protocol was approved by the hospital (Kaplan Medical Center, Rehovot, Israel) Helsinki committee.

Transplantation procedures: Grafts were transplanted under the renal capsule of mouse hosts as described in Example 5, "General Materials and Methods—Transplantation of developing hepatic grafts", above.

Histological Analysis: Refer to Example 5, "General Materials and Methods—Transplantation of developing hepatic grafts", above.

Experimental Results:

Human 7-week gestational stage hepatic grafts have the capacity to generate fully differentiated functional hepatic organs following transplantation into immune deficient mammalian hosts: Experiments were performed in order to analyze the capacity of human developing renal grafts to generate hepatic organs following transplantation into a host. Human 7-week gestational stage hepatic grafts were transplanted under the renal capsule of NOD/SCID mice, and tissue sections of the grafts were examined histochemically 6 weeks posttransplantation for evidence of hepatic differentiation. The grafts were surprisingly found to be capable of generating highly developed, functional hepatic organs composed of functionally differentiated hepatocytes, and having a well differentiated hepatic tissue architecture. This was clearly evidenced via H&E histochemical staining which showed a well differentiated hepatic tissue architecture including differentiated bile ducts (FIG. 24a), and via histochemical staining of graft sections with PAS which indicated significant levels of cellular glycogen synthesis and storage (FIG. 24b).

Conclusion: The presently disclosed results convincingly demonstrate for the first time that human 7-week gestational stage hepatic grafts are capable of generating fully differentiated functional hepatic organs which will be well tolerated following transplantation into an allogeneic human recipient. As such, the present findings enable a novel and highly effective method of performing therapeutic hepatic allograft transplantation. By virtue of employing gestational stage grafts, the method enabled for the first time by the present unexpected findings is far superior to prior art methods, which suffer from the ethical and medical drawbacks inherent to harvesting of organs from live human donors. Furthermore, by virtue of employing early gestational stage grafts which will be well tolerated following transplantation into a human recipient, the presently enabled method is also overwhelmingly superior to transplantation of fully differentiated hepatic grafts, the prior art method of choice, which suffers from the very significant drawback of requiring highly stringent immunological organ donor matching, and posttransplantation administration of toxic immunosuppressive drugs such as cyclosporin A for preventing graft rejection. Thus, by virtue of the aforementioned advantages thereof, the transplantation method enabled by the present results is highly suitable for treatment of diseases, such as hepatic failure, which are amenable to therapy via hepatic transplantation.

Example 8

Treatment of Human Hepatic Failure Via Transplantation of Porcine 28-Day Gestational Stage Hepatic Grafts, or Allogeneic Human 7-Week Gestational Stage Hepatic Grafts Introduction: Hepatic allograft transplantation, the optimal treatment for hepatic failure in humans, is impossible to practice in a large number of cases due to unavailability of immunologically-matched allograft donors. As shown in Example 6 above, porcine 28-day gestational stage hepatic grafts transplanted into a mammalian host are capable of generating, in the absence of teratoma formation, highly developed, functional hepatic organs in the host. As shown in Example 7 above, human 7-week gestational stage hepatic grafts transplanted into a mammalian host are capable of generating highly developed, functional hepatic organs in the host. Thus, transplantation of such developing hepatic grafts can be used for effectively treating hepatic failure in humans as described below.

Materials and Methods:

Harvesting of porcine grafts: Sows (under appropriate rearing conditions, e.g. following Good Manufacturing Practice) are brought into oestrous either by natural means (housing near males) or more likely by hormone injections known to those skilled in the art. Once the sows reach oestrous they are inseminated with semen from tested boars of a suitable quality. Following insemination, sows are monitored and tested for pregnancy as appropriate. At 28 days of gestation (full gestation 112-115 days), sows are anaesthetised and a hysterectomy is performed. The uterus is passed to a clean room and opened under sterile conditions (e.g. flow cabinet). Individual fetuses are removed, and are held in cold buffer before dissection of the developing livers. Once they have been dissected, the harvested livers are stored in vials. Each vial is labeled such that each liver can be traced back to a specific pig. Appropriate samples may be taken for biological safety evaluation. After biological safety clearance, vials are shipped to a clinical center (for example, a hospital). Alternatively, developing liver isolation may take place the clinical center, and final safety evaluation is then obtained retrospectively.

Harvesting of human grafts: Human 7-week gestational stage hepatic organs are harvested as described in Example 7 above.

Transplantation: Starting on the day of transplantation, short course costimulation blockade treatment in the form of a CTLA4-Ig administration regimen essentially corresponding to that described in Example 3 above in the context of renal transplantation, is administered to a human patient suffering from end-stage hepatic disease.

While the patient is being prepped for surgery, the hepatic grafts are prepared for transplantation.

The patient's abdomen is opened, and, depending on the patient's body weight and hepatic functionality requirements, a suitable number of developing livers are transplanted orthotopically. For example, between one and six developing livers are transplanted. Preferably at least two developing livers are transplanted to take into account possible transplant failure.

After the operation, the patient remains in the clinic or hospital to recover (for example, for about 3 or 4 days). However, it is possible that transplantation may be performed using a laparo scope, and if so the recovery time would be much shorter.

Initially, the patient may continue to undergo a normal hepatic deficiency treatment programme. The patient is monitored as required for signs of graft rejection, and appropriate immunosuppressive treatment is administered should the need arise. The growth and differentiation of graft(s) into functional hepatic organ(s) is monitored via standard liver function tests (e.g. analysis of serum levels of creatinine or bilirubin, and analysis of blood-clotting time), and via computerized tomography (CT) and/or ultrasound imaging.

The patient could return for imaging after a suitable time following discharge (for example, about 2-3 weeks following discharge). Based on clinical signs, treatment for hepatic deficiency may be continued as required, but slowly reduced (and eventually terminated) as hepatic function increases. Imaging is preferably performed regularly during the early follow-up period to monitor graft-derived hepatic organ development.

Results:

As a result of the hepatic functionality conferred to the patient by the transplanted hepatic graft(s), the end-stage hepatic disease is eventually cured, or substantially alleviated in the patient, without having required an HLA-matched human organ donor, and without the need for permanent, harmful, immunosuppression to prevent graft rejection, in sharp contrast to all prior art methods of therapeutic renal transplantation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of alleviating or stabilizing a hepatic or hepatic enzyme-deficiency disorder in a subject in need thereof, the method comprising transplanting hepatic organ precursor/tissue into the subject, said hepatic organ precursor/tissue being derived from a human liver being at a stage of development of 7 weeks of gestation.

2. The method of claim 1, further comprising treating the subject with an immunosuppressive regimen prior to, concomitantly with or following said transplanting said hepatic organ precursor/tissue into the subject, thereby promoting engraftment of said tissue in the subject.

3. The method of claim 2, wherein said treating the subject with an immunosuppressive regimen is effected by administering at least one immunosuppressant drug to the subject.

4. The method of claim 3, wherein said at least one immunosuppressant drug is capable of blocking binding of a lymphocyte coreceptor with a ligand of said lymphocyte coreceptor, and wherein said lymphocyte coreceptor is selected from the group consisting of B7-1, CD40, and CD40L.

5. The method of claim 3, wherein said administering said at least one immunosuppressant drug to the subject is effected during a time period selected from a range of 1 to 60 days.

6. The method of claim 1, wherein the subject is a mammal.

7. The method of claim 1, wherein said human liver is non-syngeneic with the subject.

8. The method of claim 1, wherein said human liver is allogeneic with the subject.

9. The method of claim 1, wherein the subject is a human subject.

10. The method of claim 1, wherein said transplanting is effected by a surgery.

11. The method of claim 1, wherein said transplanting said hepatic organ or tissue is effected into an anatomical location selected from the group consisting of a liver, a renal capsule, a sub-cutis, a omentum and a spleen.

12. The method of claim 1, wherein said hepatic organ or tissue is not circulating cells.

13. The method of claim 1, wherein said transplanting is effected using a laparoscope.

* * * * *